(12) United States Patent
Palmer et al.

(10) Patent No.: US 8,499,966 B2
(45) Date of Patent: Aug. 6, 2013

(54) METHOD OF MOVING A DELIVERY MEMBER OF A DISPENSING DEVICE FOR ADMINISTRATION OF ORAL TRANSMUCOSAL DOSAGE FORMS

(75) Inventors: Pamela Palmer, San Francisco, CA (US); Andrew I. Poutiatine, San Anselmo, CA (US); Charles Rampersaud, San Francisco, CA (US); Bruce Edwards, Menlo Park, CA (US); Edmond Chiu, San Francisco, CA (US); Thomas Schreck, Portola Valley, CA (US); Stelios Tzannis, Newark, CA (US); Larry Hamel, Mountain View, CA (US)

(73) Assignee: AcelRx Pharmaceuticals, Inc., Redwood City, CA (US)

( * ) Notice: Subject to any disclaimer, the term of this patent is extended or adjusted under 35 U.S.C. 154(b) by 384 days.

(21) Appl. No.: 12/521,983

(22) PCT Filed: Dec. 28, 2007

(86) PCT No.: PCT/US2007/089017
§ 371 (c)(1),
(2), (4) Date: Jan. 6, 2010

(87) PCT Pub. No.: WO2008/085764
PCT Pub. Date: Jul. 17, 2008

(65) Prior Publication Data
US 2010/0137836 A1 Jun. 3, 2010

Related U.S. Application Data

(63) Continuation-in-part of application No. 11/650,174, filed on Jan. 5, 2007, now Pat. No. 8,202,535, and a continuation-in-part of application No. 11/650,230, filed on Jan. 5, 2007, now Pat. No. 8,357,114, and a continuation-in-part of application No. 11/825,212, filed on Jul. 3, 2007, and a continuation-in-part of application No. 11/980,216, filed on Oct. 30, 2007.

(51) Int. Cl.
*A61M 31/00* (2006.01)
*B65H 5/00* (2006.01)

(52) U.S. Cl.
USPC .......................................... 221/232; 604/59

(58) Field of Classification Search
USPC ........................ 604/59; 221/15, 232
See application file for complete search history.

(56) References Cited

U.S. PATENT DOCUMENTS 2,621,655 A 12/1952 Olson et al.
3,444,858 A 5/1969 Russell (Continued)

FOREIGN PATENT DOCUMENTS

EP 2114383 7/2010
GB 2309966 8/1997

(Continued)

OTHER PUBLICATIONS

Drug Information Bulletin, Oct. 2004, 37(4), 4 pages, <http://www.kgh.on.ca/pharmacy/diBulletinSeptOct2004.pdf>.

(Continued)

*Primary Examiner* — Kevin C Sirmons
*Assistant Examiner* — Bradley Osinski

(57) ABSTRACT

A method of administering small, bioadhesive drug tablets includes moving an end portion of a delivery member. A surface of the delivery member can be positioned to prevent movement of the drug tablet from a tablet cartridge channel to a delivery passage of a delivery device when the end portion of the delivery member is in a first stopped position. The end portion of the delivery member can be moved to a second position within the delivery passage such that the tablet cartridge channel is in communication with the delivery passage. The drug tablet can be conveyed into the delivery passage via the tablet cartridge channel. The end portion of the delivery member can be moved to a third position within the delivery passage to convey the drug tablet through an exit opening of the delivery device.

28 Claims, 21 Drawing Sheets

U.S. PATENT DOCUMENTS

| | | |
|---|---|---|
| 3,757,781 A | 9/1973 | Smart |
| 3,780,735 A | 12/1973 | Crouter et al. |
| 3,789,845 A | 2/1974 | Long |
| 4,020,558 A | 5/1977 | Cournut et al. |
| 4,060,083 A | 11/1977 | Hanson |
| 4,229,447 A | 10/1980 | Porter |
| 4,237,884 A | 12/1980 | Erickson |
| 4,474,308 A | 10/1984 | Bergeron |
| 4,582,835 A | 4/1986 | Lewis et al. |
| 4,671,953 A | 6/1987 | Stanley et al. |
| 4,764,378 A * | 8/1988 | Keith et al. .................. 424/435 |
| 4,785,969 A | 11/1988 | McLaughlin |
| 4,863,737 A | 9/1989 | Stanley et al. |
| 4,880,634 A | 11/1989 | Speiser |
| 4,950,234 A | 8/1990 | Fujioka et al. |
| 5,080,903 A | 1/1992 | Ayache et al. |
| 5,112,616 A | 5/1992 | McCarty |
| 5,122,127 A | 6/1992 | Stanley |
| 5,178,878 A | 1/1993 | Wehling et al. |
| 5,223,264 A | 6/1993 | Wehling et al. |
| 5,236,714 A | 8/1993 | Lee et al. |
| 5,288,498 A | 2/1994 | Stanley et al. |
| 5,292,307 A | 3/1994 | Dolzine et al. |
| 5,296,234 A | 3/1994 | Hadaway et al. |
| 5,348,158 A | 9/1994 | Honan et al. |
| 5,489,025 A | 2/1996 | Romick |
| 5,489,689 A | 2/1996 | Mathew |
| 5,507,277 A | 4/1996 | Rubsamen et al. |
| 5,507,807 A | 4/1996 | Shippert |
| 5,549,560 A | 8/1996 | Van de Wijdeven |
| 5,584,805 A | 12/1996 | Sutton |
| 5,657,748 A * | 8/1997 | Braithwaite ............. 128/203.15 |
| 5,660,273 A | 8/1997 | Discko, Jr. |
| 5,694,919 A | 12/1997 | Rubsamen et al. |
| 5,710,551 A | 1/1998 | Ridgeway |
| 5,724,957 A | 3/1998 | Rubsamen et al. |
| 5,752,620 A | 5/1998 | Pearson |
| 5,785,989 A | 7/1998 | Stanley et al. |
| 5,800,832 A | 9/1998 | Tapolsky et al. |
| 5,827,525 A | 10/1998 | Liao et al. |
| 5,850,937 A | 12/1998 | Rauche |
| 5,860,946 A | 1/1999 | Hofstatter |
| 5,945,651 A | 8/1999 | Chorosinski et al. |
| 5,950,632 A | 9/1999 | Reber et al. |
| 5,954,641 A | 9/1999 | Kehr et al. |
| 5,968,547 A | 10/1999 | Reder et al. |
| 5,981,552 A | 11/1999 | Alam et al. |
| 5,984,888 A | 11/1999 | Nielsen et al. |
| 5,995,938 A | 11/1999 | Whaley |
| 5,997,518 A | 12/1999 | Laibovitz et al. |
| 6,024,981 A | 2/2000 | Khankari et al. |
| 6,039,251 A | 3/2000 | Holowko et al. |
| 6,116,414 A | 9/2000 | Discko, Jr. |
| 6,131,765 A | 10/2000 | Barry et al. |
| 6,171,294 B1 | 1/2001 | Southam et al. |
| 6,190,326 B1 | 2/2001 | McKinnon et al. |
| 6,200,604 B1 | 3/2001 | Pather et al. |
| 6,210,699 B1 | 4/2001 | Acharya et al. |
| 6,216,033 B1 | 4/2001 | Southam et al. |
| 6,230,927 B1 | 5/2001 | Schoonen et al. |
| 6,234,343 B1 | 5/2001 | Papp |
| 6,248,789 B1 | 6/2001 | Weg et al. |
| 6,264,981 B1 | 7/2001 | Zhang et al. |
| 6,284,512 B1 | 9/2001 | Jones et al. |
| 6,294,999 B1 | 9/2001 | Yarin et al. |
| 6,310,072 B1 | 10/2001 | Smith et al. |
| 6,319,510 B1 | 11/2001 | Yates |
| 6,328,159 B1 | 12/2001 | Discko, Jr. |
| 6,350,470 B1 | 2/2002 | Pather et al. |
| 6,358,944 B1 | 3/2002 | Lederman et al. |
| 6,417,184 B1 | 7/2002 | Ockert |
| 6,425,495 B1 | 7/2002 | Senda et al. |
| 6,484,718 B1 | 11/2002 | Schaeffer et al. |
| 6,488,953 B2 | 12/2002 | Halliday et al. |
| 6,495,120 B2 | 12/2002 | McCoy et al. |
| 6,500,456 B1 | 12/2002 | Capella et al. |
| 6,541,021 B1 | 4/2003 | Johnson et al. |
| 6,564,967 B1 | 5/2003 | Stringfield et al. |
| 6,576,250 B1 | 6/2003 | Pather et al. |
| 6,605,060 B1 | 8/2003 | O'Neil |
| 6,642,258 B1 | 11/2003 | Bourrie et al. |
| 6,645,528 B1 | 11/2003 | Straub et al. |
| 6,651,651 B1 | 11/2003 | Bonney et al. |
| 6,660,295 B2 | 12/2003 | Watanabe et al. |
| 6,680,071 B1 | 1/2004 | Johnson et al. |
| 6,682,716 B2 | 1/2004 | Hodges et al. |
| 6,685,951 B2 | 2/2004 | Cutler et al. |
| 6,689,373 B2 | 2/2004 | Johnson et al. |
| 6,726,053 B1 | 4/2004 | Harrold |
| 6,752,145 B1 | 6/2004 | Bonney et al. |
| 6,759,059 B1 | 7/2004 | Pettersson et al. |
| 6,761,910 B1 | 7/2004 | Pettersson et al. |
| 6,762,684 B1 | 7/2004 | Camhi et al. |
| 6,764,696 B2 | 7/2004 | Pather et al. |
| 6,776,978 B2 | 8/2004 | Rabinowitz et al. |
| 6,793,075 B1 | 9/2004 | Jeter |
| 6,796,429 B2 | 9/2004 | Cameron et al. |
| 6,824,512 B2 | 11/2004 | Warkentin et al. |
| 6,835,194 B2 | 12/2004 | Johnson et al. |
| 6,855,310 B2 | 2/2005 | Rabinowitz et al. |
| 6,881,208 B1 | 4/2005 | Phipps et al. |
| 6,914,668 B2 | 7/2005 | Brestel et al. |
| 6,932,983 B1 | 8/2005 | Straub et al. |
| 6,959,808 B2 | 11/2005 | Discko, Jr. et al. |
| 6,961,541 B2 | 11/2005 | Overy et al. |
| 6,963,289 B2 | 11/2005 | Aljadeff et al. |
| 6,969,508 B2 | 11/2005 | Dugger, III |
| 6,999,028 B2 | 2/2006 | Egbert et al. |
| 7,004,111 B2 | 2/2006 | Olson et al. |
| 7,018,619 B2 | 3/2006 | Rabinowitz et al. |
| 7,044,125 B2 | 5/2006 | Vedrine et al. |
| 7,070,762 B2 | 7/2006 | Rabinowitz et al. |
| 7,070,764 B2 | 7/2006 | Rabinowitz et al. |
| 7,070,765 B2 | 7/2006 | Rabinowitz et al. |
| 7,072,738 B2 | 7/2006 | Bonney et al. |
| 7,074,935 B2 | 7/2006 | Mathew et al. |
| 7,078,019 B2 | 7/2006 | Rabinowitz et al. |
| 7,078,218 B2 | 7/2006 | Smith et al. |
| 7,090,830 B2 | 8/2006 | Hale |
| 7,119,690 B2 | 10/2006 | Lerch et al. |
| 7,168,626 B2 | 1/2007 | Lerch et al. |
| 7,172,573 B1 | 2/2007 | Lamb |
| 7,198,172 B2 | 4/2007 | Harvey et al. |
| 7,208,604 B2 | 4/2007 | Mathew et al. |
| 7,215,295 B2 | 5/2007 | Egbert |
| 7,248,165 B2 | 7/2007 | Collins et al. |
| 7,276,246 B2 | 10/2007 | Zhang et al. |
| 7,306,812 B2 | 12/2007 | Zhang et al. |
| 7,458,374 B2 | 12/2008 | Hale et al. |
| 7,468,179 B2 | 12/2008 | Rabinowitz et al. |
| 7,484,642 B2 | 2/2009 | Bonney et al. |
| 7,500,444 B2 | 3/2009 | Bonney et al. |
| 7,540,998 B2 | 6/2009 | Terwilliger et al. |
| 7,552,728 B2 | 6/2009 | Bonney et al. |
| 7,744,558 B2 | 6/2010 | Maag |
| 2001/0020147 A1 | 9/2001 | Staniforth et al. |
| 2002/0026330 A1 | 2/2002 | Klein |
| 2002/0071857 A1 | 6/2002 | Kararli et al. |
| 2002/0142050 A1 | 10/2002 | Straub et al. |
| 2002/0160043 A1 | 10/2002 | Coleman |
| 2003/0008005 A1 | 1/2003 | Cutler |
| 2003/0015196 A1 | 1/2003 | Hodges et al. |
| 2003/0015197 A1 | 1/2003 | Hale et al. |
| 2003/0017175 A1 | 1/2003 | Cutler |
| 2003/0022910 A1 | 1/2003 | Cutler |
| 2003/0052135 A1 | 3/2003 | Conley |
| 2003/0052787 A1 | 3/2003 | Zerhusen et al. |
| 2003/0077300 A1 | 4/2003 | Wermeling et al. |
| 2003/0099158 A1 | 5/2003 | De la Huerga |
| 2003/0130314 A1 | 7/2003 | Druzgala |
| 2003/0132239 A1 | 7/2003 | Konig et al. |
| 2003/0173408 A1 | 9/2003 | Mosher et al. |
| 2003/0185872 A1 * | 10/2003 | Kochinke .................... 424/426 |
| 2003/0190290 A1 | 10/2003 | Ross |
| 2003/0232080 A1 | 12/2003 | Pather et al. |
| 2004/0017567 A1 | 1/2004 | Loicht et al. |
| 2004/0025871 A1 | 2/2004 | Davies |

| | | | |
|---|---|---|---|
| 2004/0034059 A1 | 2/2004 | Grarup et al. | |
| 2004/0080515 A1 | 4/2004 | Hagiwara | |
| 2004/0092531 A1 | 5/2004 | Chizh et al. | |
| 2004/0094564 A1* | 5/2004 | Papp | 221/25 |
| 2004/0133305 A1 | 7/2004 | Jean-Pierre | |
| 2004/0158349 A1* | 8/2004 | Bonney et al. | 700/231 |
| 2004/0170567 A1 | 9/2004 | Sackler | |
| 2004/0180080 A1 | 9/2004 | Furusawa et al. | |
| 2004/0248964 A1 | 12/2004 | Crooks et al. | |
| 2004/0253307 A1 | 12/2004 | Hague et al. | |
| 2005/0038062 A1 | 2/2005 | Burns et al. | |
| 2005/0049464 A1 | 3/2005 | Lassers et al. | |
| 2005/0054942 A1 | 3/2005 | Melker | |
| 2005/0065175 A1 | 3/2005 | Gonzales et al. | |
| 2005/0089479 A1 | 4/2005 | Rabinowitz et al. | |
| 2005/0101936 A1 | 5/2005 | Gonzales et al. | |
| 2005/0122219 A1 | 6/2005 | Petersen et al. | |
| 2005/0131386 A1 | 6/2005 | Freeman et al. | |
| 2005/0142197 A1 | 6/2005 | Moe et al. | |
| 2005/0142198 A1 | 6/2005 | Moe et al. | |
| 2005/0150488 A1* | 7/2005 | Dave | 128/200.14 |
| 2005/0150489 A1 | 7/2005 | Dunfield et al. | |
| 2005/0163838 A1 | 7/2005 | Moe | |
| 2005/0169989 A1 | 8/2005 | Moe et al. | |
| 2005/0176790 A1 | 8/2005 | Bartholomaus | |
| 2005/0177275 A1 | 8/2005 | Harvey et al. | |
| 2005/0258066 A1 | 11/2005 | Conley | |
| 2006/0026035 A1 | 2/2006 | Younkes et al. | |
| 2006/0031099 A1 | 2/2006 | Vitello et al. | |
| 2006/0039959 A1 | 2/2006 | Wessling et al. | |
| 2006/0045865 A1 | 3/2006 | Jacob et al. | |
| 2006/0062812 A1 | 3/2006 | Ross et al. | |
| 2006/0067978 A1 | 3/2006 | Heiler et al. | |
| 2006/0089858 A1 | 4/2006 | Ling | |
| 2006/0134200 A1 | 6/2006 | Vandoni et al. | |
| 2006/0216352 A1 | 9/2006 | Nystrom et al. | |
| 2006/0229570 A1 | 10/2006 | Lovell et al. | |
| 2007/0020186 A1 | 1/2007 | Stroppolo et al. | |
| 2007/0036853 A1 | 2/2007 | Agarwal et al. | |
| 2007/0071806 A1 | 3/2007 | McCarty | |
| 2007/0074722 A1 | 4/2007 | Giroux et al. | |
| 2007/0104763 A1 | 5/2007 | Jobdevairakkam et al. | |
| 2007/0185084 A1 | 8/2007 | McKinney et al. | |
| 2007/0186923 A1 | 8/2007 | Poutiatine et al. | |
| 2007/0190130 A1 | 8/2007 | Mark et al. | |
| 2007/0207207 A1 | 9/2007 | Tzannis et al. | |
| 2007/0260491 A1 | 11/2007 | Palmer et al. | |
| 2007/0286900 A1 | 12/2007 | Herry et al. | |
| 2007/0299687 A1 | 12/2007 | Palmer et al. | |
| 2008/0147044 A1 | 6/2008 | Palmer et al. | |
| 2008/0164275 A1 | 7/2008 | Poutiatine et al. | |
| 2008/0166404 A1 | 7/2008 | Tzannis et al. | |
| 2008/0203107 A1 | 8/2008 | Conley et al. | |
| 2008/0268023 A1 | 10/2008 | Palmer et al. | |
| 2009/0010992 A1 | 1/2009 | Palmer et al. | |
| 2009/0048237 A1 | 2/2009 | Palmer et al. | |
| 2009/0131479 A1 | 5/2009 | Palmer et al. | |
| 2010/0105735 A1 | 4/2010 | Palmer et al. | |
| 2010/0130551 A1 | 5/2010 | Pushpala et al. | |
| 2010/0253476 A1 | 10/2010 | Poutiatine et al. | |
| 2010/0256190 A1 | 10/2010 | Palmer et al. | |
| 2011/0091544 A1 | 4/2011 | Palmer | |
| 2011/0288128 A1 | 11/2011 | Palmer et al. | |
| 2012/0035216 A1 | 2/2012 | Palmer et al. | |
| 2012/0232473 A1 | 9/2012 | Poutiatine et al. | |

FOREIGN PATENT DOCUMENTS

| | | |
|---|---|---|
| JP | 2000-142841 | 5/2000 |
| JP | 2003-525081 | 8/2003 |
| JP | 2007-517636 | 7/2007 |
| WO | WO 00/16750 | 3/2000 |
| WO | WO 00/57858 | 10/2000 |
| WO | WO 01/30288 | 5/2001 |
| WO | WO 01/64182 | 7/2001 |
| WO | WO 01/97780 | 12/2001 |
| WO | WO 02/32487 | 4/2002 |
| WO | WO 02/074372 | 9/2002 |
| WO | WO 02/078594 | 10/2002 |
| WO | WO 03/092575 | 11/2003 |
| WO | WO 2004/067004 | 8/2004 |
| WO | WO 2004/069198 | 8/2004 |
| WO | WO 2004/080515 | 9/2004 |
| WO | WO 2006/097361 | 9/2006 |

OTHER PUBLICATIONS

Chelly, J. E. et al., "The safety and efficacy of a fentanyl patient-controlled transdermal system for acute postoperative analgesia: a multicenter, placebo-controlled trial," Anesth. Analg., 98:427-433 (2004).

Culling et al., "Haemodynamics and plasma concentrations following sublingual GTN and intravenous, or inhaled isosorbide dinitrate," Br. J. Clin. Pharm., 17:125-131 (1984).

FDA Guidance for Industry: Container Closure Systems for Packaging Human Drugs and Biologics, pp, 1-E2 (1999).

Fentora™ Package Insert (2006).

Fentora®, 2008 Red Book, p. 174.

Griffin, D. et al., Reg. Anesth. Pain Med., vol. 10, American Society of Regional Anesthesia Spring Meeting (2010).

Infusion Pump Improvement Initiative, Center for Devices and Radiological Health, U.S. Food and Drug Administration, Apr. 2010, 7 pages.

Keohane, C. A. et al., "Intravenous medication safety and smart infusion systems," Journal of Infusion Nursing, 28(5):321-328 (Sep./Oct. 2005).

Kotey, G. A. et al., "Iontophoretic delivery of fentanyl for acute post-operative pain management," The European Journal of Hospital Pharmacy Science, 13(1):3-9 (2007).

Lin, L. et al., "Applying human factors to the design of medical equipment: patient-controlled analgesia," J. Clin. Monitoring and Computing, 14:253-263 (1998).

McInnes, F, et al., "Evaluation of the clearance of a sublingual buprenorphine spray in the beagle dog using gamma scintigraphy," Pharmaceutical Research, (2007), 6 pages.

Miaskowski, C., "Patient-controlled modalities for acute postoperative pain management," Journal of PeriAnesthesia Nursing, 20(4):255-267 (Aug. 2005).

Miller, R. D., "The pursuit of excellence. The 47th Annual Rovenstine Lecture," Anesthesiology, 110(4):714-720 (Apr. 2009).

Minkowitz et al., Reg. Anesth. Pain Med., vol. 8, American Society of Regional Anesthesia Spring Meeting (2010).

Momeni, M. et al., "Patient-controlled analgesia in the management of postoperative pain," Drugs, 66(18):2321-2337 (2006).

Onsolis Package Insert (Jul. 2009), 11 pages.

Paix, A. et al., "Subcutaneous fentanyl and sufentanil infusion substitution for morphine intolerance in cancer pain management," Pain, 63:263-269 (1995).

Paradis et al., "Solid-phase microextraction of human plasma samples for determination of sufentanil by gas chromatography-mass spectrometry," Therapeutic Drug Monitoring, 24:768-774 (2002).

Rawal, N. et al., "Current practices for postoperative pain management in Europe and the potential role of the fentanyl HCl iontophoretic transdermal system," European Journal of Anaesthesiology, 24:299-308 (2007).

Rosati, J. et al., "Evaluation of an oral patient-controlled analgesia device for pain management in oncology inpatients," J. Support. Oncol., 5(9):443-448 (2007).

Rothschild, J. M. et al., "A controlled trial of smart infusion pumps to improve medication safety in critically ill patients," Crit. Care Med., 33(3):533-540 (2005).

Sanford et al., "A comparison of morphine, fentanyl, and sufentanil anesthesia for cardiac surgery: induction, emergence, and extubation," Anesthesia and Analgesia, 65:259-266 (1986).

Shojaei, A. H. et al., "Buccal mucosa as a route for systemic drug delivery: a review," Journal of Pharmacy and Pharmaceutical Sciences, 1:15-30 (1998).

Slatkin at al., "Fentanyl Buccal Tablet for Relief of Breakthrough Pain in Opioid-Tolerant Patients With Cancer-Related Chronic Pain," J. of Supportive Oncol., vol. 5, No. 7, Jul./Aug. 2007, pp. 327-334.

Vadivelu, N. et al., "Recent advances in postoperative pain management," Yale Journal of Biology and Medicine, 83:11-25 (2010).

Van Raders, P. et al., "Nurses' views on ease of patient care in postoperative pain management," British Journal of Nursing, 16(5):312-317 (2007).

Vasight, N. et al., "Formulation selection and pharmacokinetic comparison of fentanyl buccal soluble film with oral transmucosal fentanyl citrate," Clin. Drug Investig., 29(10):647-654 (2009).

Vercauteren, M. P. et al., "Epidural sufentanil for postoperative patient-controlled analgesia (PCA) with or without background infusion: a double-blind comparison," Anesth. Analg., 80:76-80 (1995).

Viscusi, E. R., "Patient-controlled drug delivery for acute postoperative pain management: a review of current and emerging technologies," Regional Anesthesia and Pain Medicine, 33(2):146-158 (2008).

International Search Report and Written Opinion for International Application No. PCT/US2007/010822, mailed Aug. 5, 2008.

International Search Report and Written Opinion for International Application No. PCT/US2007/011337, mailed Aug. 21, 2008.

Office Action for U.S. Appl. No. 11/974,092, mailed Jun. 13, 2011.

Office Action for Japanese Patent Application No. 2009-544898, mailed Jul 24, 2012.

Office Action for Japanese Application No. 2009-544899, mailed Aug. 1, 2012.

Office Action for U.S. Appl. No. 13/416,236, mailed Feb. 4, 2013.

Office Action for Canadian Application No. 2,636,115, dated Feb. 12, 2013.

Abrams, R. et al., "Safety and Effectiveness of Intranasal Administration of Sedative Medications (Ketamine, Midazolam, or Sufentanil) for Urgent Brief Pediatric Dental Procedures," Anesth Prog., 40:63-66 (1993).

AcelRx Pharmaceuticals, Inc., "AcelRx Pharmaceuticals Reports Positive Results from a Clinical Trial of Sublingual Sufentanil/Triazolam NanoTabTM Combination (ARX-03) in Treating Procedural Pain and Anxiety," Jan. 12, 2009, pp. 1-2.

AHFS Drug Information, 28:08.08, 2157-2160 (2007).

Ahmad, S. et al., "Fentanyl HCl iontophoretic transdermal system versus intravenous morphine pump after gynecologic surgery," Arch Gynecol Obstet 276:251-258 (2007).

Albert, J. M. et al., "Patient-Controlled Analgesia vs. Conventional Intramuscular Analgesia Following Colon Surgery," Diseases of the Colon & Rectum, 31(2):83-86 (1988).

Anlar, S. et al., "Formulation and in Vitro-In Vivo Evaluation of Buccoadhesive Morphine Sulfate Tablets," Pharm. Res., 11(2):231-236 (1994).

ACTIQ® Fact Sheet (Mar. 2004).

Bayrak, F. et al., "A Comparison of Oral Midazolam, Oral Tramadol, and Intranasal Sufentanil Premedication in Pediatric Patients," J. Opiod. Management, 3(2):74-78 (2007).

Berthold, C. W. et al., "Comparison of Sublingually and Orally Administered Triazolam for Premedication Before Oral Surgery," Oral Surg Oral Med Oral Pathol Oral Radiol Endo, 84(2):119-124 (1997).

Bethune-Volters, A., "A Randomized Double-Blind Trial Assessing the Efficacy and Safety of Sublingual Metopimazine and Ondansetron in the Prophylaxis of Chemotherapy-Induced Delayed Emesis," Anti-Cancer Dugs, 17(2):217-224 (2006).

Bovill, G. J. et al., "The Pharmacokinetics of Sufentanil in Surgical Patients," Anesthesiology, 61:502-506 (1984).

Bredenberg, S., "New Concepts in Administration of Drugs in Tablet Form—Formulations and Evaluation of a Sublingual Tablet for Rapid Absorption, and Presentation of an Individualised Dose Administration System," Comprehensive Summaries of Uppsala Dissertations from the Faculty of Pharmacy 287, ACTA Universitatis Upsaliensis Uppsala (2003).

Bredenberg, S. et al., "In Vitro and in Vivo Evaluation of a New Sublingual Tablet System for Rapid Oromucosal Absorption Using Fentanyl Citrate as the Active Substance," European Journal of Pharmaceutical Sciences, 20:327-334 (2003).

Brusset, A. et al., "Comparative Pharmacokinetic Study of Fentanyl and Sufentanil After Single High-Bolus Doses," Clin Drug Invest, 18(5):377-389 (1999).

Chauvin, M., "Sufentanil Pharmacokinetics in Patients With Cirrhosis," Anesth Analg, 68(1):1-4 (1989).

Christie, J. M. et al., "Dose-titration, multi-center study of oral transmucosal fentanyl citrate for the treatment of breakthrough pain in cancer patients using transdermal fentanyl for persistent pain," J Clin Oncol., 16(10):3238-45 (1998).

Coda, B. A. et al., "Comparative efficacy of patient-controlled administration of morphine, hydromorphone, or sufentanil for the treatment of oral mucositis pain following bone marrow transplantation," Pain, 72:333-346 (1997).

Collins, L. M. C. et al., "The Surface Area of the Adult Human Mouth and Thickness of the Salivary Film Covering the Teeth and Oral Mucosa," J Dent Res, 66(8):1300-2 (1987).

Coluzzi, P. H. et al., "Breakthrough Cancer Pain: A Randomized Trial Comparing Oral Transmucosal Fentanyl Citrate (OTFC) and Morphine Sulfate Immediate Release (MSIR)," Pain, 91(1-2):123-130 (2001).

Dale, O. et al., "Nasal Administration of Opioids for Pain Management in Adults," Acta Anaesthesiol. Scand., 46:759-770 (2002).

Darwish, M. et al., "Single-Dose and Steady-State Pharmacokinetics of Fentanyl Buccal Tablet in Healthy Volunteers," Journal of Clinical Pharmacology, 47(1):56-63 (2007).

Darwish, M. et al., "Pharmacokinetics and Dose Proportionality of Fentanyl Effervescent Buccal Tablets in Healthy Volunteers," Clinical Pharmacokinetics, 44(12): 1279-1286 (2005).

Darwish, M. et al., "Comparison of Equivalent Doses of Fentanyl Buccal Tablets and Arteriovenous Differences in Fentanyl Pharmacokinetics," Clinical Pharmacokinetics, 45(8):843-350 (2006).

Darwish, M. et al., "Pharmacokinetic Properties of Fentanyl Effervescent Buccal Tablets: A Phase I, Open-Label, Crossover Study of Single-Dose 100, 200, 400, and 800 μg In Healthy Adult Volunteers," Clinical Therapeutics, 28(5):707-714 (2006).

Darwish, M. et al., "Relative Bioavailability of the Fentanyl Effervescent Buccal Tablet (FEBT) 1080 μg Versus Oral Transmucosal Fentanyl Citrate 1600 μg and Dose Proportionality of FEBT 270 to 1300 μg: A Single-Dose, Randomized, Open-Label, Three-Period Study in Healthy Adult Volunteers," Clinical Therapeutics, 28(5):715-724 (2006).

Darwish, M. et al., "Effect of Buccal Dwell Time on the Pharmacokinetic Profile of Fentanyl Buccal Tablet," Expert Opin. Pharmacother., 8(13):2011-2016 (2007).

Darwish, M. et al., "Bioequivalence Following Buccal and Sublingual Placement of Fentanyl Buccal Tablet 400 μg in Healthy Subjects," Clin. Drug Invest., 28(1):1-7 (2008).

Darwish, M. et al., "Absolute and Relative Bioavailability of Fentanyl Buccal Tablet and Oral Transmucosal Fentanyl Citrate," Journal of Clinical Pharmacology, 47:343-350 (2007).

De Castro, J. et al., "Practical Applications and Limitations of Analgesic Anesthesia," Acta Anesthesiologica Belgica, 3:107-128 (1976).

Demeules et al., "Clinical Pharmacology and Rationale of Analgesic Combinations," European Journal of Anaesthesiology, 20(28):7-12 (2003).

DeVries, M. et al., "Developments in Buccal Drug Delivery," Critical Reviews in Therapeutic Drug Carrier Systems, 8(3):271-303 (1991).

Durfee, S. et al., "Fentanyl Effervescent Buccal Tablets: Enhanced Buccal Absorption," American Journal of Drug Delivery, 4(1):1-5(5) (2006).

Egan, T. D. et al., "Multiple Dose Pharmacokinetics of Oral Transmucosal Fentanyl Citrate in Healthy Volunteers," Anesthesiology, 92:665-673 (2000).

Ellmauer, S., "Sufentanil: An Alternative to Fentanyl/Alfentanil?" Anesth, 43(3):143-158 (1994).

Enting, H. R. et al., "The 'Pain Pen' for Breakthrough Cancer Pain: A Promising Treatment," Journal of Pain and Symptom Management, 29(2):213-217 (2005).

Farnsworth, S. T. et al., "Ocular Transmucosal Absorption and Toxicity of Sufentanil in Dogs," Anesth. Analg., 86:138-140 (1998).

Fisher, D.M. et al., "Pharmacokinetics of an Implanted Osmotic Pump Delivering Sufentanil for the Treatment of Chronic Pain," Anesthesiology, 99(4):929-37 (Oct. 2003).

Gardner-Nix, J., "Oral Transmucosal Fentanyl and Sufentanil for Incident Pain," Journal of Pain and Symptom Management, 22(2):627-630 (2001).

Geldner, G. et al., "Comparison Between Three Transmucosal Routes of Administration of Midazolam in Children," Paediatric Anaesthesia, 7(2):103-109 (1997).
Gerak. L. R. et al., "Studies on Benzodiazepines and Opioids Administered Alone and in Combination in Rhesus Monkeys: Ventilaion and Drug Discrimination," Psychopharmacology, 137(2):164-174 (1998).
Gordon, D. B., "Oral Transmucosal Fentanyl Citrate for Cancer Breakthrough Pain: A Review," Oncol. Nurs. Forum, 33(2):257-264 (2006).
Gram-Hansen, P. et al., "Plasma Concentrations Following Oral and Sublingual Administration of Lorazepam," Int. J. Clin. Pharmacol. Ther. Toxicol., 26(6):323-324 (1988).
Grass, J., "Patient-Controlled Analgesia," Anesth. Analg., 101:S44-S61 (2005).
Guay, J. et al., "Pharmacokinetics of Sufentanil in Normal Children," Canadian Journal of Anaesthesia, 39(1):14-20 (1992).
Halliburton, J. R., "The Pharmacokinetics of Fentanyl, Sufentanil and Alfentanil: A Comparative Review," Journal of the American Association of Nurse Anesthetists, 56(3):229-233 (1988).
Haynes, G. et al., "Plasma Sufentantil Concentration After Intranasal Administration to Paediatric Outpatients," Canadian Journal of Anaesthesia, 40(3):286-288 (1993).
Hazardous Substances Data Bank (HSDB) [online] [Retrieved from the Internet]. URL: http://toxnet.nlm.nih.gov. Apr. 9, 2007, Name: Sufentanil; RN: 56030-54-7.
Helmers, J. H. et al., "Sufentanil Pharmacokinetics in Young Adult and Elderly Surgical Patients," European Journal of Anaesthesiology, 11(3):181-185 (1994).
Helmers, J. H. et al., "Comparison of Intravenous and Intranasal Sufentanil Absorption and Sedation," Canadian Journal of Anaesthesia, 36(5):494-497 (1989).
Henderson, J.M. et al., "Pre-Induction of Anesthesia in Pediatric Patients with Nasally Administered Sufentanil," Anesthesiology, 68:671-675 (1988).
Heshmati et al., "Intranasal Sufentanil for Postoperative Pain control in Lower Abdominal Pediatric Surgery," Iran. J. Pharmacol. Therap., 5:131-133 (2006).
Hicks, R. et al., "USP Medication Safety Forum: Medication Errors Involving Patient-Controlled Analgesia," Joint Commission on Quality and Patient Safety, 34(12):734-742 (2008).
Ikinci, G. et al., "Development of buccal bioadhesive nicotine tablet formulation for smoking cessation," Int. J. Pharm, 277(1-2):173-178 (2004).
Jackson, D. et al., "Pharmacokinetics and Clinical Effects of Multidose Sublingual Triazolam in Healthy Volunteers," Journal Clinical Psychopharmacology, 26(1):4-8 (2006).
Jackson, K. et al., "Pilot Dose Finding Study of Intranasal Sufentanil for Breakthrough and Incident Cancer-Associated Pain," Journal of Pain and Symptom Management, 23(6):450-452 (2002).
James et al., "The Use of a Short-Acting Benzodiazepine to Reduce the Risk of Syncopal Episodes During Upright Sterotactic Breast Biopsy," Clinical Radiology, 60(3):394-396 (2005).
Jeannet, P. et al., "Home and Hospital Treatment of Acute Seizures in Children with Nasal Midazolam," Eur. J. Paediatric Neurology, 3(2):73-77 (1999).
Kaplan, G. B. et al., "Single-Dose Pharmacokinetics and Pharmacodynamics of Alprazolam in Elderly and Young Subjects," J Clin Pharmacol, 38(1):14-21 (1998).
Karl et al., "Comparison of the Safety and Efficacy of Intranasal Midazolam of Sufentanil for Preinduction of Anesthesia in Pediatric Patients," Anesthesiology, 76:209-215 (1992).
Karl, H. W. et al., "Transmucosal Administration of Midazolam for Premedication of Pediatric Patients," Anesthesiology, 78(5):885-891 (1993).
Karl, H. W. et al., "Pharmacokinetics of Oral Triazolam in Children," Journal Clinical Psychopharmacology, 17(3):169-172 (1997).
KGH Drug Information Bulletin, "Sublingual Sufentanil for Incident Pain," KGH Drug Information Bulletin, 37(4):2 (2004).
Khalii S. et al., Sublingual Midazolam Premedication in Children: A Dose Response Study, Paediatric Anaesthesia, (8):461-465 (1998).
Kogan et al., "Premedication with Midazolam in Young Children: A Comparison of Four Routes of Administration," Paediatric Anaesthesia, 12(8):685-689 (2002).
Kontinen, V. et al, "Premedication with Sublingual Triazolam Compared with Oral Diazepam," Canadian Journal of Anesthesia, 40:829-834 (1993).
Kress et al., "Efficacy and Tolerability of Intranasal Fentanyl Spray 50 to 200 μg For Breakthrough Pain in Patients With Cancer: A Phase III Multinantional, Randomized, Double-Blind, Placebo-Controlled, Crossover Trial With a 10-Month, Open-Label Extension Treatment Period," Clinical Therapeutics, 31(6): 1171-1191 (2009).
Kroboth, P. D. et al, "Triazolam Pharmacokinetics After Intravenous, Oral and Sublingual Administration," J. Clin. Psychopharmacol., 15(4):259-262 (1995).
Kunz, K. M., et al., "Severe Episodic Pain: Management with Sublingual Sufentanil," Journal of Pain and Symptom Management, 8(4):189-190 (1993).
Lehman, K. A. et al., "Postoperative patient-controlled analgesia with sufentanil: analgesic efficacy and minimum effective concentrations," Acta Anaesthesiol Scand., 35:221-226 (1991).
Lehman, K. A. et al., "Pharmacokinetics of sufentanil in general surgical patients under different conditions of anesthesia," Acta Anaesthesiol Scand., 37:176-180 (1993).
Lennernas, B. et al., "Pharmacokinetics and Tolerability of Different Doses of Fentanyl Following Sublingual Administration of a Rapidly Dissolving Tablet to Cancer Patients: A New Approach to Treatment of Incident Pain," British Journal of Clinical Pharmacology, 59(2):249-253 (2004).
Lichtor, J. L., "The Relative Potency of Oral Transmucosal Fentanyl Citrate (OTFC) Compared With Intravenous Morphine in the Treatment of Moderate to Severe postoperative Pain," Anesth. Anal., 89(3):732-738 (1999).
Lim, T. W. et al., "Premedication with Midazolam is More Effective by the Sublingual than Oral Route," Can J Anaesth, 44(7):723-726 (1997).
Lipworth et al., "Pharmacokinetics, Effacacy and Adverse Effects of Sublingual Salbutamol in Patients with Asthma," Europoean Journal of Clinical Pharmacology, 37(6):567-571 (1989).
Mather, L. E., "Clinical Pharmacokinetics of Fentanyl and its Newer Derivatives," Clinical Pharmacokinetics, 8:422-446 (1983).
Mathieu, N. et al., "Intranasal Sufentanil is Effective for Postoperative Analgesia in Adults," Canadian Journal of Anaesthesia, 53(1):60-66 (2006).
McCann et al., "The Management of Preoperative Anxiety in Children: An Update," Anesthesia & Analgesia, 93:98-105 (2001).
Mendelson, J. et al., "Bioavailability of Sublingual Buprenorphine," J. Clin. Pharmacol., 37:31-37 (1997).
Molander, L. et al., "Pharmacokinetic investigation of a nicotine sublilngual tablet," Eur. J. Clin. Pharmacol., 56(11):813-819(2001).
Monk, J. P. et al., "Sufentanil: A Review of Its Pharmacological Properties and Therapeutic Use," Drugs, 36:286-313 (1988).
Motwani, J. G. et al., Clin Pharmacokinet, 21(2):83-94 (1991).
Mystakidou, K. et al., Oral Transmucosal Fentanyl Citrate: Overview of Pharmacological and Clinical Characteristics, Drug Deliv., 13(4):269-76 (2006).
Naguib et al., "The Comparative Dose-Response Effects of Melatonin and Midazolam for Premedication of Adult Patients: A Double-Blinded, Placebo-Controlled Study," Anesth. Analg., 91(2):473-479 (2000).
Nath, R. P. et al., Buprenorphine pharmacokinetics: relative bioavailability of sublingual tablet and liquid formulations, J Clin Pharmacol., 39:619-623 (1999).
Odou, P. et al., "Development of Midazolam Sublingual Tablets: in Vitro Study," European Journal of Drug Metabolism Pharmacokinetics, 23(2):87-91 (1998).
Odou et al., "Pharmacokinetics of Midazolam: Comparison of Sublingual and Intravenous Routes in Rabbit," European Journal of Drug Metabolism Pharmacokinetics, 24(1):1-7 (1999).
Okayama et al., "Bronchodilator Effect of Sublingual Isosorbide Dinitrate in Asthma," Eur J Clin Pharamcol, 26(2):151-155 (1984).
Paix, A. et al., Subcutaneous fentanyl and sufentanil infusion substitution for morphine intolerance in cancer pain management, Pain, 63:263-269 (1995).

Pavlin et al., "Effects of Combining Propofol and Alfentanil on Ventilation, Analgesia, Sedation, and Emesis in Human Volunteers," Anesthesiology, 84(1):23-37 (1996).
Portenoy, R. K. et al., "A Randomized, Placebo-controlled Study of Fentanyl Buccal Tablet for Breakthrough Pain in Opioid-treated Patients with Cancer," The Clinical Jour. of Pain, 22(9):805-811 (2006).
Portenoy, R. K. et al., Pain, 79:303-312 (1999).
Puig, M. M. et al., "Sufentanil Pharmacokinetics in Neurosurgical Patients," Int'l J Clin Pharmaco Ther and Toxicol, 27(5):229-34 (1989).
Raza et al., "Haemodynamic Stability with Midazolam-Ketamine-Sufentanil Analgesia in Cardiac Patients," Can. J. Anaesth., 36(6):617-623 (1989).
Reisfield, G. et al., "Rational Use of Sublingual Opioids in Palliative Medicine," Journal of Palliative Medicine, 10(2):465-475 (2007).
Reynolds, L. et al., Relative analgesic potency of fentanyl and sufentanil during intermediate-term infusions in patients after long-term opiod treatment for chronic pain, Pain, 110:182-188 (2004).
Rosow, C. E., "Sufentanil Citrate: A New Opioid Analgesic for Use in Anesthesia," Pharmacotherapy, 4:11-19 (1984).
Roy, S. D., "Transdermal Delivery of Narcotic Analgesics: pH, Anatomical, and Subject Influences on Cutaneous Permeability of Fentanyl and Sufentanil," Pharm. Res., 7:842-847 (1990).
Roy, S. D. et al., "Solubility behavior of narcotic analgesics in aqueous media: solubilities and dissociation constants of morphine, fentanyl and sufentanil," Pharm. Research, 6(2):147-151 (1989).
Savoia, G. et al., "Sufentanil: an overview of its use for acute pain management," Minerva Anesth, 67(9 Suppl 1):206-216 (2001).
Scavone, J. M. et al., "Enhanced Bioavailability of Triazolam Following Sublingual Versus Oral Administration," J Clin Pharmacol, 26(3):208-210 (1986).
Scavone, J. M. et al., "Alprazolam Kinetics Following Sublingual and Oral Administration," J Clin Psychpharmacol, 7(5):332-334 (1987).
Scavone, J. M. et al., "The Pharmacokinetics and Pharmacodynamics of Sublingual and Oral Alprazolam in the Post-Pradial State," Eur J Clin Pharmacol, 42(4):439-443 (1992).
Scholz, J. et al., Clinical Pharmacokinetics of Alfentanil, Fentanyl and Sufentanil, Clin. Pharmacokin., 31:275-292 (1996).
Schreiber, K. M. et al., "The Association of Preprocedural Anxiety and the Success of Procedural Sedation in Children," The American Journal of Emergency Medicine, 24(4):397-401 (2006).
Schwagmeier, R. et al., "Midazolam Pharmacokinetics Following Intravenous and Buccal Administration," Br. J. Clin. Pharmacol., 46:203-206 (1998).
Siepmann, J. et al., "Calculation of the Required Size and Shape of Hydroxypropyl Methylcellulose Matrices to Achieve Desired Drug Release Profiles," International Journal of Pharmaceutics, 201(1):151-164 (2000).
Sinatra, R. S. et al., "Patient-Controlled Analgesia with Sufentanil: A Comparison of Two Different Methods of Administration," Journal of Clinical Anesthesia, 8:123-129 (1996).
Smith, R. B. et al., "Temporal variation in traizolam pharmacokinetics and pharmacodynamics after oral administration," J Clin Pharmacol., 26(2):120-4 (1986).
Stopperich, P. S. et al., "Oral Triazolam Pretreatment for Intravenous Sedation," Anesth Prog, 40(4):117-121 (1993).
Streisand, J. B. et al., Absorption and Bioavailability of Oral Transmucosal Fentanyl Citrate, Anesthesiology, 75:223-229 (1991).
Streisand, J. B. et al., Dose Proportionality and Pharmacokinetics of Oral Transmucosal Fentanyl Citrate, Anesthesiology, 88:305-309 (1998).
Striebel, H. W. et al., "Patient-controlled intranasal analgesia (PCINA) for the management of postoperative pain: a pilot study," J Clin Anesth, 8:4-8 (1996).
Striebel, H. W. et al., "Patient-controlled intranasal analgesia: a method for noninvasive postoperative pain management," Anesth Analg, 83:548-51 (1996).
SUFENTA® Package Insert (2006).
Tweedy, C. M. et al., "Pharmacokinetics and Clinical Effects of Sublingual Triazolam in Pediatric Dental Patients," Journal of Clinical Psychopharmacology, 21(3):268-272 (2001).
Van De Walle, J. et al., "Double blind comparison of fentanyl and sulfentanil in anesthesia," Acta Anaesth Belg, 27(3):129-138 (2009).
Vercauteren, M., "Intranasal Sufentanil for Pre-Operative Sedation," Anaesthesia, 43(4):270-273 (1988).
Viitanen et al., "Midazolam Premedication Delays Recovery from Propofol-Induced Sevoflurane Anesthesia in Children 1-3 yr," Canadian Journal of Anesthesia, 46(8):766-771 (1999).
Viscusi, E. R. et al., "An iontophoretic fentanyl patient-activated analgesic delivery system for postoperative pain: a double-blind, placebo-controlled trial," Anesth Analg., 102(1):188-194 (2006).
Viscusi, E. R. et al., "Patient-Controlled Transdermal Fentanyl Hydrochloride vs Intravenous Morphine Pump for Postoperative Pain: A randomized controlled trial," JAMA, 291(11):1333-1341 (2004).
Walder et al., Analgesia and Sedation in Critically Ill Patients, Swiss Med. Wkly., 134(23-24):333-346 (2004).
Weinberg, D. S. et al., "Sublingual Absorption of Selected Opioid Analgesics," Clin. Pharmacol. Ther., 44(3):335-342 (1988).
Wheeler, M. et al., "Uptake Pharmacokinetics of the Fentanyl Oralet in Children Scheduled for Central Venous Access Removal: Implications for the Timing of Initiating Painful Procedures," Paediatric Anesthesia, 12:594-599 (2002).
Willens, J. S. et al., "Pharmacodynamics, Pharmacokinetics, and Clinical Uses of Fentanyl, Sufentanil, and Alfentanil," Heart and Lung, 22:239-251 (1993).
Yager, J. Y. et al., "Sublingual Lorazepam in Childhood Serial Seizures," Am J Dis Child, 142:931-932 (1988).
Yeomans et al., "Sublingual Sufentanil," Vancouver Hospital and Health Science Center Drug and Therapeutics Newsletter, 8(1):2 (2001).
Zedie, N. et al., "Comparison of Intranasal Midazolam and Sufentanil Premedication in Pediatric Outpatients," Clin. Pharmacol. Ther., 59:341-348 (1996).
Zhang, H. et al., "Oral Mucosal Drug Delivery: Clinical Pharmacokinetics and Therapeutic Applications," Clinical Pharmacokinetics, 41(9):661-680 (2002).
International Search Report and Written Opinion for International Application No. PCT/US2011/037401, mailed Aug. 19, 2011.
Office Action for U.S. Appl. No. 12/580,930, mailed Oct. 21, 2011.
International Search Report and Written Opinion for International Application No. PCT/US2010/027437, mailed Jun. 21, 2010.
Office Action for U.S. Appl. No. 12/275,485, mailed Mar. 2, 2011.
Office Action for U.S. Appl. No. 12/275,485, mailed Nov. 23, 2011.
International Search Report and Written Opinion for International Application No. PCT/US2009/064232, mailed Mar. 17, 2010.
Office Action U.S. Appl. No. 11/429,904, mailed Sep. 17, 2008.
Office Action U.S. Appl. No. 11/429,904, mailed Mar. 5, 2009.
Office Action U.S. Appl. No. 11/429,904, mailed Aug. 20, 2009.
Office Action U.S. Appl. No. 11/473,551, mailed Sep. 26, 2008.
Office Action U.S. Appl. No. 11/473,551, mailed Mar. 16, 2009.
Office Action U.S. Appl. No. 11/473,551, mailed Sep. 11, 2009.
International Search Report and Written Opinion for International Application No. PCT/US2008/072445, mailed Oct. 20, 2008.
Office Action for U.S. Appl. No. 11/650,227, mailed Dec. 9, 2008.
Office Action for U.S. Appl. No. 11/650,227, mailed Jul. 6, 2009.
Office Action for U.S. Appl. No. 11/650,227, mailed Dec. 15, 2009.
Office Action for U.S. Appl. No. 11/650,227, mailed Aug. 5, 2010.
Office Action for U.S. Appl. No. 11/825,251, mailed Sep. 21, 2009.
Office Action for U.S. Appl. No. 11/825,251, mailed Dec. 15, 2009.
Office Action for U.S. Appl. No. 11/825,251, mailed Aug. 5, 2010.
International Search Report and Written Opinion for International Application No. PCT/US2007/000528, mailed Feb. 4, 2008.
Office Action for U.S. Appl. No. 11/650,174, mailed Oct. 13, 2010.
Office Action for U.S. Appl. No. 11/650,174, mailed Jun. 14, 2011.
Written Opinion for International Application No. PCT/US2007/000529, mailed Sep. 11, 2007.
International Preliminary Report on Patentability for International Application No. PCT/US2007/000529, dated Jul. 8, 2008.
Supplementary European Search Report for European Application No. EP07716450, mailed Apr. 6, 2011.
Office Action for U.S. Appl. No. 11/650,230, mailed Sep. 25, 2008.
Office Action for U.S. Appl. No. 11/650,230, mailed Mar. 10, 2009.
Office Action for U.S. Appl. No. 11/650,230, mailed Aug. 4, 2009.

Office Action for U.S. Appl. No. 11/650,230, mailed Feb. 2, 2010.
Office Action for U.S. Appl. No. 11/650,230, mailed Jun. 16, 2010.
Office Action for U.S. Appl. No. 11/650,230, mailed Mar. 1, 2011.
Office Action for U.S. Appl. No. 11/650,230, mailed Mar. 27, 2012.
International Search Report and Written Opinion for International Application No. PCT/US2007/000527, mailed Dec. 17, 2007.
International Preliminary Report on Patentability for International Application No. PCT/US2007/000527, dated Feb. 24, 2009.
Restriction Requirement for U.S. Appl. No. 11/825,212, mailed Dec. 9, 2009.
Office Action for U.S. Appl. No. 11/825,212, mailed Mar. 24, 2010.
Office Action for U.S. Appl. No. 11/825,212, mailed Aug. 31, 2010.
International Search Report and Written Opinion for International Application No. PCT/US2007/089016, mailed Jun. 17, 2008.
International Preliminary Report on Patentability for International Application No. PCT/US2007/089016, dated Jul. 7, 2009.
Office Action for U.S. Appl. No. 11/974,092, mailed Sep. 30, 2009.
Office Action for U.S. Appl. No. 11/974,092, mailed Mar. 31, 2010.
Office Action for U.S. Appl. No. 11/980,216, mailed Dec. 24, 2008.
Office Action for U.S. Appl. No. 11/980,216, mailed Jul. 20, 2009.
Office Action for U.S. Appl. No. 11/980,216, mailed Jan. 5, 2010.
Office Action for U.S. Appl. No. 11/980,216, mailed Jul. 2, 2010.
International Search Report and Written Opinion for International Application No. PCT/US2007/089017, mailed Jun. 23, 2008.
International Preliminary Report on Patentability for International Application No. PCT/US2007/089017, dated Jul. 7, 2009.
Office Action for U.S. Appl. 11/985,162, mailed Dec. 20, 2010.
International Search Report and Written Opinion for International Application No. PCT/US2007/089018, mailed Oct. 15, 2008.
Office Action for U.S. Appl. No. 12/187,937, mailed Sep. 16, 2010.

* cited by examiner

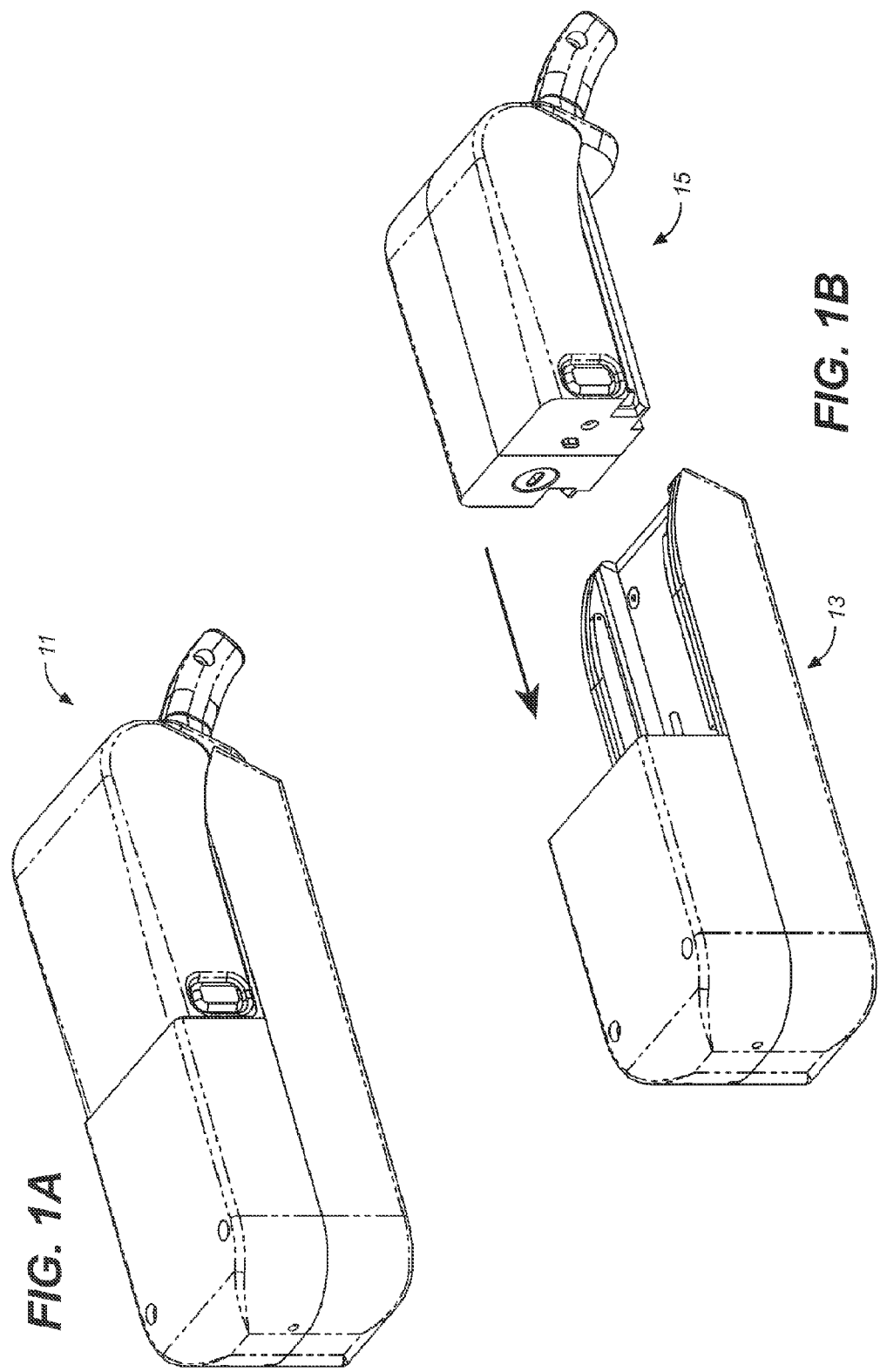

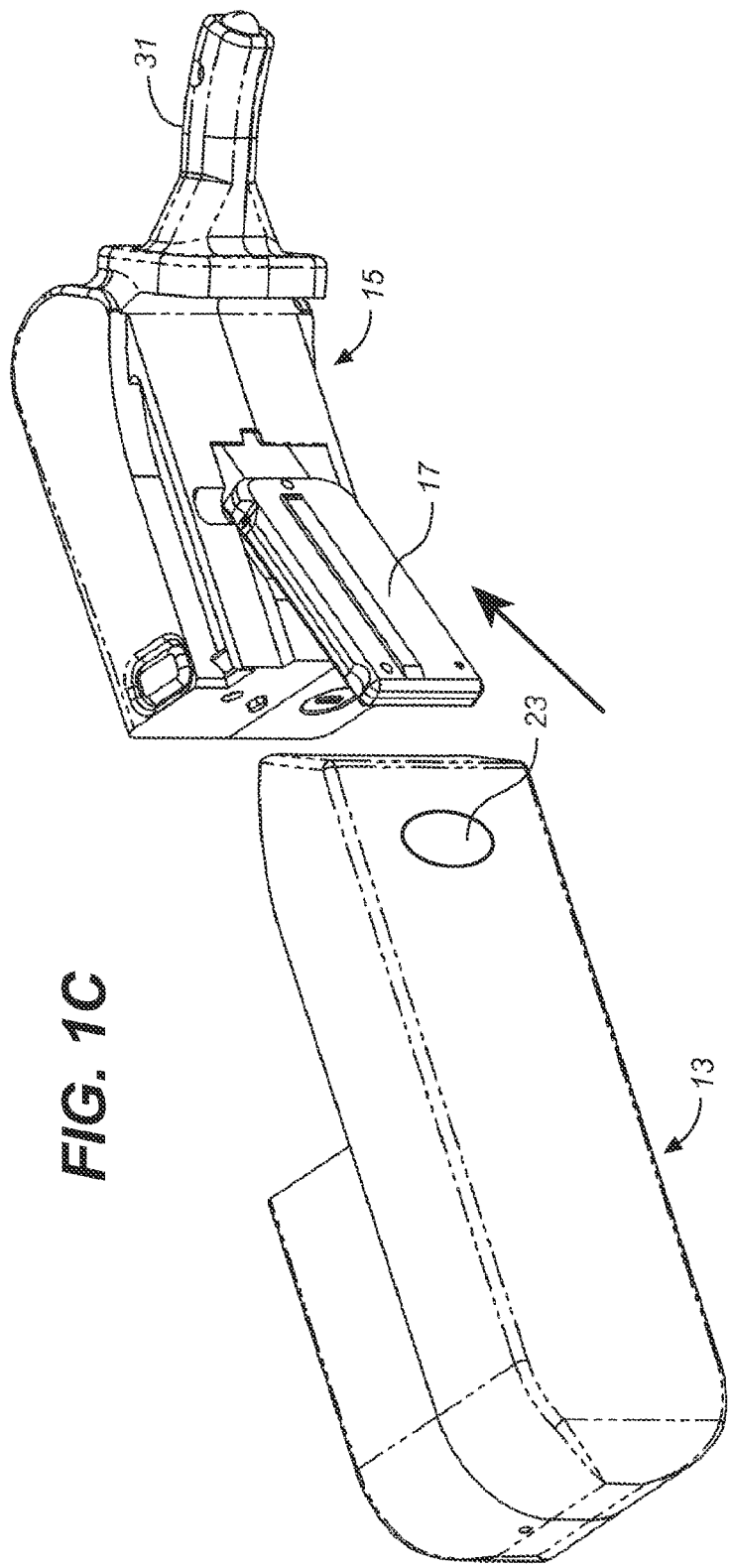

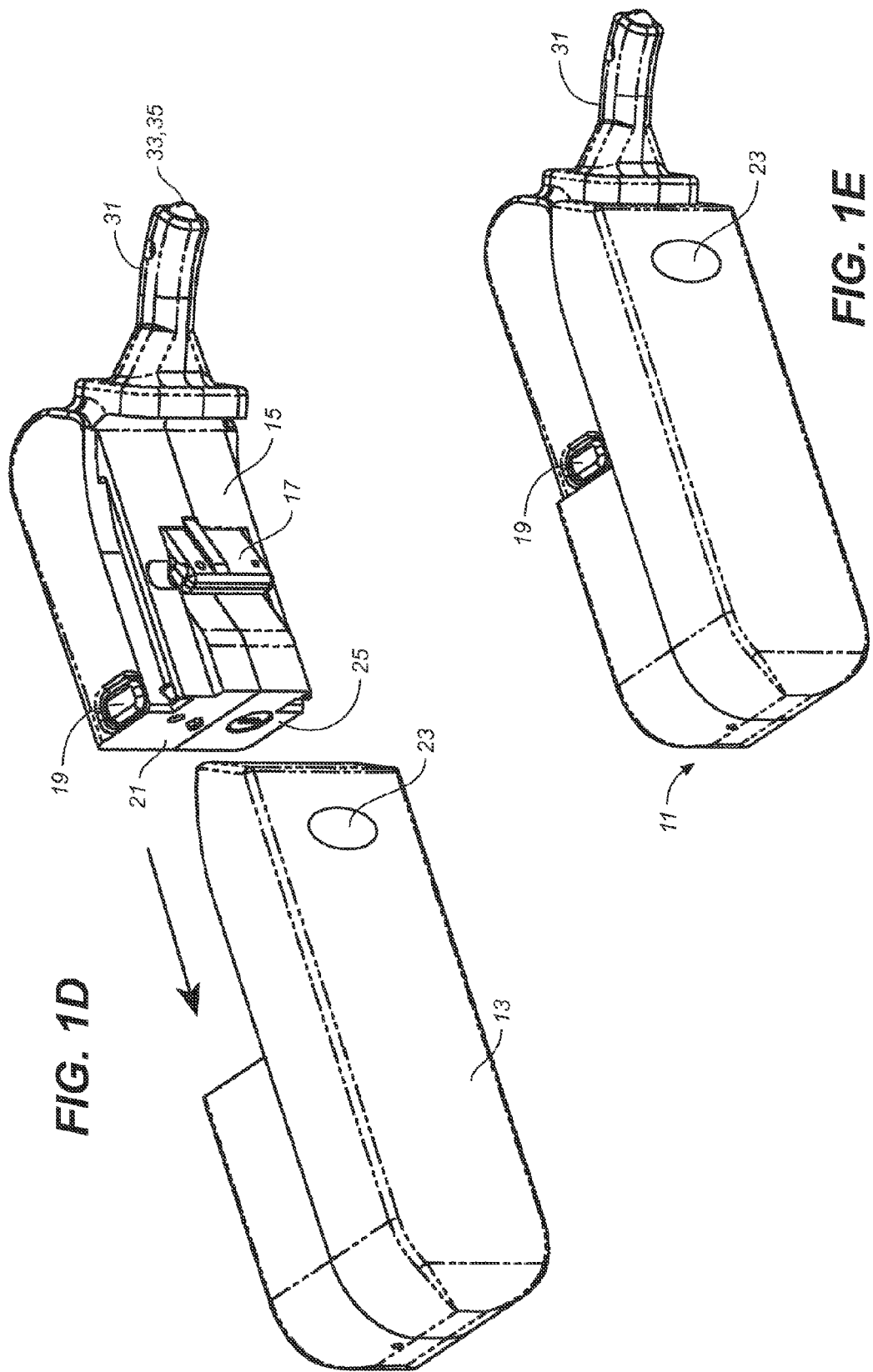

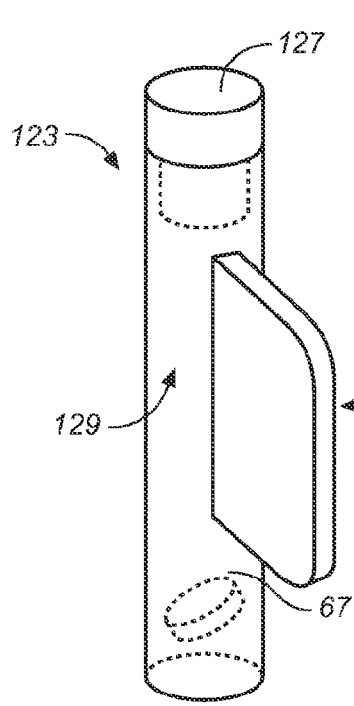
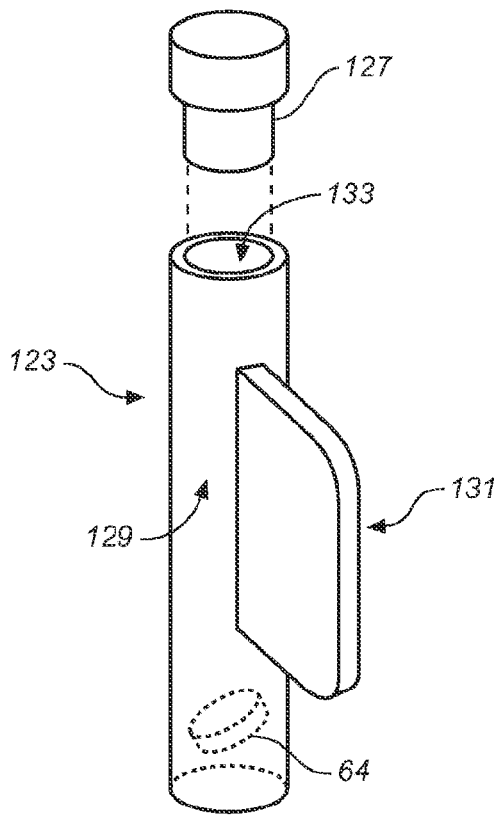
FIG. 15A
FIG. 15B
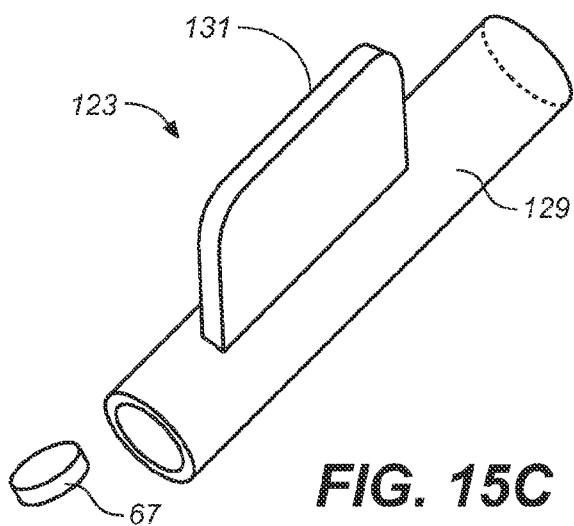
FIG. 15C

METHOD OF MOVING A DELIVERY MEMBER OF A DISPENSING DEVICE FOR ADMINISTRATION OF ORAL TRANSMUCOSAL DOSAGE FORMS

CROSS-REFERENCE TO RELATED APPLICATIONS

This application is a national stage filing under 35 U.S.C. § 371 of International patent application No. PCT/US2007/089017 entitled "Methods for Administering Small Volume Oral Transmucosal Dosage Forms Using a Dispensing Device," filed Dec. 28, 2007, which claims priority to and is a continuation-in-part of U.S. patent application Ser. No. 11/980,216, entitled "Methods for Administering Small Volume Oral Transmucosal Dosage Forms Using a Dispensing Device, filed Oct. 30, 2007, U.S. patent application Ser. No. 11/825,212, entitled "Storage and Dispensing Devices for Administration of Oral Transmucosal Dosage Forms," filed Jul. 3, 2007, U.S. patent application Ser. No. 11/650,174, entitled "Small-Volume Oral Transmucosal Dosage Forms, filed Jan. 5, 2007, now U.S. Patent No. 8,202,535, and U.S. patent application Ser. No. 11/650,230, entitled "Drug Dispensing Device with Flexible Push Rod," filed Jan. 5, 2007, now U.S. Patent No. 8,357,114, each of which is hereby incorporated by reference in their entirety.

FIELD OF THE INVENTION

The invention relates to drug dispensing devices, methods and systems for oral transmucosal administration of small volume drug dosage forms to a subject, wherein the drug dosage forms comprise sufentanil for treatment of pain.

BACKGROUND OF THE INVENTION

Oral dosage forms account for approximately eighty percent of all the drug dosage forms on the market. Oral dosage forms are non-invasive, easily administered and have high patient compliance.

Orally administered therapeutic agents are rapidly transported to the stomach and small intestine for absorption across the gastrointestinal (GI) mucosal membranes into the blood. The efficiency of absorption of a drug following oral administration can be low because of metabolism within the GI tract and first-pass metabolism within the liver resulting in relatively lengthy onset times or erratic absorption characteristics that are not well suited to control acute disorders. The majority of oral dosage forms on the market are designed for GI delivery. Relatively few oral dosage forms are designed for delivery through the oral mucosa.

However, oral transmucosal delivery offers a number of advantages in that it can provide a shorter onset time to maximal plasma concentration ($C_{max}$) than oral delivery, in particular for lipophilic drugs. This is because the drug rapidly passes directly and efficiently through the epithelium of the highly vascularized mucosal tissue to the plasma, thus rapidly reaching the circulation while avoiding the slower, often inefficient and variable GI uptake. It is therefore advantageous for a drug to be delivered through the mucus membranes of the oral cavity, (e.g., via the sublingual route), when rapid onset, consistent $T_{max}$ and $C_{max}$ are advantageous.

In carrying out oral transmucosal drug delivery, the drug is absorbed through the epithelial membranes of the oral cavity. However, frequently the key risk associated with oral transmucosal delivery is the enhanced potential for swallowing the medication owing to the continuous generation, backward flow and swallowing of the saliva. This becomes a particular risk when the used dosage forms are large enough to produce a significant saliva response, which, in turn, leads to swallowing or drug and/or removal of the dosage form from the oral mucosa.

Various solid dosage forms, such as sublingual tablets, troches, lozenges, lozenges-on-a-stick, chewing gums, and buccal patches have been used to deliver drugs via the oral mucosal tissue. Solid dosage forms such as lozenges and tablets have been used for oral transmucosal delivery of drugs, e.g., nitroglycerin sublingual tablets.

The relevant art does not describe a dispensing device for delivery of a drug dosage form to the oral mucosa, such as the sublingual space, where the device facilitates proper placement of the drug dosage form.

Reproducible and effective drug delivery technology represents an area of active research, in particular, as it applies to controlled substances such as opioids. Controlled access oral transmucosal drug dispensing systems offer numerous advantages over conventional means of drug administration such as oral and intravenous routes, the most important of which is enhanced safety, with additional advantages being rapid and consistent onset of action, more consistent and predictable plasma concentrations and higher and more consistent bioavailability than currently available dosage forms.

This is particularly relevant to the treatment of pain, more specifically, acute, intermittent and breakthrough pain.

Therefore, a need exists for a device and system that can be used to administer a controlled substance, such as an opioid (e.g., by patient-controlled administration), for treatment of pain, wherein the device provides for safe and controlled delivery via the oral mucosa, while minimizing the potential for drug abuse and/or diversion.

The present invention addresses these needs.

BRIEF SUMMARY OF THE INVENTION

The invention provides drug dispensing devices, methods, systems and kits for oral transmucosal, e.g., sublingual administration of a bioadhesive small volume sufentanil-containing drug dosage form to a subject using a device.

The device may be hand-held and portable and comprises a cartridge containing one or more drug dosage forms (typically from 1 to about 200) dosage forms.

Each dosage form comprises 5 mcg, 10 mcg, 15 mcg, 20 mcg, 30 mcg, 40 mcg, 50 mcg, 60 mcg, 70 mcg, 80 mcg or 100 mcg of sufentanil and has a volume of less than 100 microliters or a mass of less than 100 mg.

In using the device, the dispensing end of the device is inserted into the mouth of the subject and a dosage form is dispensed through the dispensing end of the device such that it is placed on an oral mucosal membrane (e.g., in the sublingual space) of the subject.

The dispensing end of the device has a proboscis comprising a shroud for placing the dosage form and the shroud includes a means to prevent or retard saliva and other moisture ingress into the device, such that the dosage forms remain dry prior to placement on the oral mucosal membrane.

The device further comprises a lock-out feature for setting a lock-out time wherein a dosage form cannot be dispensed from the device during the lock-out time. The lock-out time may be a fixed time lock-out interval, a predetermined lock-out interval, a predetermined variable lock-out interval, a lock-out interval determined by an algorithm or a variable lock-out interval communicated to the device from a remote computer, docking station or other device.

The cartridge may comprise one or more shipping tablets wherein at least one shipping tablet is dispensed prior to dispensing of a dosage form.

The cartridge may include a smart cartridge recognition system comprising a physical keyed feature on the cartridge, an optically detected feature or pattern, a bar code on the cartridge, a magnetic tag on the cartridge, an RFID tag on the cartridge, an electronic microchip on the cartridge, or a combination thereof.

The dispensing device further comprises a user identification means wherein the user identification means is a radio frequency identification (RFID) reader configured to couple with a matching RFID tag on a patient to be identified and the dispensing device is unlocked or enabled when the RFID reader on the dispensing device detects a matching RFID tag on a patient.

The dispensing device may also comprise a means for recording dosing, use history, or both, alone or in combination with a means to view or download the dosing and/or use history.

Following placement of a dosage from on an oral mucosal membrane of the subject, erosion of the dosage form is complete in from about 30 seconds to about 30 minutes.

In carrying out the method, a single sublingual administration of a dosage form to a subject results in a bioavailability of at least 50%, an AUC with a coefficient of variation of less than 40%, a $T_{max}$ with a coefficient of variation of less than 40%; repeated sublingual administrations of a dosage form to a subject results in a bioavailability that is greater than the bioavailability following a single sublingual administration to the subject and the $T_{max}$ following repeated sublingual administration and the time of the previous sublingual administration is shorter than the $T_{max}$ following a single sublingual administration to the subject.

When a bioadhesive small volume sufentanil-containing drug dosage form is administered to the sublingual cavity of subject using a device, an amount of drug selected from the group consisting of at least 55%, at least 60%, at least 65%, at least 70%, at least 75%, at least 80%, at least 85%, at least 90%, at least 95%, at least 98% and at least 99% of the total amount of drug in the dosage form is absorbed via the sublingual route.

Administration of a sufentanil-containing drug dosage form using a drug dispensing device may be patient controlled and may be used for treating pain in a subject, wherein following administration of the dosage form, pain relief is evident.

BRIEF DESCRIPTION OF THE DRAWINGS

FIGS. 1A-E provide a schematic depiction of an exemplary dispensing device wherein the device is designed to deliver drug dosage forms to oral mucosa of a patient under treatment.

FIGS. 5A-D provide a series of flow diagrams for use of an exemplary device showing the stages of push rod/tablet interaction during device use, wherein FIG. 5A shows the LOAD feature; FIG. 5B shows the CALIBRATE feature; FIG. 5C shows the DISPENSE feature; and FIG. 5D shows the DISASSEMBLE feature.

FIGS. 15A-C provide an illustration of one type of single dose applicator and use thereof in delivering a dosage form to a subject.

DETAILED DESCRIPTION

I. Introduction

Provided herein are compositions, methods, systems and kits for oral transmucosal administration of opioid-containing small volume dosage forms using a device. Oral transmucosal delivery of the dosage forms minimizes the saliva response and therefore minimizes delivery of the drug to the GI tract, such that the majority of drug is delivered across the oral mucosa. The small volume dosage forms have bioadhesive properties which facilitate adherence to the oral mucosa, thus minimizing the risk of ingestion and inefficient delivery due to swallowing.

Figure 22:
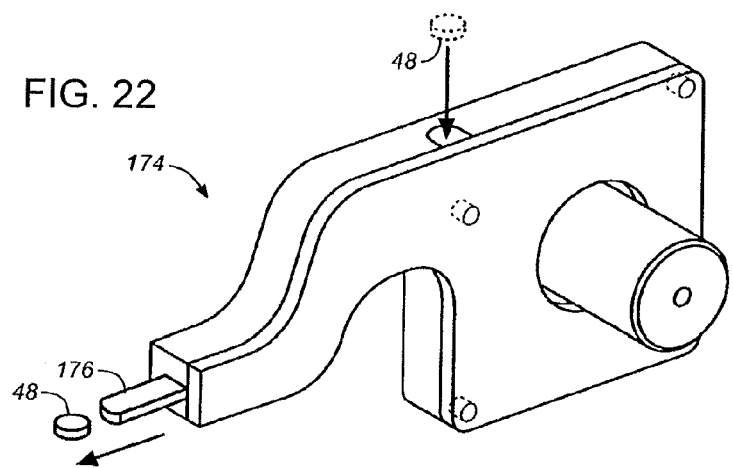
Figure 23:
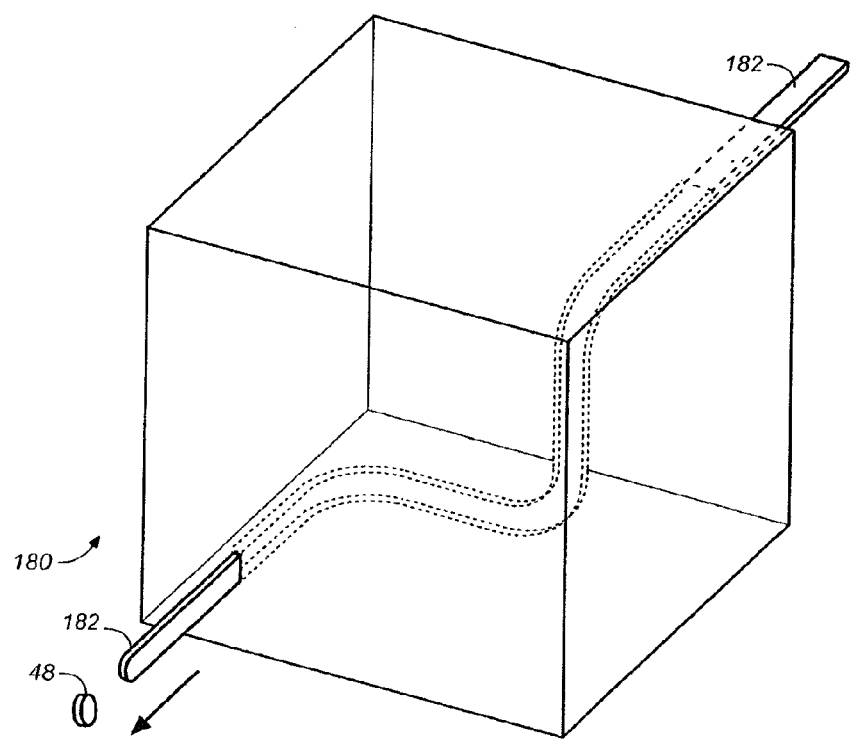

FIGS. 22 and 23 depict additional exemplary pushrod dispensing devices of the invention for dispensing a drug dosage form, wherein the pushrods are designed to be flexible and to afford different geometry.

The following disclosure describes the dosage forms, devices, methods, systems and kits which constitute the invention. The invention is not limited to the specific dosage forms, devices, methodology, systems, kits or medical conditions described herein, as such may, of course, vary. It is also to be understood that the terminology used herein is for the purpose of describing particular embodiments only, and is not intended to limit the scope of the present invention.

It must be noted that as used herein and in the appended claims, the singular forms "a", "and", and "the" include plural references unless the context clearly dictates otherwise. Thus, for example, reference to "a drug formulation" includes a plurality of such formulations and reference to "a drug delivery device" includes systems comprising drug dosage forms and delivery device devices for containment, storage and delivery of such dosage forms.

Unless defined otherwise, all technical and scientific terms used herein generally have the same meaning as commonly understood to one of ordinary skill in the art to which this invention belongs. Although any methods, devices and materials similar or equivalent to those described herein can be used in the practice or testing of the invention, the preferred methods, devices and materials are now described.

The publications discussed herein are provided solely for their disclosure prior to the filing date of the present application. Nothing herein is to be construed as an admission that the invention is not entitled to antedate such a disclosure by virtue of prior invention.

II. Definitions

The term "active agent" or "active" may be used interchangeably herein with the term "drug" and is meant to refer to any therapeutically active agent.

The term "adhere" is used herein with reference to a drug dosage form or formulation that is in contact with a surface such as a mucosal surface and is retained on the surface without the application of an external force. The term "adhere" is not meant to imply any particular degree of sticking or bonding, nor is it meant to imply any degree of permanency.

The term "analgesic drug" as used herein includes sufentanil or a sufentanil congener, such as alfentanil, fentanyl, lofentanil, carfentanil, remifentanil, trefentanil, or mirfentanil, as well as formulations comprising one or more therapeutic compounds. Use of the phrase "sufentanil or a congener" is not meant to be limiting to use of, or formulations comprising, only one of these selected opioid compounds. Furthermore, reference to sufentanil alone or to a selected sufentanil congener alone, e.g., reference to "alfentanil", is understood to be only exemplary of the drugs suitable for delivery according to the methods of the invention, and is not meant to be limiting in any way.

The term "AUC" as used herein means "area under the curve" in a plot of concentration of drug in plasma versus time. AUC is usually given for the time interval zero to infinity, however, clearly plasma drug concentrations cannot be measured 'to infinity' for a patient so mathematical approaches are used to estimate the AUC from a limited number of concentration measurements. In a practical sense, the AUC (from zero to infinity) represents the total amount of drug absorbed by the body, irrespective of the rate of absorption. This is useful when trying to determine whether two formulations of the same dose release the same dose of drug to the body. The AUC of a transmucosal dosage form compared to that of the same dosage administered intravenously serves as the basis for a measurement of bioavailability.

The term "bioadhesion" as used herein refers to adhesion to a biological surface including mucosal membranes.

The term "bioavailability" or "F" as used herein means "percent bioavailability" and represents the fraction of drug absorbed from a test article as compared to the same drug when administered intravenously. It is calculated from the $AUC_\infty$ of the test article following delivery via the intended route versus the $AUC_\infty$ for the same drug after intravenous administration. It is calculated from the equation: Bioavailability (%)=$AUC_\infty$(test article)/$AUC_\infty$(intravenous route/article).

The term "breakthrough pain" as used herein, is a transitory flare of pain of moderate to severe intensity occurring on a background of otherwise controlled pain. "Breakthrough pain" can be intense for short periods of time, as short as 1 or 2 minutes or as long as 30 minutes or more.

The term "cartridge" is used herein with reference to a replaceable, single use disposable cartridge configured to hold one or more drug dosage forms, typically, up to 200 drug dosage forms. The cartridge typically comprises a smart cartridge recognition system with a physical keyed feature on the cartridge, a bar code on the cartridge, a magnetic tag on the cartridge, an RFID tag on the cartridge, an electronic microchip on the cartridge, or a combination thereof. The cartridge may comprise one or more shipping tablets wherein at least one shipping tablet is dispensed prior to dispensing of a dosage form.

The term "$C_{max}$" as used herein means the maximum observed plasma concentration following administration of a drug.

The term "congener" as used herein refers to one of many variants or configurations of a common chemical structure.

The term "disintegration" is used interchangeably herein with "erosion" and means the physical process by which a dosage form breaks down and pertains to the physical integrity of the dosage form alone. This can occur in a number of different ways including breaking into smaller pieces and ultimately, fine and large particulates or, alternatively, eroding from the outside in, until the dosage form has disappeared.

The term "dissolution" as used herein means the process by which the active ingredient is dissolved from the tablet in the presence of a solvent, in vitro, or physiological fluids in vivo, e.g., saliva, irrespective of the mechanism of release, diffusion, erosion or combined erosion and diffusion.

The term "dispensing device", "drug dispensing device", "dispenser", "drug dispenser", "drug dosage dispenser", "device" and "drug delivery device" are used interchangeably herein and refer to a device that dispenses a drug dosage form. The dispensing device provides for controlled and safe delivery of a pharmaceutically active substance (e.g., an opioid such as sufentanil) formulated in the dosage form. The device may be adapted for storage and/or delivery of a dosage form such as a lozenge, pill, tablet, capsule, membrane, strip, liquid, patch, film, gel, spray or other form.

The term "dispensing end" as used herein with reference to a device means the portion of the device comprising the proboscis and shroud which serves to deliver a drug dosage form to the oral mucosa of a subject.

The term "drug", "medication", "pharmacologically active agent", "therapeutic agent" and the like are used interchangeably herein and generally refer to any substance that alters the physiology of an animal and can be effectively administered by the oral transmucosal route.

The term "erosion time" means the time required for a solid dosage form to break down until the dosage form has disappeared.

The term "FOB" refers to a small, portable handheld, powered electronic docking device that can be used in conjunction with the drug dispensing device to upload data, download data, control access to the drug dispensing device, control access to the drug dosage forms, or enhance or otherwise alter the user interface of the drug dispensing device. A FOB may communicate and dock with a drug dispensing device either in a wired or wireless fashion. A FOB may be adapted to attach to a cord so as to allow the FOB to hang from the neck of a healthcare professional such as a physician or caregiver, particularly in the hospital setting. A drug dispensing device may communicate with the physician or care giver via the FOB.

The terms "formulation" and "drug formulation" as used herein refer to a physical composition containing at least one pharmaceutically active substance, which may be provided in any of a number of dosage forms for delivery to a subject. The dosage form may be provided to the patient as a lozenge, pill, capsule, membrane, strip, liquid, patch, film, gum, gel, spray or other form.

The term "hydrogel-forming preparation", means a solid formulation largely devoid of water which upon contact with an aqueous solution, e.g., a bodily fluid, and in particular that of the oral mucosa, absorbs water in such a way that it forms a hydrated gel in situ. The formation of the gel follows unique disintegration (or erosion) kinetics while allowing for release of the therapeutic agent over time. Additionally, the term "hydrogel-forming preparation" describes a solid formulation largely devoid of water which upon contact with bodily fluids, and in particular those in the oral cavity, transforms into a film that releases the drug. Such films increase the surface area available for drug release and absorption thus enabling faster absorption of the drug.

The term "lock-out feature" is used herein with reference to a feature of the device which provides for a "lock-out time".

The term "lock-out time" is used herein with reference to the period of time during which the device does not allow drug accessibility, i.e., a dosage form cannot be dispensed during the "lock-out time". "Lock-out time" may be programmable, a fixed time interval, a predetermined interval, a predetermined variable interval, an interval determined by an algorithm or a variable interval communicated to the device from a remote computer or docking station.

The term "LogP" as used herein means logarithm of the ratio of equilibrium concentrations of un-ionized compound between octanol and water. P also called the "octanol-water partition coefficient" and serves as a means to quantify the hydrophobicity or lipophilicity of, a chemical characteristic of a given drug.

The term "mucoadhesion" is used herein in to refer to the adhesion to mucosal membranes which are covered by mucus, such as those in the oral cavity and may be used interchangeably herein with the term "bioadhesion" which refers to adhesion to any biological surface.

The term "mucosal membrane" refers generally to any of the mucus-coated biological membranes in the body. Absorption through the mucosal membranes of the oral cavity is of particular interest. Thus, oral mucosal absorption, i.e., buccal, sublingual, gingival and palatal absorption are specifically contemplated.

The term "mucosal-depot" is used herein in its broadest sense to refer to a reservoir or deposit of a pharmaceutically active substance within or just beneath the mucosal membrane.

The term "non-ordered particulate mixture" or "non-ordered mixture" is used herein with reference to a formulation where the mixture is not ordered with respect to the pharmaceutically active agent and the bioadhesive material or bioadhesion promoting agent, or other formulation components. In addition, it is used herein with reference to any formulation prepared by a process that involves dry mixing wherein drug particles are not uniformly distributed over the surface of larger carrier particles. Such 'non-ordered' mixing may involve dry mixing of particles in a non-ordered fashion, where there is no requirement with respect to the order of addition/mixing of specific excipients with the drug, bioadhesive material or bioadhesion promoting agent and/or disintegrants. Further in the non-ordered mixing process, there is no limitation on the size of the drug particles. The drug particles may be larger than 25 μm. In addition, a "non-ordered mixture" includes any mixing processes in which the primary carrier particles do not incorporate a disintegrant within. Finally the "non-ordered mixture" may be prepared by any 'wet mixing' processes, i.e. processes in which a solvent or non-solvent is added during the mixing process or any mixing process in which the drug is added in a solution or suspension form.

The term "operatively connected" as used herein means the components are provided in a device so as to function as intended to achieve an aim. For example, a memory device operatively connected to a CPU which is further operatively connected to a release mechanism may be meant to indicate that, upon actuation, the CPU communicates with the memory device to check the status or history of drug delivery, and then further communicates with the release mechanism (e.g., via a solenoid and a switch) to release and dispense a drug.

The terms "oral transmucosal dosage form" and "drug dosage form" may be used interchangeably herein and refer to a dosage form which comprises a pharmaceutically active substance, e.g., a drug such as sufentanil. The oral dosage form is used to deliver the pharmaceutically active substance to the circulation by way of the oral mucosa and is typically a "sublingual dosage form", but in some cases other oral transmucosal routes may be employed. The dosage form provides for delivery of the pharmaceutically active substance across the oral mucosa and not via swallowing followed by GI absorption, by controlling the formulation the timing for release of the pharmaceutically active substance can be achieved. The dosage form comprises pharmaceutically acceptable excipients and may be referred to as a NanoTab™, as detailed in U.S. application Ser. No. 11/650,174. The dosage form comprises a formulation that is neither effervescent nor does it comprise an essentially water-free, ordered mixture of microparticles of drug adhered to the surface of carrier particles, where the carrier particles are substantially larger than the microparticles of drug.

The terms "oral transmucosal drug delivery" and "oral transmucosal administration" as used herein refer to drug delivery that occurs substantially via the oral transmucosal route and not via swallowing followed by GI absorption. This includes delivery via buccal, sublingual and gum transmucosal areas.

The term "proboscis" is used interchangeably with the terms "dispensing tip" a "delivery tip", and refers to a dispensing and/or positioning tip of a drug dosage form dispenser that delivers a dosage form to the oral mucosa (e.g., the sublingual space).

The term "radio frequency identification device" or "RFID" is used with reference to an automatic identification method, which relies on storing and remotely retrieving data using devices called RFID tags, wherein the RFID tag is applied to, or incorporated into a product, or person for the purpose of identification using radiowaves. Some tags can be read from several meters away and beyond the line of sight of the reader.

The term "replaceable cartridge" or "disposable cartridge" is used with reference to a cartridge for housing drug dosage forms which is typically configured to hold up to 200 drug dosage forms, wherein the cartridge is designed to be used and discarded.

The term "shipping tablet" is used herein with reference to an "initialization", or "shipping" tablet which is the same size and shape as a drug-containing dosage form but does not contain a pharmaceutically active substance. The "shipping tablet" may comprise a placebo dosage form that does not contain a pharmaceutically active substance or may be made of plastic or other material. It is the first thing dispensed from a new cartridge after insertion into a dispensing device. The device has a means for differentiating between the shipping tablet and a dosage form containing a pharmaceutically active substance.

The term "shroud" is used to describe a partial or complete covering of the dispensing end of the device which protects the delivery port from contact with saliva or other moisture in the oral cavity and forms a barrier between the device, the oral mucosa and tongue, has a relief for dosage form delivery, and an interior that is hydrophobic or hydrophilic which serves to minimize or eliminate saliva ingress or moisture ingress. The "shroud" creates a barrier from the oral mucosa contacting the valve area and dosage form, aiding in dosage form dispensing and discouraging dosage form adherence to the shroud. The shroud may have a rounded interior surface or other geometry to stop the dosage form adhering to the shroud. The shroud limits the ability of the tongue or oral mucosa to contact the dosage form dispensing area, thereby controlling saliva contact and ingress. The shroud shields the valve from moisture and saliva ingress from the tongue and other mucosa and provides an area for the dosage form to exit the device without "sticking" to the wetted distal valve or shroud area. The shroud also comprises a cut-out/relief in order to mitigate the dragging of dosage forms when the device is removed from the oral space. The valve functions with the shroud to control saliva and moisture ingress, as well as aid in delivery of the dosage form.

The term "subject" includes any subject, generally a mammal (e.g., human, canine, feline, equine, bovine, ungulate etc.), adult or child, in which treatment for a disorder is desired. The terms "subject" and "patient" may be used interchangeably herein.

The term "systems that include a drug dosage form and a dispensing device" as used herein refers to a drug dispensing system for delivery and/or monitoring of drug administration. The system may be used to monitor and deliver a pharmaceutically active substance, e.g., an opioid such as sufentanil, wherein the amount of drug delivered, corresponding efficacy and safety are enhanced over currently available systems. The system may have one or more features that provide for improved safety and ease of use over currently available systems including a security feature that prevents unauthorized access to the stored drugs, a dosing lock-out feature, a means for identifying an individual user for controlled drug access, a dose counting feature, a memory means for retaining information about dose delivery, and an interface for bidirectional exchange of information with a user, a drug cartridge, or another device such as a computer.

The term "small volume drug dosage form" or "small volume dosage form" is used herein with reference to a small volume dosage form that has a volume of less than 100 µl and a mass of less than 100 mg. More specifically, the dosage form has a mass of less than 100 mg, 90 mg, 80 mg, 170 mg, 60 mg, 50 mg, 40 mg, 30 mg, 29 mg, 28 mg, 27 mg, 26 mg, 25 mg, 24 mg, 23 mg, 22 mg, 21 mg, 20 mg, 19 mg, 18 mg, 17 mg, 16 mg, 15 mg, 14 mg, 13 mg, 12 mg, 11 mg, 10 mg, 9 mg, 8 mg, 7 mg, 6 mg or 5 mg or a volume of less than 100 µl, 90 µl, 80 µl, 70 µl, 60 µl, 50 µl, 40 µl, 30 µl, 29 mg, 28 mg, 27 µl, 26 µl, 25 µl, 24 µl, 23 µl, 22 µl, 21 µl, 20 µl, 19 µl, 18 µl, 17 µl, 16 µl, 15 µl, 14 µl, 13 µl, 12 µl, 11 µl, 10 µl, 9 µl, 8 µl, 7 µl, 6 µl or 5 µl. The "dosage form" may or may not have bioadhesive characteristics and may form a hydrogel upon contact with an aqueous solution.

The "dosage form" may be used to deliver any drug that can be administered by the oral transmucosal route in an amount amenable to administration via the small size of the dosage form, i.e. 0.25 µg to 99.9 mg, 1 µg to 50 mg or 1 µg to 10 mg.

The term "small volume sufentanil-containing drug dosage form" is used herein with reference to a small volume dosage form that contains a dose of sufentanil selected from about 2 micrograms (mcg) to about 200 mcg of sufentanil, e.g., 5 mcg, 10 mcg, 15 mcg, 20 mcg, 30 mcg, 40 mcg, 50 mcg, 60 mcg, 70 mcg, 80 mcg or 100 mcg of sufentanil.

The term "solid dosage form" or "solid drug dosage form" is used herein with reference to a small volume dosage form that is a solid, e.g., a lozenge, a pill, a tablet, a membrane or a strip.

The term "sublingual", means literally "under the tongue" and refers to administering a drug dosage form via the mouth in such a way that the pharmaceutically active substance is rapidly absorbed via the blood vessels under the tongue rather than via the digestive tract. Absorption occurs via the highly vascularized sublingual mucosa and allows the pharmaceutically active substance more direct access to the blood circulation, providing for direct systemic administration independent of GI influences.

The term "Therapeutic Time Ratio" or "TTR" presents the average time that the drug is present at therapeutic levels, defined as time within which the drug plasma concentration is maintained above 50% of $C_{max}$ normalized by the drug's elimination half-life and it is calculated by the formula: TTR= (Time above 50% of $C_{max}$)/(Terminal intravenous elimination half-life of the drug). The last term is obtained from literature data for the drug of interest in the appropriate species.

The term "$T_{max}$" as used herein means the time point of maximum observed plasma concentration.

The term "$T_{onset}$" as used herein means the observed "time of onset" and represents the time required for the plasma drug concentration to reach 50% of the maximum observed plasma concentration, $C_{max}$.

The term "therapeutically effective amount" means an amount of a therapeutic agent, or a rate of delivery of a therapeutic agent (e.g., amount over time), effective to facilitate a desired therapeutic effect, such as pain relief. The precise desired therapeutic effect (e.g., the degree of pain relief, and source of the pain relieved, etc.) will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

III. Drug Dosage Forms

The claimed small volume oral transmucosal drug dosage forms produce a reduced saliva response as compared with conventional, larger dosage forms that are intended to deliver a drug in the oral cavity. The dosage forms contain a pharmaceutically active substance and provide for high absorption rates of the pharmaceutically active substance across the oral mucosa and reduced uptake via the gastrointestinal tract, thereby offering a more consistent and reproducible pharmacokinetic and corresponding pharmacodynamic profile.

The dosage forms are typically a "sublingual dosage form", but in some cases other oral transmucosal routes may be employed. The dosage form is a substantially homogeneous composition which comprises one or more active drugs together with pharmaceutically acceptable excipients.

The preferred site for oral transmucosal drug delivery is the sublingual space, although in certain embodiments it may be advantageous for the dosage form to be placed inside the cheek, or to adhere to the roof of the mouth or the gum.

The dosage forms provide for the delivery of a greater percentage (and amount) of the drug via the oral mucosa and a corresponding decrease in delivery via the gastrointestinal (GI) tract as compared to traditional oral dosage forms and other oral transmucosal dosage forms.

Typically, the dosage forms are generally adapted to adhere to the oral mucosa (i.e. are bioadhesive) during the period of drug delivery, and until most or all of the drug has been delivered from the dosage form to the oral mucosa.

The claimed dosage forms have a mass of less than 100 mg and a volume of less than 100 ul. More specifically, the dosage forms have a mass of less than 100 mg, 90 mg, 80 mg, 170 mg, 60 mg, 50 mg, 40 mg, 30 mg, 29 mg, 28 mg, 27 mg, 26 mg, 25 mg, 24 mg, 23 mg, 22 mg, 21 mg, 20 mg, 19 mg, 18 mg, 17 mg, 16 mg, 15 mg, 14 mg, 13 mg, 12 mg, 11 mg, 10 mg, 9 mg, 8 mg, 7 mg, 6 mg or 5 mg or a volume of less than 100 µl, 90 µl, 80 µl, 70 µl, 60 µl, 50 µl, 40 µl, 30 µl, 29 mg, 28 mg, 27 µl, 26 µl, 25 µl, 24 µl, 23 µl, 22 µl, 21 µl, 20 µl, 19 µl, 18 µl, 17 µl, 16 µl, 15 µl, 14 µl, 13 µl, 12 µl, 11 µl, 10 µl, 9 µl, 8 µl, 7 µl, 6 µl or 5 µl. The dosage forms typically have bioadhesive characteristics and may form a hydrogel upon contact with an aqueous solution.

The dosage forms typically have an erosion time of from 30 seconds up to 5 minutes, up to 10 minutes, up to 15 minutes or up to 30 minutes.

In general, at least 55%, at least 60%, at least 65%, at least 70%, at least 75%, at least 80%, at least 85%, at least 90%, at least 95%, at least 98% or at least 99% of the total amount of pharmaceutically active substance in a dosage form administered to the oral mucosa of a subject is absorbed via the oral transmucosal route.

The dosage forms may have essentially any shape, examples of which include a round disc with a flat, concave, or convex face, an ellipsoid shape, a spherical shape, a polygon with three or more edges and flat, concave, or convex faces. The dosage forms may be symmetrical or asymmetrical, and may have features or geometries that allow for controlled, convenient, and easy storage, handling, packaging or dosing.

Oral transmucosal drug delivery is simple, non-invasive, and can be administered by a caregiver or patient with minimal discomfort. A dosage form for oral transmucosal delivery may be solid or non-solid. In one preferred embodiment, the dosage from is a solid that turns into a hydrogel following contact with saliva. In another preferred embodiment, the dosage from is a solid that erodes without forming a hydrogel following contact with saliva.

Generally, oral transmucosal delivery of pharmaceutically active substances is achieved using solid dosage forms such as lozenges or tablets, however, liquids, sprays, gels, gums, powders, and films and the like may also be used.

For certain drugs, such as those with poor bioavailability via the GI tract, e.g., lipophilic opioids such as sufentanil and alfentanil, oral transmucosal delivery is a more effective delivery route than GI delivery. For such lipophilic drugs, oral transmucosal delivery has a shorter onset time (i.e., the time from administration to therapeutic effect) than does oral GI delivery and provides better bioavailability and more consistent pharmacokinetics.

The claimed drug dosage forms are designed and adapted to reduce the saliva response, thus reducing the amount of drug swallowed, and thereby delivering a substantial amount of drug to a subject via the oral mucosa. The claimed drug dosage forms also provide efficacious delivery of drug via the oral mucosa and a consistent plasma level within the therapeutic window.

The claimed dosage forms comprise substantially homogeneous formulations which include at least 0.001% percent by weight of the pharmaceutically active substance in combination with pharmaceutically acceptable excipients. Typically the claimed dosage forms comprise from 0.01-99% or from about 0.25 µg to 99.9 mg, from about 1 µg to 50 mg or from about 1 µg to 10 mg w/w of the pharmaceutically active substance.

Formulations for preparation of the claimed dosage forms and methods of making them are described in U.S. application Ser. Nos. 11/825,251 and 11/650,227. An exemplary formulation is bioadhesive and comprises from about 0.0004% to about 0.04% sufentanil, e.g., 0.0005%, 0.001%, 0.002%, 0.003%, 0.004%, 0.006%, 0.008%, 0.01%, 0.012%, 0.014% or 0.016% sufentanil. In general, the formulation comprises (a) a non-ordered mixture of a pharmaceutically active amount of a drug; (b) a bioadhesive material which provides for adherence to the oral mucosa of the subject; and (c) stearic acid, wherein dissolution of a dosage form comprising the formulation is independent of pH, e.g., over a pH range of about 4 to 8.

Pharmaceutically active agents for use in a formulation of the invention are characterized by logarithm of the octanol-water partition coefficient (LogP) between 0.006 and 3.382.

A pharmaceutical dosage form of the invention for oral transmucosal delivery may be solid or non-solid. In one preferred embodiment, the dosage from is a solid that transforms into a hydrogel following contact with saliva. In another preferred embodiment, the dosage form is a solid that transforms into a bioadhesive film upon contact with saliva.

In a preferred embodiment, such formulations are designed to form a film which is visible following tablet disintegration. Upon placement on the oral mucosa, the dosage form absorbs water such that upon full hydration, it spreads across the mucosal surface, thus transforming into a bioadhesive film containing the active drug. This transformation results in a significant increase of the surface area available for drug release, thus accelerating drug diffusion and release from the dosage form. Owing to the higher contact surface area, drug absorption occurs fast, resulting in fast onset of action.

Numerous suitable nontoxic pharmaceutically acceptable carriers for use in oral dosage forms can be found in Remington's Pharmaceutical Sciences, 17th Edition, 1985.

It will be understood that the formulation is converted into a dosage form for delivery to a subject using procedures routinely employed by those of skill in the art, such as direct compression, wet granulation, etc. The process for preparation of the dosage form is optimized for each formulation in order to achieve high dose content uniformity.

While not wishing to be bound by theory, in one exemplary embodiment, when a drug dosage form is placed in the sublingual cavity, preferably under the tongue on either side of the frenulum linguae, it adheres upon contact. As the dosage form is exposed to the moisture of the sublingual space the dosage form absorbs water, resulting in erosion of the dosage form and release of the active drug to the circulation of the subject.

IV. Sufentanil

Opioids are widely used for the treatment of pain, and are generally delivered intravenously, orally, epidurally, transdermally, rectally and intramuscularly. Morphine and its analogues are commonly delivered intravenously and are effective against severe, chronic and acute pain. However, they can also have severe respiratory depressive effects if not used appropriately and also suffer from a high abuse potential. The predominant cause of morbidity and mortality from pure opioid overdoses is due to respiratory complications.

One exemplary use of the claimed drug dosage forms is with application to pain-relief. When the claimed drug dosage forms are used for treatment of pain, they comprise a drug such as an opioid or opioid agonist and are utilized to treat both acute and chronic pain of moderate to severe intensity.

The active agent in such drug dosage forms is sufentanil or a sufentanil congener such as alfentanil, fentanyl, lofentanil, carfentanil, remifentanil, trefentanil, or mirfentanil. In a preferred embodiment, sufentanil is the active agent. Sufentanil may be provided as sufentanil citrate, sufentanil base, or a combination thereof.

Another preferred embodiment relies on a sufentanil congener as the active agent. Yet another preferred embodiment relies on a combination of sufentanil and at least one additional agent for treatment of analgesia as the active agent, e.g., a combination of sufentanil and alfentanil. Various opioid drugs have different pharmacokinetic profiles and different interactions with mu opioid receptor splice variants and, therefore, may be used in combination to enhance the therapeutic effect.

Sufentanil (N-[(4-(Methoxymethyl-1-(2-(2-thienyl) ethyl)-4-piperidinyl)]-N-phenylpropanamide), is used as a primary anesthetic, to produce balanced general anesthesia in cardiac surgery, for epidural administration during labor and delivery and has been administered experimentally in both intranasal and liquid oral formulations. A commercial form of sufentanil used for IV delivery is the SUFENTA FORTE® formulation. This liquid formulation contains 0.075 mg/ml sufentanil citrate (equivalent to 0.05 mg of sufentanil base) and 9.0 mg/ml sodium chloride in water. It has a plasma elimination half-life of 148 minutes, and 80% of the administered dose is excreted in 24 hours.

Following transbuccal administration of fentanyl using a lozenge (e.g., Actiq®), the bioavailability is 50%, although the $T_{max}$ for the 200 mcg dosage of Actiq® ranges from 20-120 minutes resulting from erratic GI uptake due to the fact that 75% of the fentanyl is swallowed (Actiq® package insert). More recent publications on the $T_{max}$ of Actiq indicate that these original times were skewed towards more rapid onset (Fentora package insert indicates a range of $T_{max}$ for Actiq extending up to 240 minutes). Fentora (a fentanyl buccal tablet) exhibits a bioavailability of 65%, with reported swallowing of 50% of the drug. In contrast to the claimed dosage forms, both Actiq® and Fentora suffer from the disadvantage that substantial amounts of lozenge-administered fentanyl are swallowed by the patient.

Although sufentanil and fentanyl have many similarities as potent muopioid receptor agonists, they have been shown to differ in many key ways. Multiple studies have demonstrated sufentanil to be in the range of 7-24 times more potent than fentanyl (SUFENTA® package insert; Paix A, et al. Pain, 63:263-69, 1995; Reynolds L, et al., Pain, 110:182-188, 2004). Therefore, sufentanil may be administered using a smaller dosage form, avoiding the increased saliva response of a larger dosage form and thereby minimizing the amount of drug that is swallowed. This leads to minimal GI uptake.

In addition, fentanyl and other opiate agonists, have the potential for deleterious side effects including respiratory depression, nausea, vomiting and constipation. Since fentanyl has a 30% bioavailability from the GI route, this swallowed drug can contribute to the $C_{max}$ plasma levels to a significant degree and results in the erratic $C_{max}$ and $T_{max}$ observed with these products.

Further, the lipid solubility (octanol-water partition coefficient) of sufentanil (1778:1) is greater than fentanyl (816:1). Sufentanil also displays increased protein binding (91-93%) compared with fentanyl (80-85%) (SUFENTA® and Actiq® package inserts, respectively). Sufentanil has a pKa of 8.01, whereas the pKa of fentanyl is 8.43 (Paradis et al., Therapeutic Drug Monitoring, 24:768-74, 2002). These differences can affect various pharmacokinetic parameters, for example, sufentanil has been shown to have a faster onset of action and faster recovery times than fentanyl (Sanford et al., Anesthesia and Analgesia, 65:259-66, 1986). As compared to fentanyl, use of sufentanil can result in more rapid pain relief with the ability to titrate the effect and avoid overdosing.

Importantly, sufentanil has been shown to produce endocytosis of the muopioid receptor 80,000 times more potently than fentanyl (Koch et al., Molecular Pharmacology, 67:280-87, 2005). The result of this receptor internalization is that neurons continue to respond to sufentanil more robustly over time than with fentanyl, suggesting that clinically less tolerance would develop to sufentanil compared to fentanyl with repeated dosing.

The use of sufentanil clinically has predominantly been limited to IV administration in operating rooms or intensive care units. There have been a few studies on the use of liquid sufentanil preparations for low-dose intranasal administration (Helmers et al., 1989; Jackson K, et al., J Pain Symptom Management 2002: 23(6): 450-452) and case reports of sublingual delivery of a liquid sufentanil preparation (Gardner-Nix J., J Pain Symptom Management. 2001 August; 22(2): 627-30; Kunz K M, Theisen J A, Schroeder M E, Journal of Pain and Symptom Management, 8:189-190, 1993). In most of these studies, the smallest dosing of sufentanil in adults was 5 mcg in opioid naïve patients. Liquid administered to the oral or nasal mucosa suffers from lower bioavailability and possibly a shorter duration of action as demonstrated by the animal studies (sublingual liquid) described herein, as well as the literature (nasal liquid drops—Helmers et al., 1989). Gardner-Nix provides analgesic data (not pharmacokinetic data) produced by liquid sublingual sufentanil and describes the analgesic onset of liquid sublingual sufentanil occurring within 6 minutes but the duration of pain relief lasted only approximately 30 minutes.

Prior to the work of the current inventors, no pharmacokinetic data had been published on sublingual sufentanil in any form.

The claimed drug dosage forms contain from about 0.25 to about 200 mcg of sufentanil per dosage form for oral transmucosal delivery. In one exemplary embodiment, each dosage form contains from about 0.25 to about 200 mcg of sufentanil, alone or combination with one or more other therapeutic agents or drugs.

Exemplary drug dosage forms for administration to children (pediatric patients) contain from about 0.25 to about 120 mcg of sufentanil per dosage form. For example, a drug dosage form for administration to children may contain about 0.25, 0.5, 1, 2.5, 4, 5, 6, 8, 10, 15, 20, 40, 60 or 120 mcg of sufentanil for oral transmucosal delivery. It follows that for pediatric patients, an exemplary dose range is from at least about 0.02 mcg/kg to about 0.5 mcg/kg with a preferable range of from about 0.05 to about 0.3 mcg/kg.

Exemplary drug dosage forms for administration to adults contain from about 2.5 to about 200 mcg of sufentanil per dosage form. For example, a drug dosage form for administration to adults may contain about 2.5, 3, 5, 7.5, 10, 15, 20, 40, 60, 80, 100, 120, 140, 180 or 200 mcg or more of sufentanil for oral transmucosal delivery.

Preferably, a sufentanil-containing dosage form comprises from about 2 to about 200 micrograms (mcg) of sufentanil, e.g., 5 mcg, 10 mcg, 15 mcg, 20 mcg, 30 mcg, 40 mcg, 50 mcg, 60 mcg, 70 mcg, 80 mcg or 100 mcg of sufentanil.

As will be understood by those of skill in the art, the dose will be on the low end of the range for children and the high end of the range for adults dependent upon body mass, in particular when administered long term to opioid-tolerant adults. Prior to the work of the current inventors, small-volume oral transmucosal drug delivery dosage forms of sufentanil have not been described.

In various embodiments, the claimed dosage forms provide effective pain relief in all types of patients including children, adults of all ages who are opioid tolerant or nave and non-human mammals. The invention finds utility in both the inpatient and outpatient setting and in the field.

V. Congeners of Sufentanil

Congeners of sufentanil find use in the compositions, methods and systems described herein, examples of which include remifentanil and alfentanil.

In certain embodiments, the dosage form comprises at least 0.005% to as much as 99.9% by weight of alfentanil, lofentanil, carfentanil, remifentanil, trefentanil or mirfentanil. The percentage of active ingredient(s) will vary dependent upon the size of the dosage form and nature of the active ingredient(s), optimized to obtain maximal delivery via the oral mucosal route. In some aspects more than one active ingredient may be included in a single dosage form.

Remifentanil is a potent sufentanil congener that is metabolized much more rapidly than fentanyl or sufentanil, but may be suitable for treatment of acute pain when delivered via a sustained-release formulation. A remifentanil-containing dosage form typically comprises from about 0.25 mcg to 99.9 mg of remifentanil. The dose ranges for the remifentanil formulation may include 0.1 mcg/kg-50 mcg/kg over a time period of 20 minutes, for example, for both adult and pediatric patients. These dosages may be repeated at appropriate time intervals, which may be shorter than the time intervals for fentanyl or sufentanil.

Alfentanil is also a potent sufentanil congener that is rapidly metabolized but may be suitable for use in a sustained-release formulation. The dosage forms may contain from about 10 to about 10000 mcg of alfentanil per dosage form for oral transmucosal delivery. As will be understood by those of skill in the art, the dose will be on the low end of the range for children and the high end of the range for adults dependent upon body mass, in particular when administered long term to opioid-tolerant adults.

Exemplary dosage forms for administration to children (pediatric patients) contain from about 10 to about 6300 mcg of alfentanil per dosage form. For example, a dosage form for administration to children may contain about 10, 25, 50, 130, 210, 280, 310, 420, 600, 780, 1050, 2100, 3000 or 6300 mcg of alfentanil for oral transmucosal delivery.

Exemplary dosage forms for administration to adults contain from about 70 to about 10000 mcg of alfentanil per dosage form. For example, a dosage form for administration to adults may contain about 70, 140, 160, 210, 280, 310, 420, 600, 780, 1050, 2100, 3000, 6300 or 10000 mcg or more of alfentanil for oral transmucosal delivery.

Following delivery of a single dose of a sufentanil-, alfentanil-, or remifentanil-containing dosage form to a human subject, the plasma level of sufentanil, alfentanil or remifentanil may reach a maximum level within 60 minutes, e.g., between 5 and 50 minutes or between 10 and 40 minutes following administration.

VI. Treatment Of Pain

Patients suffering from chronic painful conditions can also have intermittent exacerbations of their pain, requiring acute use of fast-acting breakthrough opioids in addition to their use of slow-onset time-release opioids for their baseline chronic pain.

Breakthrough pain or procedural pain can be intense for short periods of time, as short as 1 or 2 minutes or as long as 30 minutes or more, therefore there would be a significant advantage in providing an opioid formulation that produced more rapid clinically effective plasma levels with a more consistent and predictable period of effect, but also had a limited half-life to avoid excessive opioid dosing for short duration pain events.

Opioids remain the most powerful from of analgesics, however, improved forms are needed that have minimal side effects, and can be provided in a manner in which patient use can be easily tracked by the physician.

Using current treatment methods, pain control is attempted using a number of interventions, which generally include: patient-controlled analgesia (PCA), continuous epidural infusion (CEI), other types of acute pain control, palliative care pain control, and home health patient pain control. These methods meet with varying degrees of success with respect to duration of control, ease of treatment and safety versus side effects.

The need for rapid treatment of acute pain occurs in many different clinical situations, including post-operative recuperation, rheumatoid arthritis, failed back, end-stage cancer (i.e., breakthrough pain), etc. Post-operatively, for example, patients suffer from severe pain for the first few days followed by days of mild to moderate levels of pain.

The most common analgesic used to treat moderate to severe post-operative pain is IV morphine. This is either delivered on an "as needed" basis by a nurse to the patient by an IV injection or commonly a morphine syringe is placed in a PCA pump and the patient self-administers the opioid by pressing a button which has a lock-out feature. Other opioids, such as hydromorphone and fentanyl may also be used in this manner.

Treatment of acute pain is also necessary for patients in an outpatient setting. For example, many patients suffer from chronic pain and require the use of opioids on a weekly or daily basis to treat their pain. While they may have a long-acting oral or transdermal opioid preparations to treat their chronic underlying pain levels, they often need short-acting potent opioids to treat their severe breakthrough pain levels.

Treatment of acute pain is also necessary "in the field" under highly sub-optimal conditions. Paramedics or military medics often are required to treat severe acute pain in unsterile situations, where needles used for IV or IM administration can result in unintended needle sticks, risk of infection, etc. Oral opioid tablets often take 60 minutes to provide relief which is too long for someone in severe pain.

In a number of clinical settings, there is clearly a need for improved means to administer a drug that produces effective pain relief in a manner that is titratable, safe and convenient, and non-invasive that provides relief from acute, severe breakthrough or intermittent pain over an appropriate period of time.

The claimed methods and systems rely on administration of dosage forms comprising a pharmaceutically active substance such as sufentanil which is effective for the treatment of pain (acute, intermittent or breakthrough pain) using a dispensing device that includes features such as lock-out, a means for user identification prior to drug administration and a means to protect the dosage forms stored therein. The claimed methods and systems thereby provide significant advantages over currently available treatment modalities in terms of both safety and efficacy.

VI. Dispensing Devices

Dispensing devices, methods and systems for oral transmucosal administration of small volume drug dosage forms are provided. The dispensing devices are typically handheld and portable and comprise a housing having a dispensing end which typically has a proboscis with a shroud that provide a means for blocking or retarding saliva ingress and/or moisture control. The dispensing devices further provide safety features such as a means for lock-out and a means for user identification.

The claimed dispensing devices, methods and systems comprise delivery of small volume dosage forms to the oral mucosa. The invention is not limited to the specific devices, systems, methodology and dosage forms detailed herein, as these may, of course, vary. It is also to be understood that the terminology used herein is for the purpose of describing particular embodiments only, and is not intended to limit the scope of the present invention.

Blocking/Retarding Saliva and Moisture Ingress

In some embodiments, the claimed dispensing devices comprise a means for minimizing or eliminating saliva ingress and moisture ingress into the dispensing device: (1) to avoid wetting the dosage forms therein; (2) to isolate any saliva that enters the dispensing device in such a manner that the dosage forms therein remain dry; (3) to absorb or adsorb any saliva that enters the dispensing device in such a manner that the dosage forms remain dry; (4) to block saliva and moisture from entering the device to protect the dosage forms from vapor and liquid phase moisture, or (5) any combination thereof.

The dispensing device may have a means for preventing and/or controlling humidity ingress due to ambient conditions outside of the device.

The means for minimizing or eliminating saliva ingress or preventing other moisture from entering the dispensing device includes, but is not limited to, one or more flexible or rigid seals, one or more flexible or rigid wipers, use of one or more absorbent material components such as a desiccant or pad, a door or latch that is manually or automatically opened and closed, multiple stage delivery systems, a positive air pressure and airflow, or an air gap or prescribed distance or barrier/shroud maintained between the dosage form delivery orifice and the mucous membrane tissues within the mouth that may transport the saliva. The shroud limits the ability of the tongue or oral mucosa to contact the dosage form dispensing area, thereby controlling saliva contact and ingress. By inhibiting or eliminating the "wetness" inside the shroud and on the surface of the valve/seal, the dosage form is dispensed without adhesion occurring between the dosage form and the shroud or valve/seal.

To protect the drug dosage forms from exposure to moisture either from humidity, saliva ingress, or accidental exposure to other water based liquids, the dispensing device and the container or cartridge which houses the dosage forms within the device contains a desiccant.

Means for trapping or otherwise isolating saliva or moisture if it enters the device include, but are not limited to, a hydrophilic wicking material or component, an absorbent or adsorbent material or component, a desiccant material or component, a separate track or channel for moisture to collect, a separate channel to communicate moisture to the absorbents or adsorbents, or any combination of these materials or components.

A desiccant is a sorbant, in the form of a solid, liquid, or gel that has an affinity for water, and absorbs or adsorbs moisture from it's surrounding, thus controlling the moisture in the immediate environment. Any commercial desiccant may be used. Commercial desiccants typically take the form of pellets, canisters, packets, capsules, powders, solid materials, papers, boards, tablets, adhesive patches, and films, and can be formed for specific applications, including injection moldable plastics. There are many types of solid desiccants, including silica gel (sodium silicate, which is a solid, not a gel), alumino-silicate, activated alumina, zeolite, molecular sieves, montmorillonite clay, calcium oxide and calcium sulfate, or others, any of which may be used in the claimed dispensing devices. Different desiccants have different affinities to moisture or other substances, as well as different capacities, and rates of absorption or adsorption. Also, different types of desiccants will come to equilibrium at different relative humidities in their immediate surroundings. As a means for protecting the dosage forms and the internal portions of the dispensing device from moisture, one or more desiccants may be employed at the proboscis; in or adjacent to the dosage form; in or adjacent the delivery pathway; in or adjacent the dosage form, tablet magazine or cartridge; in or adjacent to other components of the dispensing device; formed as an injection molded component of the dispensing device; a compressed desiccant that is pressed into location; or desiccant in any other location within or without the device.

In one preferred embodiment, the desiccant snaps into a cavity in the side of the cartridge. There are holes in the desiccant cavity that connect it to the dosage form stack, exposing the dosage forms to desiccant and keeping them dry.

The claimed dispensing devices rely on valves, pads, seals, the rest position of the push rod, proboscis design and a shroud to minimize or eliminate saliva ingress or moisture into the dispensing device during administration of the dosage form.

Valves for use in the claimed devices are typically dome/trocar type valves that provide enough sealing force to keep saliva and/or moisture from entering the device and serve to minimize or eliminate saliva ingress or moisture by closing the distal orifice during dispensing and after a dosage form has been dispensed.

Pads for use in the claimed devices have various geometries that aid in contacting or communicating with the pushrod in order to removed liquid from the push rod surface. Such pads typically contain hydrophilic properties and serve to minimize or eliminate saliva ingress or moisture ingress by transporting the liquid away from the track and push rod.

Seals and wipers for use in the claimed devices are designed to maintain a uniform seal around a drug dosage form and a pushrod during delivery and are characterized by flexible materials that impart a seal around the dosage form and pushrod and serve to minimize or eliminate saliva ingress or moisture by sealing and wiping the orifice and pushrod before, during, and after dispensing.

The rest position of the push rod in the claimed devices is characterized by positioning the pushrod in an intermediate location distal to the cartridge exit, and proximal to the distal dispensing orifice and serves to minimize or eliminate saliva ingress and moisture by allowing the pushrod to reside in a location that contains a desiccant, absorbents, or channel that dries the pushrod while at rest between dosage dispenses.

The proboscis design for use in the claimed devices is characterized by a distal device shape, typically an S-shape, that aids in use of the device and/or placement of the tip on the oral mucosa of the subject. The shape typically has curves, angles, and geometries such that it enables proper use of the device and placement of the dosage form on the oral mucosa of the subject, e.g., in the sublingual space.

The shroud of the claimed devices has a geometry that forms a barrier between the device and the oral mucosa and tongue, a relief for dosage form delivery, and an interior that is hydrophobic or hydrophilic and serves to minimize or eliminate saliva ingress or moisture ingress by creating a barrier from the oral mucosa contacting the valve area and dosage form, aiding in dosage form dispensing and discouraging dosage form adherence to the shroud. The shroud may have a rounded interior surface or other geometries to mitigate the dosage form adhering to the shroud. The shroud limits the ability of the tongue or oral mucosa to contact the dosage form dispensing area, thereby controlling saliva contact and ingress.

FIGS. 1A-E provide schematic depictions of a variety of aspects of one embodiment of a drug dispensing device constructed to hold a plurality of dosage forms for oral transmucosal delivery. FIG. 1A is a schematic depiction of a fully assembled or single piece dispensing device 11 of the invention. In FIG. 1B, the dispensing device 11 includes a reusable head 13 and a disposable body 15; in FIG. 1C the dispensing device 11 further includes a cartridge 17 in FIG. 1D the dispensing device 11 includes a valve 33, a proboscis 31, a latch button 19, a power train coupling 25, a hub lock 21 and a dispense button 23; and FIG. 1E is a schematic depiction of a reassembled and complete dispensing device 11.

Figure 2:
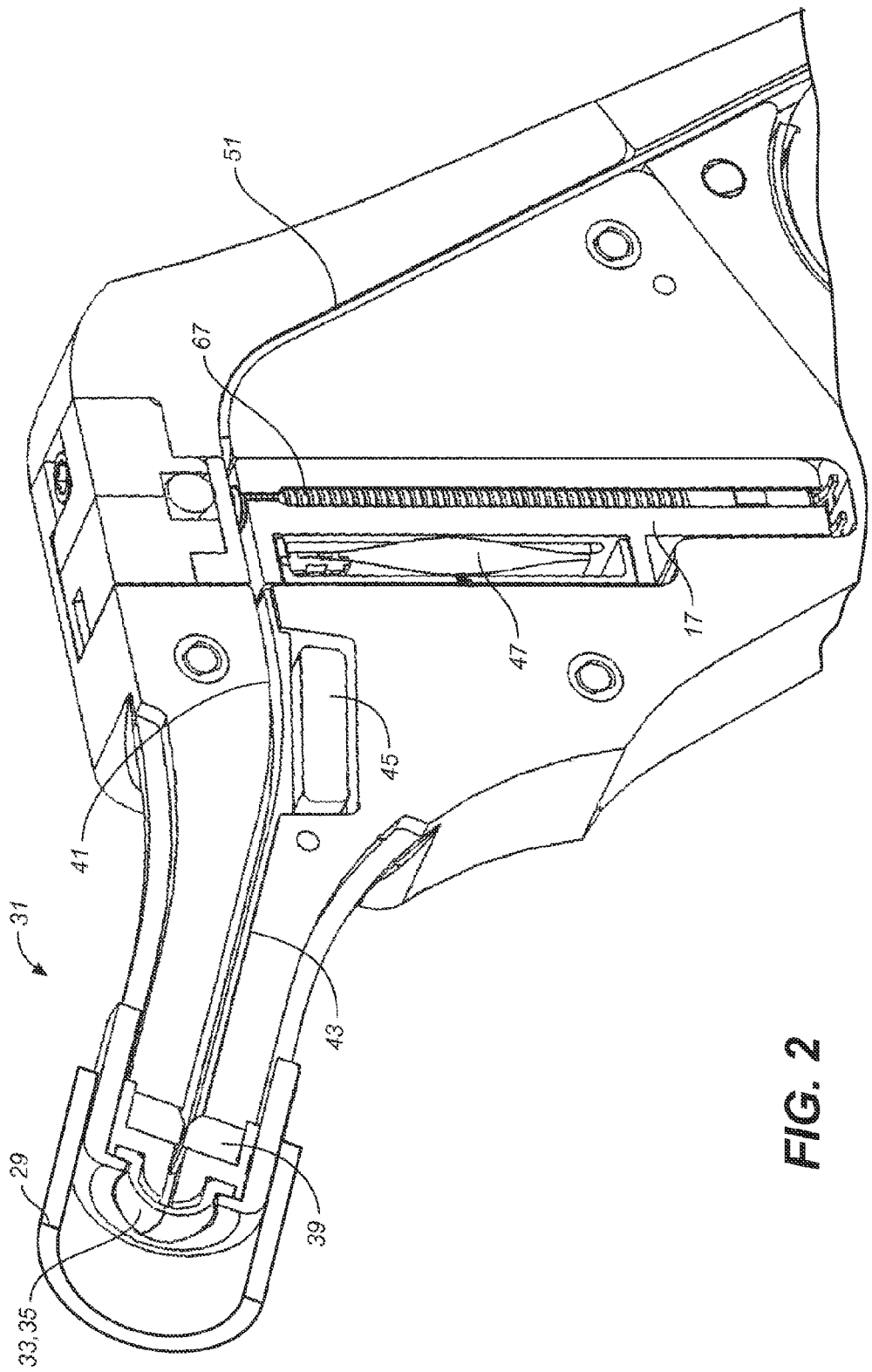
FIG. 2 is a schematic depiction of an exemplary dispensing device showing features designed to block or retard saliva and moisture ingress.

FIG. 2 provides a schematic depiction of an exemplary dispensing device wherein the dispensing tip comprises a shroud 29 having a one or more of: a wiping/sealing valve 37, an absorbent pad 39, a drug drying chamber/moisture communication channel 43, desiccant in the channel 45, a cartridge 17 containing dosage forms 67 and desiccant in the cartridge 47.

Figure 3A:
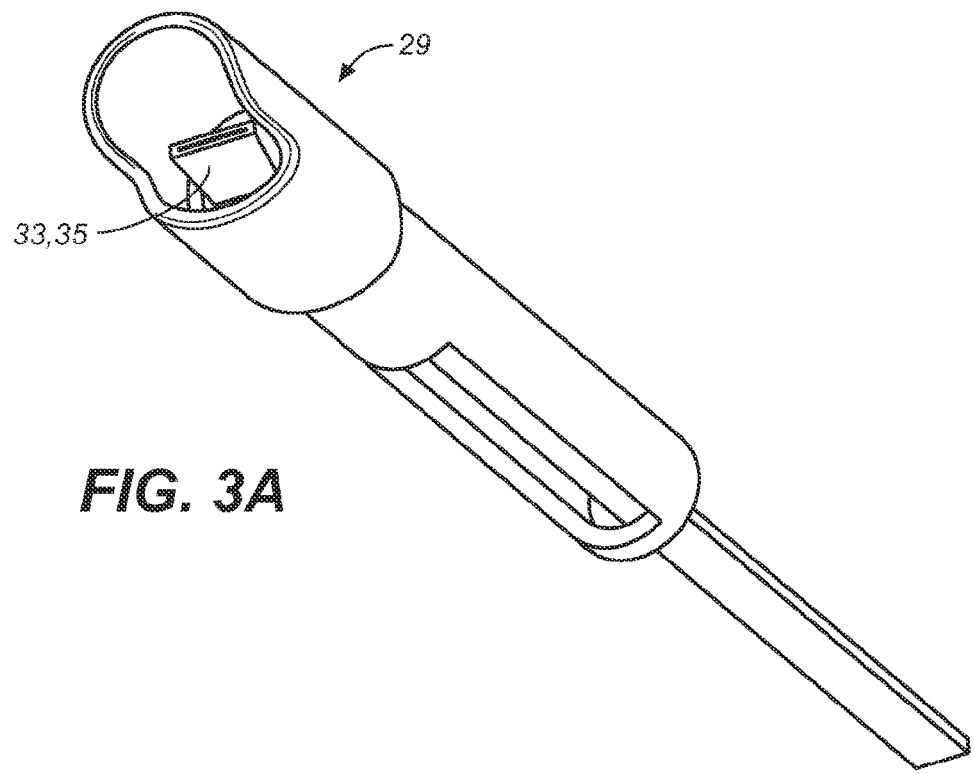
FIGS. 3A and 3B are schematic depictions of an exemplary geometry for a dispensing tip.
Figure 3B:
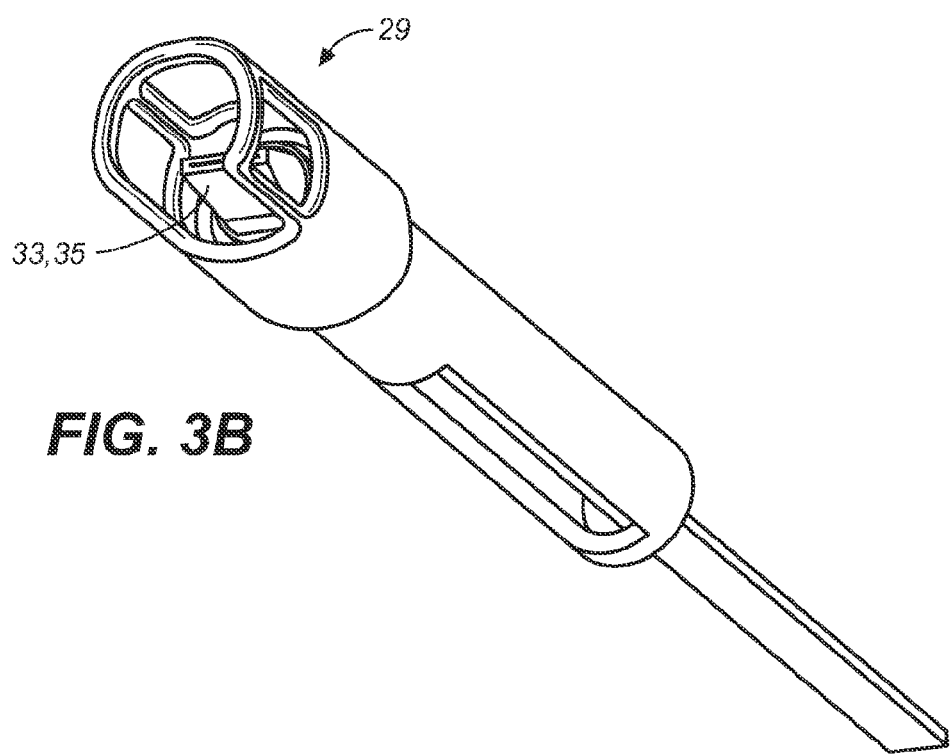
Figure 4A:
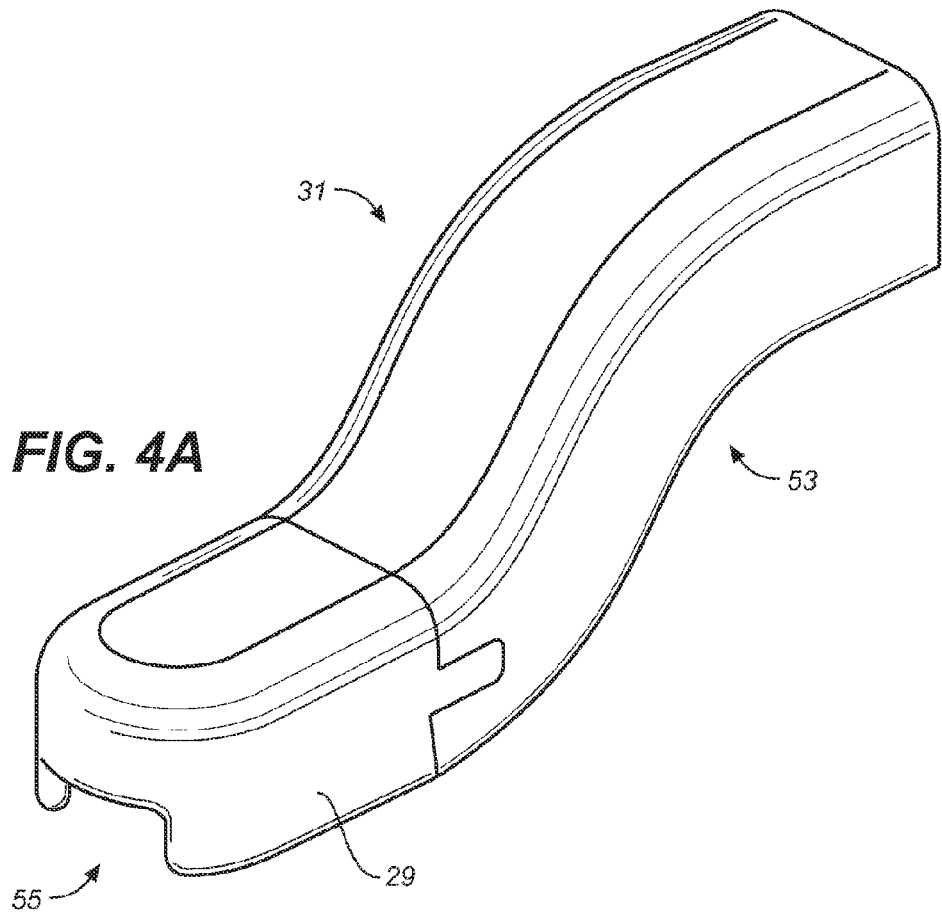
FIGS. 4A-D are a schematic depiction of an exemplary proboscis of a dispensing device.
Figure 4B:
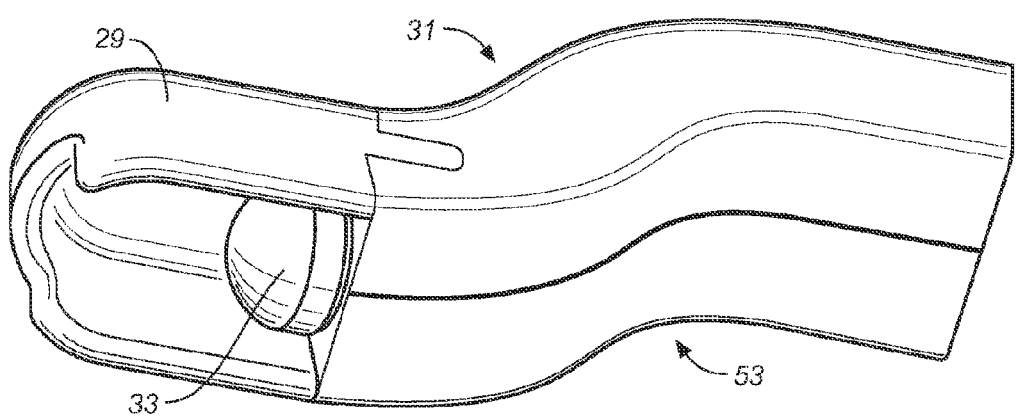
Figure 4C:
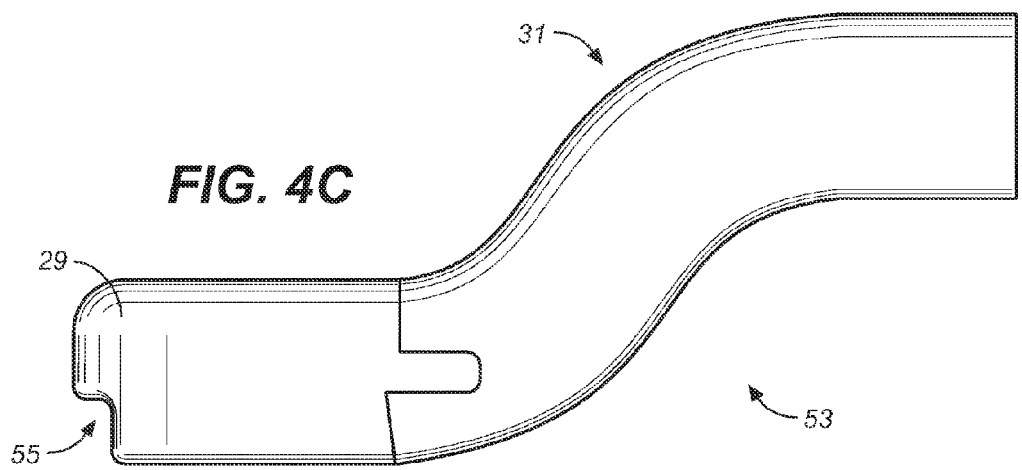
Figure 4D:
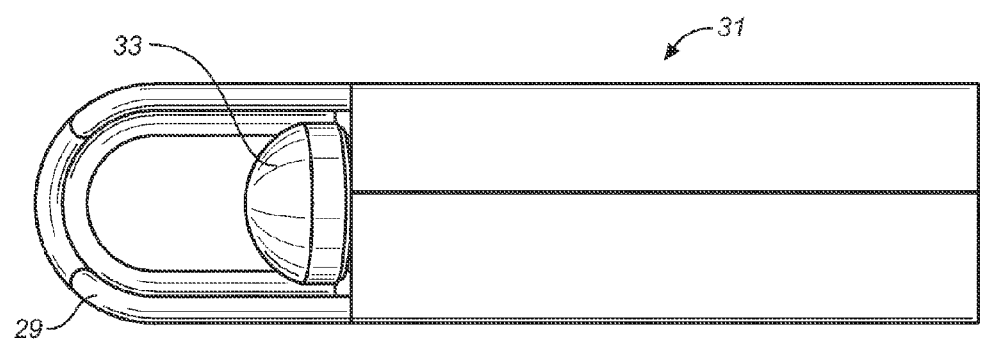

FIGS. 3A and 3B are schematic depictions of an exemplary geometry for the dispensing tip that prevents contact of one or more seals 33, 35 with the moist or wet surface of the oral mucosa via a shroud 29.

FIGS. 4A-D are a schematic depiction of an exemplary proboscis 31 of a dispensing device 11 wherein the proboscis 31 comprises a shroud 29, a valve 33 for dispensing a dosage form 67 and a cut-out/relief 55 for the dosage form 67 to be placed against the oral mucosa and not moved when the device 11 is withdrawn following dispensing.

A means for minimizing saliva ingress and moisture into the claimed devices is important for preservation of the integrity of dosage forms during storage, e.g., prior to an between oral transmucosal administrations.

The claimed dispensing devices may be used to administer a drug dosage form that is sensitive to moisture and/or humidity. In such cases, a drug dosage form cartridge serves to protect the drug dosage form from liquid and vapor phase moisture, including humidity, liquid moisture, saliva, mucus, etc. The cartridge may be cylindrical, disk-shaped, helical, rectilinear, non-ordered, or may take the form of any assemblage of drug dosage forms that allows the drug dispensing device to dispense them in a controlled manner. To prevent the unused drug dosage forms from absorbing moisture or otherwise becoming exposed to moisture prior to use, the cartridge may provide a means of sealing the drug dosage forms from exposure to moisture. This may accomplished by use of a cartridge that contains individually packaged drug dosage forms separated by a thin impermeable foil or impermeable material such that when one drug dosage form is dispensed from the cartridge, the seal protecting the remaining dosage forms remains unbroken. Alternatively, the dosage forms may be packaged in such a manner within the cartridge that two or more dosage forms are packaged together in each separate sealed compartment. In some embodiments, all of the dosage forms in a cartridge may be packaged together in a foil sealed compartment.

A drug cartridge that houses small volume drug dosage forms within the dispensing device may afford a seal against moisture by means of a septum, an elastomeric seal or valve, a sliding, translating, hinged door or valve, or by means of sealing against another component of the drug dispensing device when loaded. In this manner, a single re-sealable seal may be opened either independently or by means of the passage of a dosage out of the cartridge. Once the dosage form is delivered from the cartridge, the re-sealable seal on the cartridge may be re-sealed to prevent moisture or other contaminants from damaging the remaining drug dosage forms within the cartridge. The cartridge may further have a non-re-sealable seal that is broken when it is loaded into the drug dispensing device or upon delivery of the first dosage form from the cartridge.

In other embodiments, the cartridge contains a desiccant or other absorbent or adsorbent material to absorb or adsorb moisture that penetrates the cartridge either prior to use or during normal use. A cartridge for use in a claimed dispensing device may contain any combination of individually sealed dosage forms, multiply sealed dosage forms, re-sealable seals, non-re-sealable seals, desiccants, absorbents, or adsorbents. In one embodiment, a cartridge for use in the dispensing device in holds sufficient drug dosage forms for 1-5 days of treatment, e.g. 40 dosage forms or sufficient drug dosage forms to provide 48 to 72 hours of treatment.

Pushrod Design

Figures 5A, 5B:
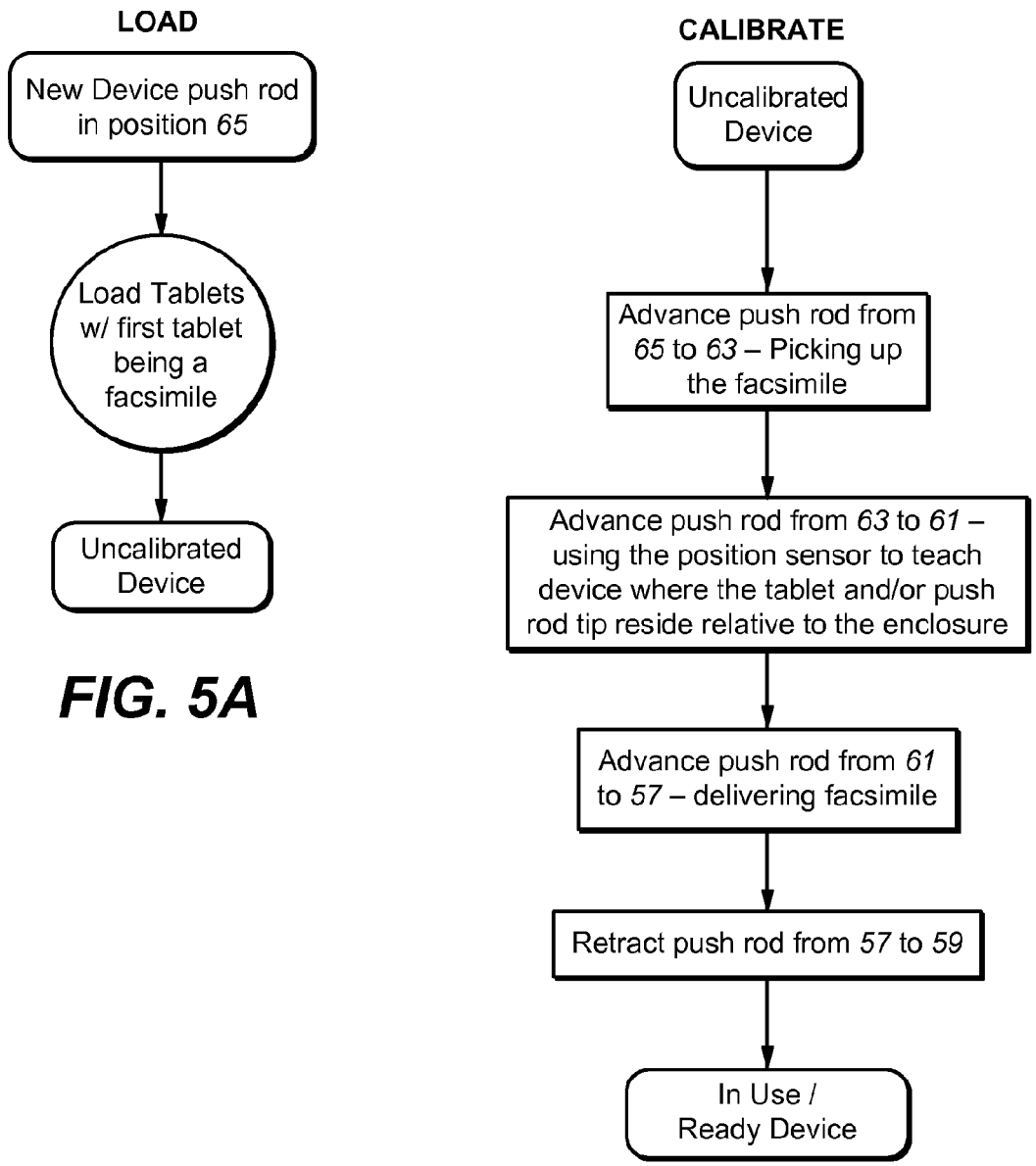

FIGS. 5A-D provide a series of flow diagrams for use of an exemplary dispensing device showing pusher logic, wherein FIG. 5A shows the LOAD feature; FIG. 5B shows the device calibration logic flow. Referring to FIG. 6, the pushrod 51 is advanced from position 65, picks up the shipping tablet 69 at position 63, and is further advanced to position 61. At position 61, the device senses the presence of the shipping tablet 69 and/or push rod 51. In doing so, the device is calibrated and knows the location of the shipping tablet 69 and/or end of the push rod 51 regardless of assembly tolerances, variations in push rod length and push rod end conditions. Following this calibration, the push rod 51 advances the shipping tablet 69 from position 61 to position 57 where the shipping tablet 69 is dispensed from the device. During this operation, the device is able to distinguish between a shipping tablet 69, a push rod 51, and a drug dosage form 67. This differentiation enables the device to confirm that a cartridge is unused because a shipping tablets is the first thing dispensed from a new cartridge during device setup. The feature that provides the means for differentiating between the shipping tablet, push rod, and dosage form 67 may be optical, physical, RF, electronic (resistive, capacitive, or other) or magnetic. The push rod 51 advance from position 65 and position 57 described above, could be continuous or intermittent and a physical stop at position 61 is not required. The push rod 51 then retracts from position 57 to position 59, placing the device 11 in the ready position with the push rod 51 under the remaining dosage forms 67. In this position, the push rod 51 keeps dosage forms 67 from inadvertently falling out of the device 11.

Figure 5C:
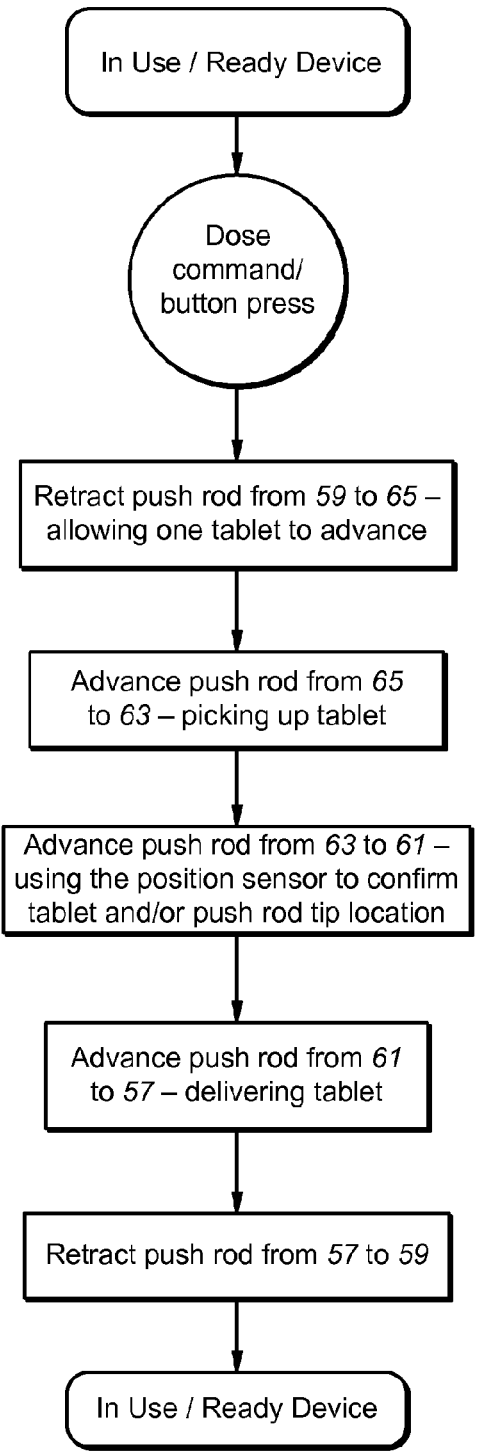
Figure 6:
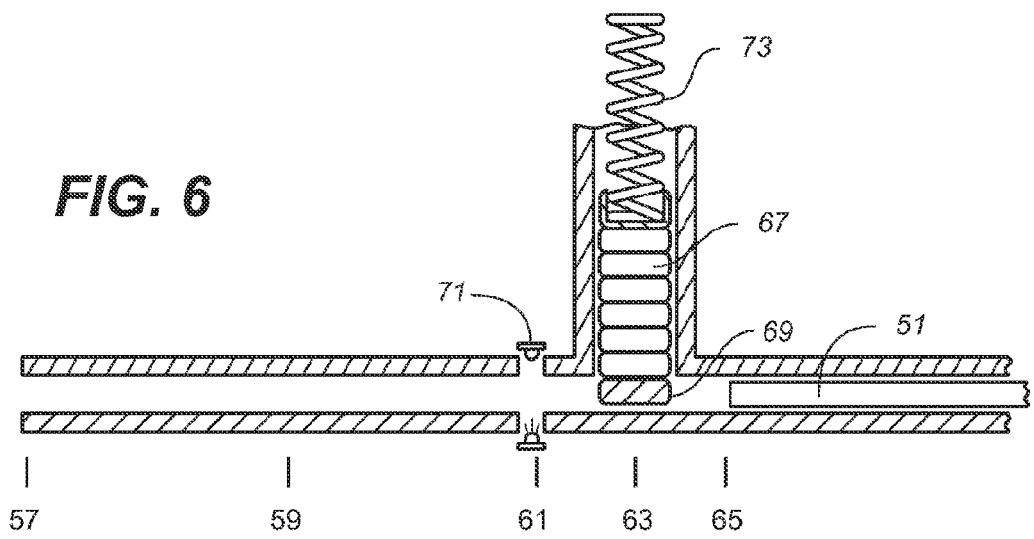
FIG. 6 is a schematic depiction of an exemplary device showing the stages of push rod/tablet interaction during device use.

FIG. 5C shows the device dispense logic flow. Referencing FIG. 6, following a dose command, the push rod 51 retracts from position 59 to position 65, allowing the dosage forms 67 to advance into the push rod track. The push rod 51 then advances from position 65, picks up a dosage form at position 63, and then dispenses the dosage forms 67 from the device at position 57. Between positions 63 and 57, the presence of a dosage form 67 is sensed/confirmed at position 61 by the position sensor. The push rod then retracts from position 57 to position 59, placing it in the ready position with the push rod 51 is under the remaining dosage forms 67. In this position, the push rod 51 is allowed to dry before the next dosage form 67 dispense, as well as keeps dosage forms 67 from inadvertently falling out of the device 11.

Figure 5D:
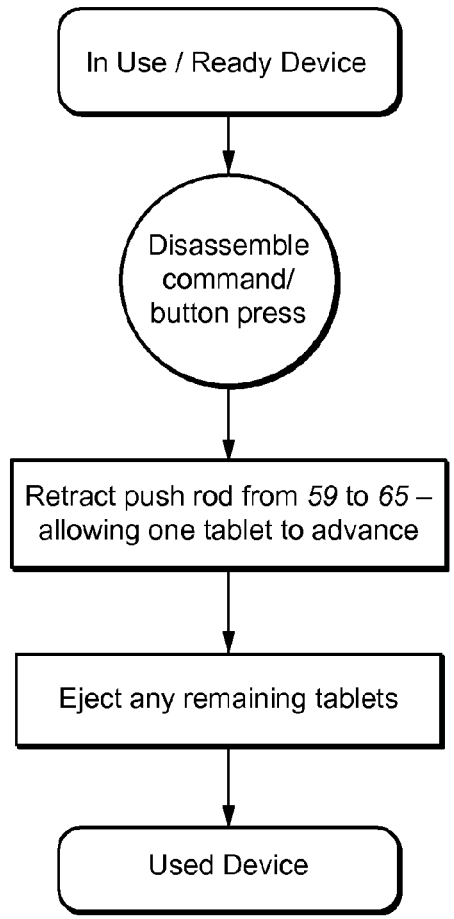

FIG. 5D shows the device disassemble logic flow. Following a "disassemble" command, the push rod 51 is moved to position 65. This allows for the removal of any remaining dosage forms 67 without push rod interference.

FIG. 6 is a schematic depiction of an exemplary dispensing device showing the stages of push rod/dosage form interaction during device use. In FIG. 6, the push rod 51, dosage forms 67, shipping tablet 69, spring 73 and position sensor 71 are shown. During use, the push rod 51 moves between positions 57, 59, 61, 63 and 65, also shown in FIG. 6 and further detailed in FIGS. 5A-D.

Dosing History/Feedback

Further embodiments of the device include the ability to store historical use information and the ability to transmit such information. The device may be capable of unidirectional (downloading) or bidirectional information transfer. For example, an exchange of information may be accomplished by downloading stored information to a computer through a physically wired interface, such as a USB or any other communication connection. Alternatively, information may be communicated via a wireless system.

FIGS. 22 and 23 depict other exemplary dispensing mechanisms with pushrods for dispensing drug dosage forms, wherein the pushrods are designed to be flexible. FIG. 22 shows dispensing mechanism 174 for singulating and advancing a drug dosage form 48 through a nonlinear or linear pathway by means of a flexible shaft 176 attached to an advancing mechanism, such as a rotation hub, such that advancing or retracting the flexible shaft within the nonlinear or linear pathway allows for the dispensing of a tablet or other dosage form 48 through the nonlinear pathway. FIG. 23 shows dispensing mechanism 180 for singulating and advancing a drug dosage form 48 through a nonlinear or linear pathway by means of a flexible shaft 182 attached to an advancing mechanism, such as a rotation hub, such that advancing or retracting the flexible shaft within the nonlinear or linear pathway allows for the dispensing of a tablet or other dosage form 48 through the nonlinear pathway.

In a related approach, the drug delivery device of the invention comprises a tubular cartridge containing the stack, a spring pushing the stack, a solid face, and a slider or pusher, similar to the embodiment described above. In this embodiment, the slider or pusher lacks a hole, but rather retracts from beneath the dosage form stack such that the spring can push the dosage forms up against the solid face. During actuation the pusher, which has a thickness equal to, larger than, or less than that of a single dosage form, pushes the first dosage form in the stack perpendicular to the cartridge and dispenses it out of the side slot.

In another embodiment of the invention, dosage forms are dispensed by moving a dosage form stack which is mounted with a pusher at one end and an elastomeric diaphragm retaining the opposite end of the dosage form stack. The diaphragm contains an orifice or hole or slot at the location of the first dosage form. Upon actuation, the pusher pushes the stack and a single dosage form emerges from the diaphragm hole, at which point the pusher retracts slightly to allow the elastomeric diaphragm to re-seal and close again. The elastomeric diaphragm may be a seal or wiper type seal.

In another embodiment, the dispensing device has a dose counting feature that monitors and stores the history of drug usage. Such information may include historical use information, for example the number of dosages stored and dispensed, and the times of dispensing.

Calibration

The dispensing device may be capable of self-calibration of the dispense mechanism, or the device may be calibrated manually. This process may employ a shipping tablet with a feature or features that physically differentiate it from a drug dosage form or the push rod. These features may be designed so that device calibration precision is higher that that attainable using a dosage form or push rod. The differentiating feature may be physical, optical, radio frequency (RF), electronic or magnetic.

User Identification Feature

In one aspect, the dispensing device comprises a detecting means for user identification such as a fingerprint reader, an optical retinal reader, a voice recognition system, a face recognition system, a dental imprint recognition system, a visual recognition system, or a DNA reader. The dispensing device may employ one or more means to identify the user, enabling the system to determine if a dispensing request is being made in an authorized or unauthorized manner. It is important for effective delivery of many potential drugs and drug dosage forms to ensure that the dispensing device is not accidentally or intentionally used by an unauthorized individual to prevent accidental or intentional diversion of the drug. Such user identification systems may recognize one or more users, for example, in an inpatient hospital setting the dispensing device could be programmed to recognize the patient to whom it is prescribed, as well as authorized healthcare providers such as nurses and physicians. In an outpatient home setting, for example, the dispensing device may only respond to the patient to whom it is prescribed.

The dispensing device may employ any means of user identification, including fingerprint identification, RFID detection with the use of an active or passive RFID tag on bracelet, necklace, clip, belt, strap, adhesive patch, implant, or means of locating and affixing a tag, retina identification, DNA identification, voice recognition, password or code entry, physical key, electronic or magnetic key, personal area network identification using the human body or clothing as a data or signal conduit, optical scanner or face recognition, sonic, subsonic or ultrasonic identification, or any other means of identifying an individual and verifying their identity.

One method of user identification is the use of a short distance ("near field") passive RFID tag attached to a bracelet, necklace, adhesive patch, clothing tag, orally mounted device, like an orthodontic retainer, belt, strap, some combination of these, or another location. When an RFID tag is used in the "near field", roughly defined as about 16% of the wavelength of the received signal, the tag behaves in the inductive mode of operation, coupling between the reader and tag antenna magnetically. The near field is characterized by at least two features: first is a rapid decline in field strength with distance, and second is a strong directionality of the signal. In the near field, the signal strength falls off very rapidly, with a signal strength loss of approximately 60 dB per decade in distance. For good inductive coupling between the transmitter antenna and the RFID tag antenna, the two antennas are oriented in parallel planes with the axes through the center of each antenna in close proximity. Strong signal strength (robust user identification) is provided when the device is very close to the RFID tag. At the same time, a very poor signal is provided when the device is further away from the tag, which helps prevent unauthorized use by someone other than the patient who attempts to use the device. It is preferable to operate in this near field region with good antenna alignment. Furthermore, it is preferable to operate with a very short distance of adequate signal strength for a positive identification, so that it is very difficult to receive a signal if the device is not in the proper orientation and proximity to the RFID tag. To attain a short distance and a proper alignment between antennas, the dispensing device may be designed so as to properly locate the RFID reader antenna, mounted in the dispensing device, adjacent to an RFID tag antenna, mounted, for example, on a wrist band or bracelet, or a clothing tag on the collar, or an adhesive patch on the hand, arm, cheek, neck, or elsewhere. Furthermore, an RFID tag antenna on a wrist band or bracelet may be held in proper alignment and location by means of a small adhesive patch that prevents the bracelet from moving or rotation on the wrist.

In another embodiment, the dispensing device employs a high frequency RFID reader for use in the inpatient (hospital, clinic, etc.) setting, operating on or near the 13.56 MHz frequency band, and the patient is be fitted with a matching RFID tag and antenna on a disposable bracelet or wrist band, designed in such a way that if the bracelet or wrist band is removed the RFID tag, the antenna, or another component of the associated circuit will be damaged or destroyed, rendering the bracelet or wrist band non-functional. In one example, the range of the RFID communication is short, between 0 inches and 10 inches preferably, more preferably between 0 and 5 inches, and most preferably between 0 and 3 inches, and may additionally be directional, allowing proper use by the intended patient to be easy and reliable, while at the same time making unauthorized use by another individual difficult, very difficult, or impossible.

Lock Out

The dispensing device provides for lock out, requiring the patient to communicate with the physician or other authorized care giver to unlock the device for the next fixed period. In this way the device and dock provide for safe drug administration due to greater physician oversight and care management.

The dispensing device provides a means for adjusting both the initial dose and subsequent doses, as well as the lock-out time. The initial dose and lock out time may subsequently be adjusted dependent upon patient response, duration of treatment and the like.

The initial timed lock-out period for a claimed dispensing device is typically from about 1 minute to about 60 minutes, from 3 minutes to 40 minutes or from 5 minutes to 30 minutes, and in particular cases is set at any one minute interval from 1 to 60 minutes, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 minutes.

In some cases, a dispensing device has a fixed lockout between doses and may exhibit a shutdown after a fixed period of time. In other cases, the lock-out time is a programmable lock-out time. The lock-out time may also be a fixed time lock-out interval, a predetermined lock-out interval, a predetermined variable lock-out interval, a lock-out interval determined by an algorithm or a variable lock-out interval communicated to the device from a remote computer or docking station.

Additional Features

A dispensing device may provide the ability to recognize a specific cartridge by a mechanical, optical (e.g. bar code), electronic (e.g. microchip), magnetic, radio frequency, chemical, or other means of detecting and identifying the cartridge. In one exemplary embodiment, the drug-containing cartridge contains a physical keying detail on the cartridge that is physically detected by a sensor or switch or a series of sensors or switches in the dispensing device. Furthermore, the dispensing device may communicate uni-directionally or bi-directionally with the cartridge to exchange information. Such information may include drug name, dosage strength, usage information, lockout period, manufacturing lot number, indications for use, side effects, drug interactions, date of manufacture, date of expiration, serial number, number of doses in the cartridge, or any other relevant information. The dispensing device may be able to write, in addition to read, information to the cartridge, like date used, health care provider or other user identification, number of doses used, etc.

The dispensing device may provide mechanical protection for the dosage forms contained therein, preventing breakage, chipping, hydration etc., thereby allowing for dispensing of the undamaged dosage forms contained therein. This is of particular importance for small fragile and friable dosage forms.

The drug dispensing device may be powered by a battery, capacitor, fuel cell, or other power supply source, or may require no electrical power, but be manually activated.

In some embodiments, the dispensing device is capable of issuing alarms or other notifications when functional or safety issues arise. The alarm or other notification may trigger an alert on the dispensing device, on a dock or other peripheral device; on a computer or by means of a wired or wireless network, or may alert other remote devices. The alarm or notification may be audible, tactile, visual, or may employ other means of notifying one or more individuals.

Docking Station

In certain embodiments, the device includes a portable or fixed docking station that may query the device, reset it between dosing, lock it when not properly accessed, and control the dosing regimen. The drug dispensing device may communicate with a physician or care giver, via the dock, or by a wired or wireless communication means.

The dispensing device may employ one or more levels of interface for different types of authorized users, for example the patient, the nurse, the physician, pharmacist or other authorized medical or healthcare personnel. These different interfaces may include components such as keypads, buttons, graphical icons and instructions, lights, LED's, monochrome or color graphical or text displays, touch-screens, LCD's, sounds, tactile feedback, voice recognition interfaces, and other input and output devices and means. The activity, or mode, of the user interface may be determined by the mode of operation of the dispensing device, by a login or access activity by a user such as a password or code entry, by the connection or disconnection of the dispensing device from a dock, computer, or network, or by the detection of an authorized access key, such as a key, and/or RFID tag, or similar combination. Upon changing the interface mode, the functionality of the device may be changed, either activating, inactivating or changing the functionality of the various interface components described above. By allowing the device to have one or more interface modes, with differing functionality associated with each one, the device can be optimized for various uses.

Base Station

In some embodiments the drug dispensing system includes a base station for recharging the drug dispensing device and the portable docking FOB between uses. This base station allows for recharging the batteries or fuel cells in multiple dispensing devices and/or FOBs simultaneously. In addition to recharging the drug dispensing devices and FOBs, the base station may provide one or more of the following functionality: wireless or wired connectivity to a peripheral device, computer or network; feedback on the charging state for the devices being recharges; an interface for viewing, adding, deleting, or modifying the data on a drug dispensing device or FOB; a means for synchronizing data between multiple drug dispensing devices and/or FOBs; and a means for conducting a diagnostic test on drug dispensing devices and/or FOBs.

Single and Multiple Dose applicators

The invention provides disposable applicators for delivering dosage forms comprising sufentanil to the oral mucosa of a patient such that application to a predetermined location for drug delivery (e.g. the mouth, sublingual space, etc.) is effected.

In one approach to the invention, a dosage form is delivered to the oral mucosa, using a single dose applicator (SDA). The dosage form is provided in a child-resistant drug dispensing device or packaging and delivered for example, to the sublingual cavity. The dosage form may be self-administered or alternatively, the dosage form is administered with assistance with or without a device.

In one embodiment, a SDA is used to a drug dosage forms, provided as a solid tablet, a liquid capsule, a gel capsule, a liquid, a gel, a powder, a film, a strip, a ribbon, a spray, a mist, a patch, or any other suitable drug dosage form.

The SDA may contain the dosage form within, may have the drug dosage form attached or affixed to it, may have the dosage form dissolved in it, and may afford a seal against moisture, humidity, and light. The single dose applicator may be manually manipulated by a patient, healthcare provider, or other user to place the dosage form in the proper location for drug delivery.

In practicing the invention, a single- or multiple-dose applicator or drug dispensing device may be used to deliver tablets or other dosage forms into the hand, mouth, under the tongue, or to other locations appropriate for specific drug delivery needs.

In one embodiment, a single- or multiple-dose applicator or drug dispensing device is used to deliver a dosage form to the oral mucosa, e.g., the sublingual space.

The dosage forms inside the dispensing device remain dry prior to dispensing, at which point a single dosage form is dispensed from the device into the mouth, e.g., the sublingual space, wherein a patient's saliva will wet the tablet and allow for tablet disintegration/erosion and drug delivery.

The SDA may be provided as a pair of forceps, a syringe, a stick or rod, a straw, a pad, a capsule, a cup, a spoon, a strip, a tube, an applicator, a dropper, a patch, an adhesive pad, an adhesive film, a sprayer, an atomizer, or any other form suitable for the application of a single drug dosage form to the oral mucosa of a subject, e.g., the oral mucosa in the sublingual space. As will be understood by one of skill in the art, the SDA design may vary, so long as it is effective to place a drug dosage form, such as a tablet, in the desired location on an oral mucosal membrane, e.g., in the sublingual space, in a manner that preserves integrity of the drug dosage form in the dispensing process. After use, the SDA is disposed of, so as to eliminate the risk of contaminating the drug dispensing device with saliva, or other contaminants.

For sublingual administration, a small volume dosage form is administered sublingually by placement under the tongue, using an SDA, generally adjacent the frenulum.

The dosage form may be provided in a package that consists of molded plastic or laminate that has indentations ("blisters") into which a dosage form is placed, referred to herein as a "blister pack". A cover, typically a laminated material or foil, is used to seal to the molded part. A blister pack may or may not have pre-formed or molded parts and may be used to package an SDA of any type.

Such blister packs may be provided in a child resistant multiple drug dispenser (MDA), which may serve to dispense the dosage forms housed therein or may be used for storage of a plurality of SDAs.

FIGS. 15A-C, FIGS. 16A-F, FIGS. 18A-C and FIGS. 19A and B are schematic depictions of exemplary embodiments of a SDA of the invention.

Figure 16A:
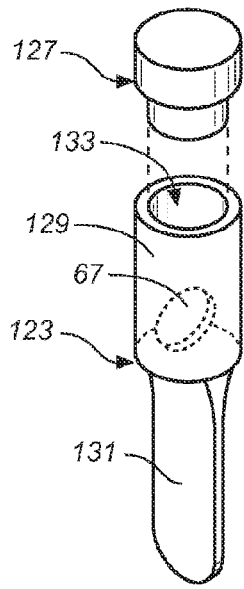
FIGS. 16A-F provide an illustration of six additional single dose applicators.
Figure 16B:
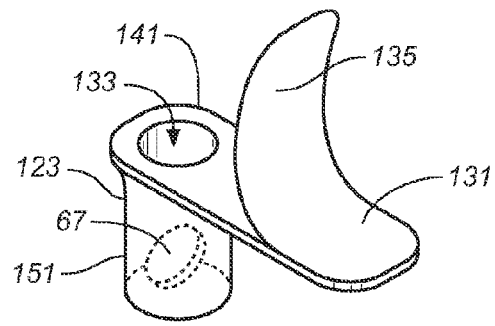
Figure 16C:
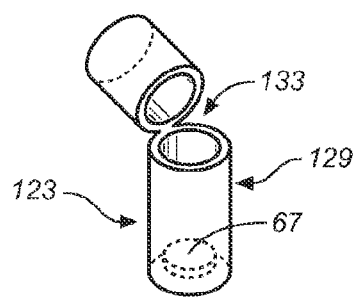
Figure 16D:
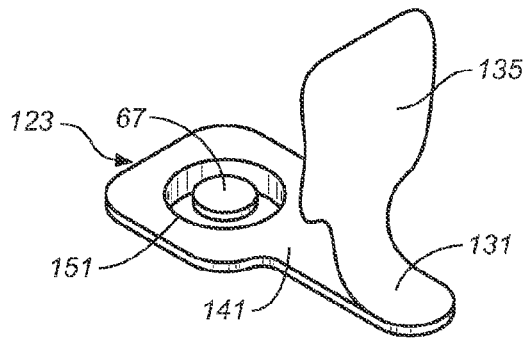

In one approach, the present invention provides disposable single dose applicators comprising a blister pack 151, which contains drug dosage forms 67 inside a housing and a handle 131, wherein a backing, such as a foil seal 135 covers the dosage form 67 and the handle 131, as shown for example in FIGS. 16B and 16D.

In one embodiment, the disposable single dose applicator, the combination of housing or tube 129 and handle 131 has the shape of a spoon.

The housing or tube 129 for the dosage form 67 is a blister pack 151 that accommodates a unit dose of a dosage form 67 for administration to a subject. The dosage form 67 is sealed in the blister pack 151 by a foil or other type of seal 135.

In some embodiments, the foil or other type of seal 135 is removed prior to administration of the dosage form 67 and the handle 131 is used to place the dosage form 67 in the appropriate location against the oral mucosa of the subject such that the dosage form 67 adheres to the oral mucosa. See, e.g., FIGS. 16B, 16D, 16E and 16F. In other embodiments, the foil or other type of seal 135 is perforated and removed prior to administration of the dosage form 67 by folding the applicator 123 at the perforation 149 prior to administration where the handle 131 is used to place the dosage form 67 in the appropriate location against the oral mucosa of a subject. See, e.g., FIGS. 19A and B. This permits the handling of only a single drug dosage form 67 at a time and prevents the other individually sealed drug dosage forms 67 from becoming exposed to saliva, humidity and the like.

The foil or other type of seal 135 of a disposable applicator 123 including handle 131 is typically made of a single piece of foil laminate, paper, plastic or other covering, i.e. an applicator tab 147 that spans the back of the housing or tube 129 alone or both the housing or tube 129 and the handle 131, effectively seals the dosage form 67 in a blister pack 151 or other container.

The handle 131 enables proper placement of the dosage form 67 without touching the dosage form 67.

A plurality of single dose applicators may be provided as a series of individual single dose applicators attached by the backing or housed in multiple dose dispenser 137.

Figure 14A:
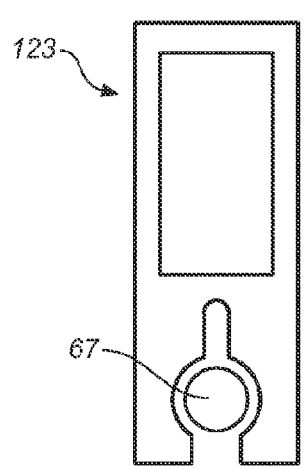
FIGS. 14A and 14B are schematic depictions of an exemplary single dose applicator.
Figure 14B:
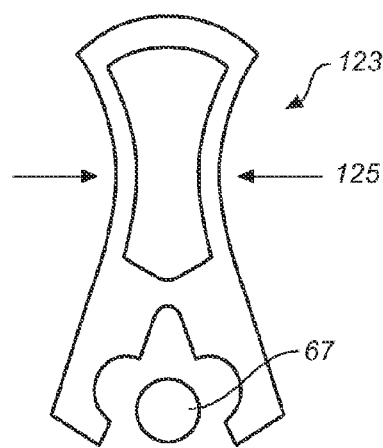

FIGS. 14A and 14B show one embodiment of a single dose applicator 123 a dispensing device for delivering drug dosage forms. The dispensing device shown in FIG. 14A depicts the single dose applicator 123 that is ready to dispense a drug dosage form 67. In one aspect of this embodiment, a user pinches the single dose applicator 125 which opens the applicator and a drug dosage form 67 is dispensed as shown in FIG. 14B.

FIGS. 15A-C show an embodiment of a single dose applicator 123 that is comprised of a applicator shaped as a tube 129, a stopper seal 127, a handle 131 (e.g., an ergonomic handle), and a single dosage form 67. FIG. 15A shows the single dose applicator 123 in its sealed configuration, prior to use. FIG. 15B shows the single dose applicator 123 with its stopper seal 127 removed, forming an opening 133, and ready for use. FIG. 15C shows the single dose applicator 123 tilted so as to dispense the dosage form 67 on the oral mucosa, e.g., in the sublingual space.

Figure 16E:
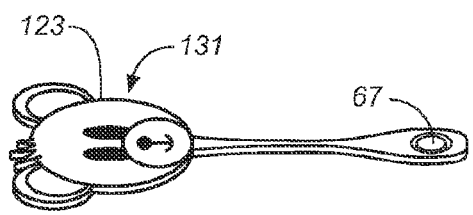
Figure 16F:
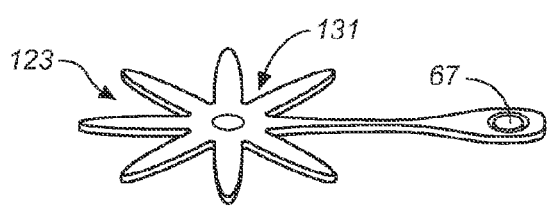

FIGS. 16A-F show several alternate embodiments of the single dose applicator 123. In all of these figures the applicator seal 127 is broken and the applicator is tilted so as to drop the drug dosage form 67 adjacent an oral mucosal membrane in the mouth of a subject, e.g., under the tongue for sublingual dosage form placement. FIG. 16A shows a tube like applicator 129 with a handle 131 located axially under the tube 129. FIG. 16B shows an applicator formed as a thermoform or blister package 151 with a foil seal 135 that is peeled so as to open the applicator package 141 prior to placing the dosage form 67. FIG. 16C shows an applicator that is a tube 129 which is broken to break the seal prior to dosage form 67 placement. FIG. 16D shows a blister pack tube 151 type dosage form package 141 with a handle 131 such that after the seal 135 is peeled back the blister pack 151 can be held and tilted to place the drug dosage form 67, on an oral mucosal membrane. FIGS. 16E and 16F show blister pack 151 type packaging with a handle 131 shaped like a flower or an animal, respectively, to be used for single dose applicator 123 designed for pediatric use. Other single dose applicator shapes could include cartoon characters, animals, super-heroes or other appropriate shapes for pediatric applications.

Figure 18A:
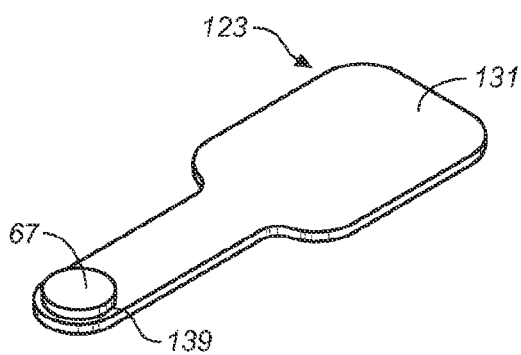
FIGS. 18A-C provide an illustration of additional single dose applicator and multiple dose applicator embodiments.
Figure 18B:
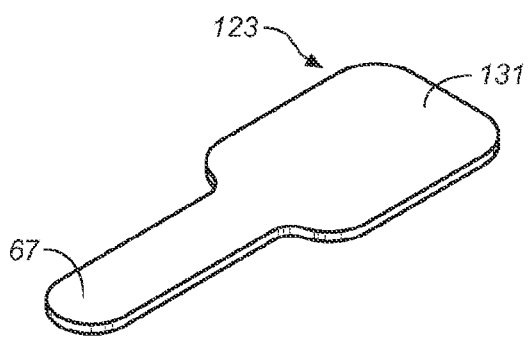
Figure 18C:
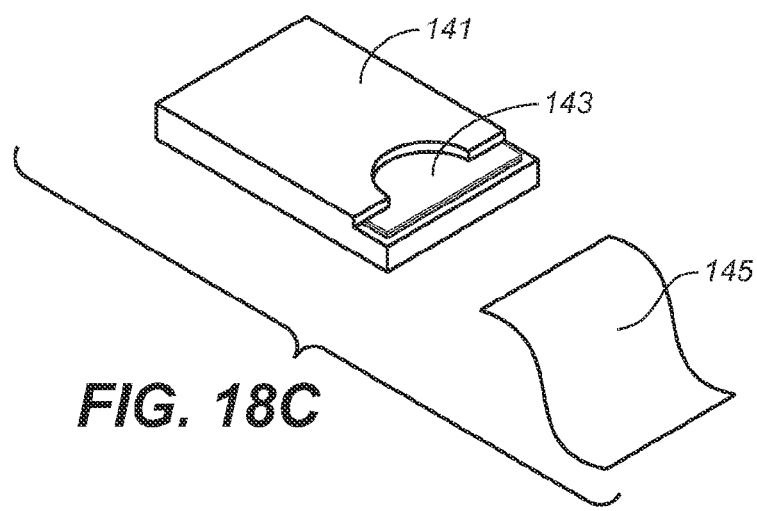

FIG. 18A shows a flat rigid applicator 123 with a dosage form 67 adhered to one end, for example, by means of a rapidly dissolving ingestible adhesive material such that when the applicator end with the dosage form is placed under the tongue, the adhesive dissolves, the dosage form 67 is placed on an oral mucosal membrane, such as in the sublingual space, and the applicator can be removed. FIG. 18B shows an applicator 123 made from a water permeable material, impregnated with drug, forming a material and dosage from matrix. When the impregnated end of this applicator 123 is placed under in the mouth on an oral mucosal membrane, the moisture in the saliva dissolves the drug and delivers it transmucosally. FIG. 18C shows dissolving film dosage forms 145 and a dosage form package with a plurality of dissolving film dosage forms 143 within it. The dissolving film dosage form 143 is removed from the package 141 and placed on an oral mucosal membrane, e.g., in the sublingual space where it dissolves and delivers the drug transmucosally.

Figures 19A, 19B:
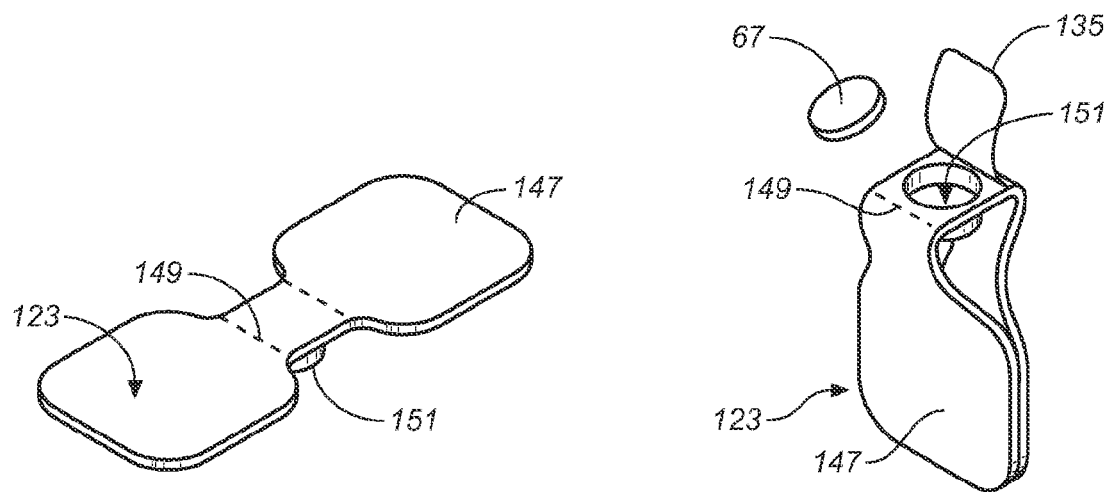
FIGS. 19A-B provide an illustration of two stages of use of one embodiment of a single dose applicator.
Figure 20A:
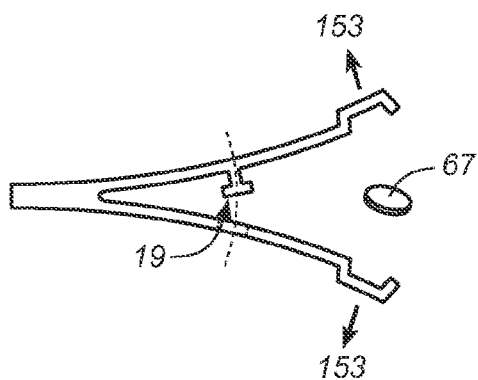
FIGS. 20A-20D are schematic depictions of additional examples of single dose applicators (SDAs).
Figure 20B:
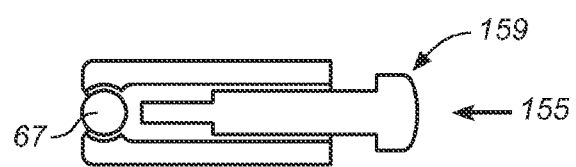
Figure 20C:
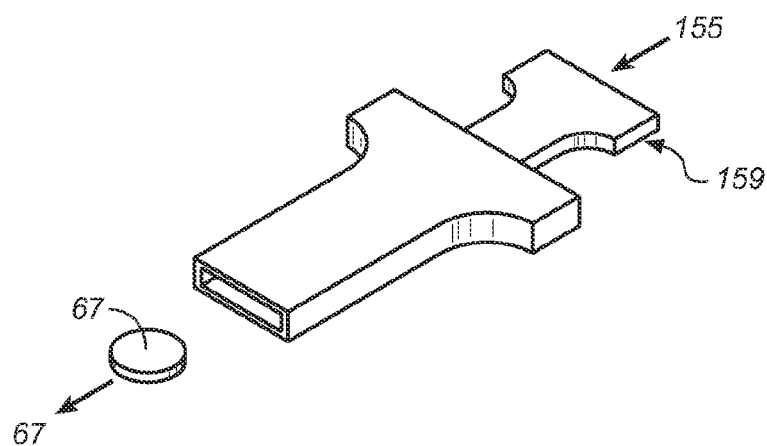
Figure 20D:
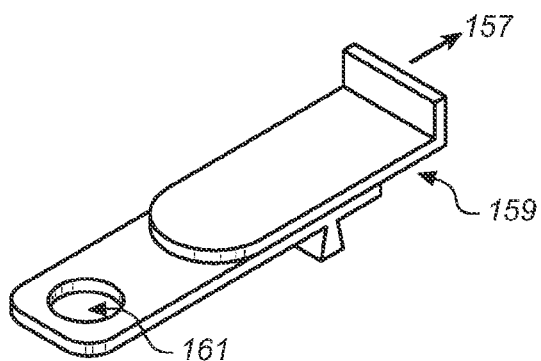
Figure 21A:
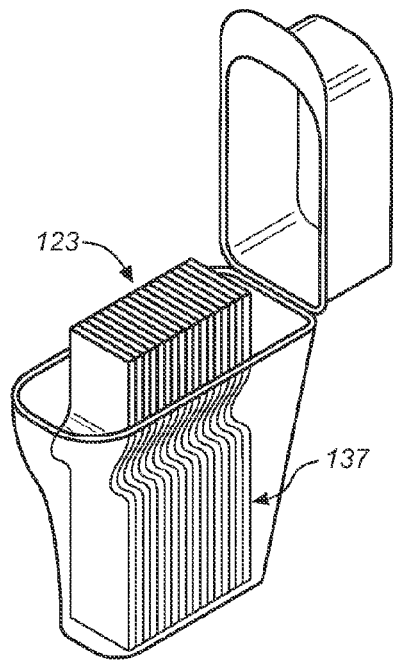
FIGS. 21A-21D provide a schematic depiction of a multiple dose applicator or container which provides for storage of a plurality of SDAs prior to use, and the use of the SDAs for sublingual administration of a drug dosage form.
Figure 21B:
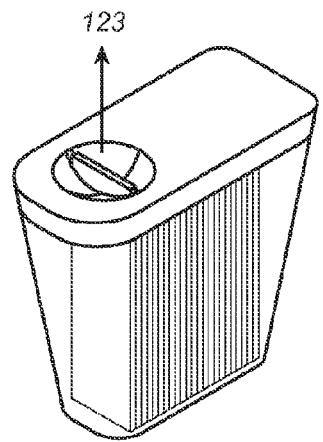
Figure 21C:
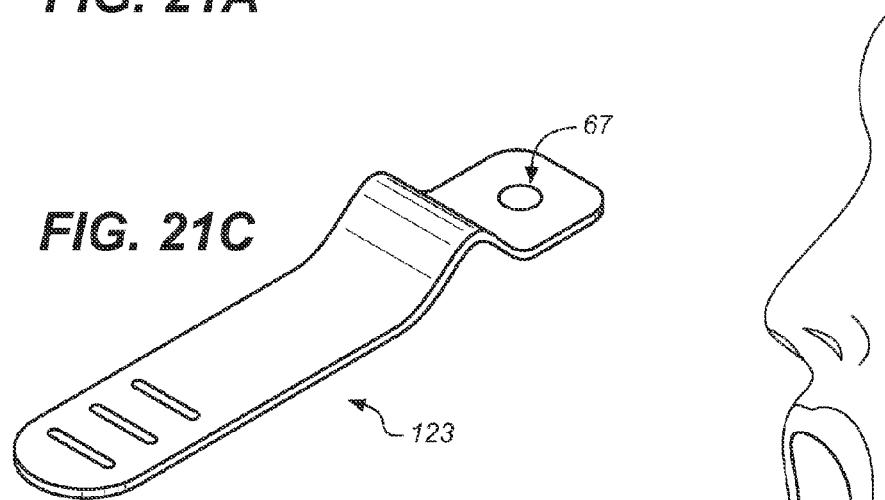
Figure 21D:
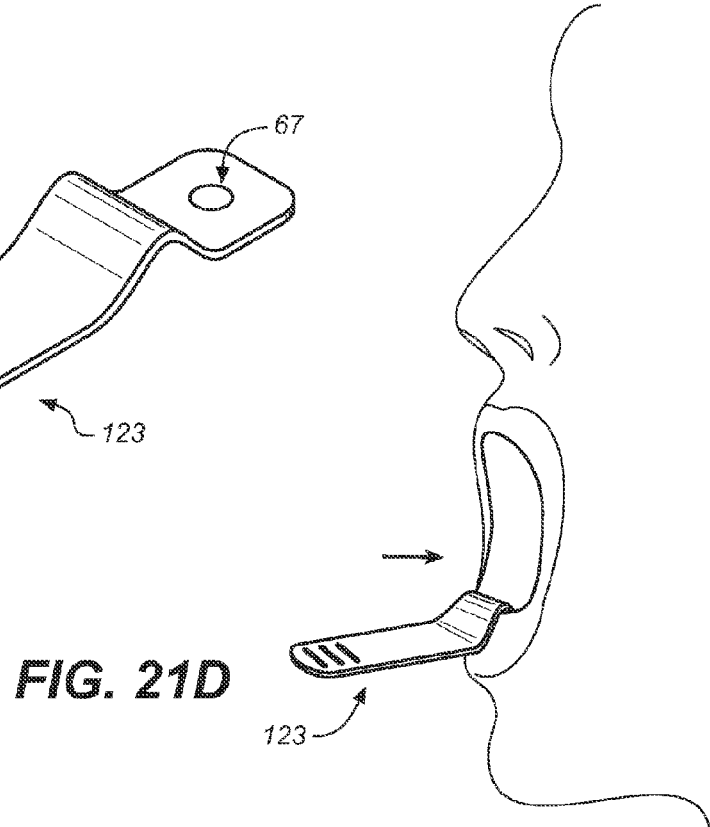

FIGS. 19A-B provides an illustrations of two stages of use of one embodiment of a single dose applicator 123. FIG. 19A shows the applicator 123 in its configuration prior to use, with two applicator tabs 147, two perforations 149, and a blister pack 151 containing a dosage form 67. In order to administer the dosage form 67, the two applicator tabs 147 are bent downward at the perforations 149, forming a handle 131, and the seal 135 is peeled back to reveal the blister pack 151 and allow the dosage form 67 to be dropped on an oral mucosal membrane, e.g., in the sublingual space.

In another embodiment, a drug dispensing device of the invention may contain a plurality of SDA's, in a cartridge or individually packaged, and may dispense a single SDA containing a single drug dosage form for use by the patient, healthcare provider, or user. The drug dispensing device may dispense single SDA's in the same way and with the same features as would be advantageous for the dispensing of single drug dosage forms described in the invention.

In yet another embodiment the multiple dose applicator 137 is a device which comprises one or more drug dosage forms 67 or single dose applicators 123, a portable power means, like a battery, a printed circuit board, a data connectivity means, and a user interface. In this embodiment the drug dispensing device may include the ability to perform one or more of the following functions: record drug dosage dispensing history, check user identification by means of fingerprint identification, RFID, voice recognition, etc., allow the dosage history to be transferred to another device, computer or network, and/or provide a lockout period between dose dispenses.

Figure 17:
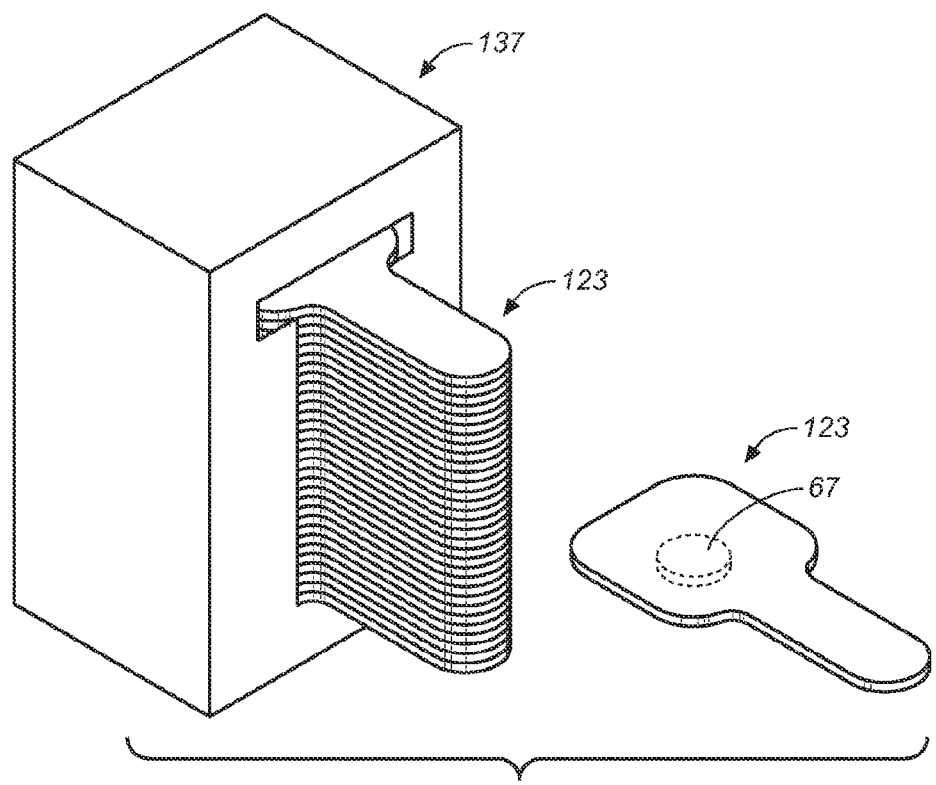
FIG. 17 provides an illustration of a multiple dose applicator where a plurality of single dose applicators are stored prior to use.

FIG. 17 is a schematic depiction of an exemplary multiple dose applicator 137 for delivering dispensing drug dosage forms 67, each individually packaged in a single dose applicator 123.

FIGS. 20A-20D are schematic depictions of additional examples of SDAs, including a tweezer or reverse scissor-type SDA (20A), where a drug dosage form 67 is held between the two sides 153 of the SDA 123 such that when the latch 19 is released, the drug dosage form 67 is no longer held by the SDA and can be placed on an oral mucosal membrane by the user; a syringe-type SDA (20B) with a circular channel, where a drug dosage form 67 is pushed out of the end of the channel when a user pushes 155, the slider or plunger 159; a pusher-type SDA (20C) with a rectangular channel where a drug dosage form 67 is pushed out of the end of the channel when a user pushes 155, the slider 159; or a slider-type SDA (20D) where drug dosage form 67 is held in a pocket 161 and the drug dosage form 67 becomes accessible when a user pulls 157 a slider 159.

FIGS. 21A-21D provide a schematic depiction of a multiple dose applicator (MDA) 137 or container for storage of a plurality of SDAs 123 prior to use (21A); where in the exemplified embodiment, there is a slot in the upper cover of the MDA 137 for removal of individual SDAs 123 (21B); such that each individual SDA 123 comprises a drug dosage form 67 (21C); and the SDA 123 facilitates placement of the drug dosage form 67 under the tongue in the sublingual space (21D).

Figure 7:
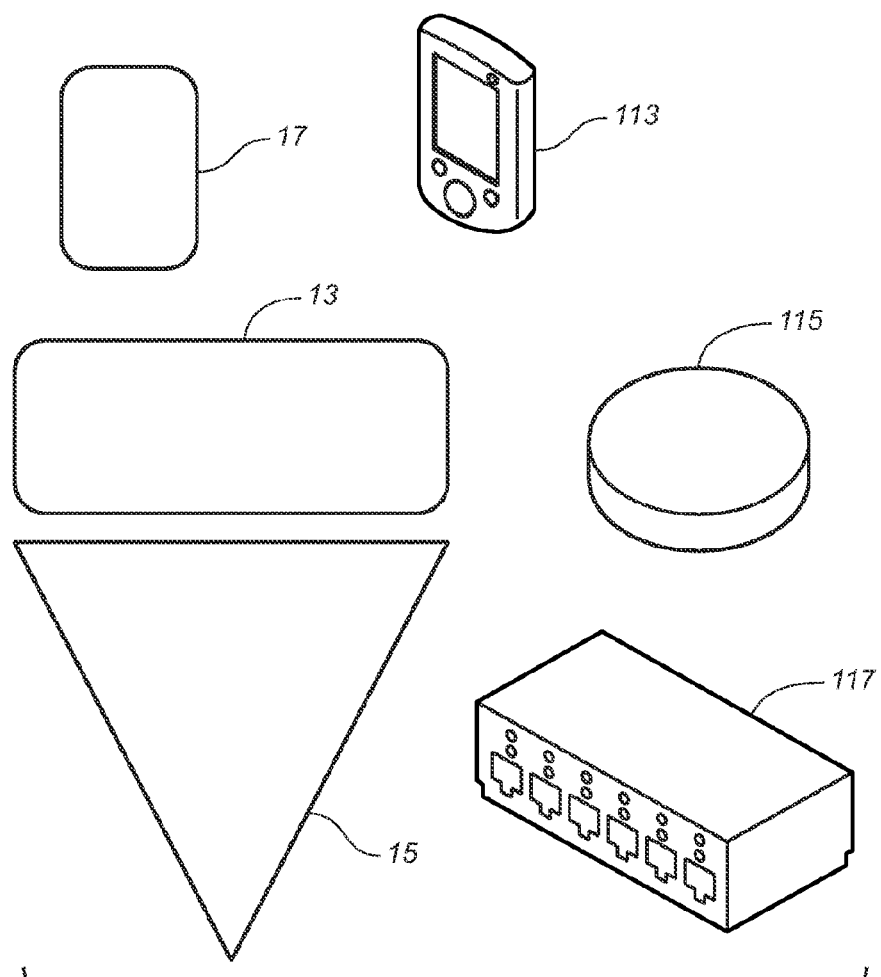
FIG. 7 is a schematic architecture connection diagram illustrating the various components that may be included in a drug dispensing device or system.

VII. Methods and Systems for Delivering Small Volume Dosage Forms Using a Device Methods and systems for delivering small volume dosage forms, e.g. sufentanil-containing dosage forms using a device are provided. FIG. 7 provides a schematic architecture connection diagram illustrating the various components that may be included in a dispensing device or system for dispensing small volume drug dosage forms, including a device with a separate head 13, body 15 and cartridge 17, a portable docking fob 113, Patient RFID 115 and a base station 117.

Figure 8A:
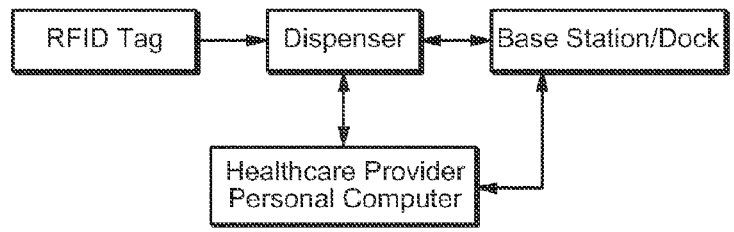
FIG. 8A is a block diagram illustrating one aspect of communication in the drug dispensing system, including an RFID tag, a drug dispensing device, a base station/dock and a healthcare provider personal computer.

A block diagram illustrating one aspect of communication in a drug dispensing system, including an RFID tag, a drug dispensing device, a base station/dock and a healthcare provider personal computer system wherein a drug dispensing device can communicate with the physician or care giver, via the dock, or by means of a wired or wireless communication method is provided in FIG. 8A.

Figure 8B:
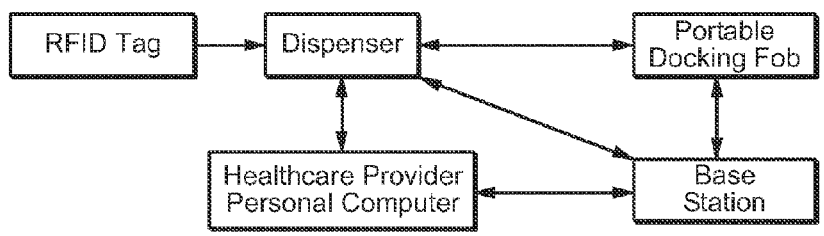
FIG. 8B is a block diagram illustrating another aspect of communication in a drug dispensing system, including an RFID tag, a drug dispensing device, a portable docking FOB, a base station and a healthcare provider personal computer.

A block diagram illustrating another aspect of communication in a drug dispensing system, including an RFID tag, a drug dispensing device, a portable docking fob, a base station and a healthcare provider personal computer is provided in FIG. 8B. The drug dispensing device may communicate with the physician or care giver, via the FOB, by means of a wired or wireless communication method to provide usage information and information regarding the respiratory status or blood pressure of the patient to the physician at regular intervals. The FOB can be adapted to attach to a cord so as to allow the fob to hang from the neck of the physician or caregiver.

Exemplary features of the dispensing device include the following: In one embodiment, the head, body, and cartridge comprise the handheld portion of the device. This device assembly has a latch to disconnect the head and body, and a dispense button for patient use. The device also has lights to show lock-out status, errors, and power. In this embodiment, the cartridge which contains the drug dosage forms and the body are used a single time only.

The system may comprise a portable dock which is handheld, independent of the patient device and solely for healthcare professional use. The dock enables higher level feature use such as deeper queries into patient device use, the ability to upload device data, unlocking of the head/body and the tether, lockout override for dosing the patient, and a larger reading display. The dock is also used to setup and take down the patient device.

The system may also comprise an RFID bracelet that is activated via the dock and is worn by the patient to establish and control dosing to correct patient and to that patient alone. This feature prohibits use of the device by others.

The system may further comprise a recharging base used to charge the dock and heads and is also used to update the heads and docks when new software becomes available or when new users are programmed into the system.

The drug dosage forms are typically provided in single use disposable cartridges which are loaded into the device prior to administration.

Exemplary set-up instructions for the device include the following steps:

The device head and dock are charged on the recharging station.

The device body and wristband are removed from the packaging.

The device head and dock are removed from the charging station.

The cartridge is loaded into the body by inserting a cartridge into the device body as indicated ensuring that the cartridge "clicks" and is locked in place.

The device body (with cartridge) is assembled onto the head.

The power button on the assembled device is pushed to power-up the system.

The power button on the dock is pushed to power-up the dock.

The assembled device is plugged into the dock.

A healthcare professional scans their fingerprint or inputs a unique password in order to unlock the dock.

The device reads the label on the cartridge and the dock displays setup information, for example, the drug name, the quantity of tablets, the drug concentration, the preset lockout time, the duration of use (72 hours), and the battery status of the head.

After the information is read from the cartridge and displayed on the dock, the healthcare professional will be requested to confirm that all information is correct and will require a witness to verify the information.

The dock will require that the patient wristband be paired to the device by bringing the wristband close to the device.

The device will read the band and request confirmation of the band number; selection and confirmation of the number The patient ID is entered into the dock. i.e. patient medical record number The wristband is placed on the patient's hand that will be used to operate device.

Then, the dock will indicate that it is ready to dispense a plastic initialization tablet or "shipping tablet".

Upon confirmation, the device will dispense a plastic initialization tablet or "shipping tablet". This step is used by the device to calibrate the dispensing mechanism, initiate the cartridge for use, and allows the healthcare professional to verify proper use and to train the patient with a "shipping" or placebo-type tablet.

Once the plastic initialization tablet or "shipping tablet" is dispensed, the dock will require the healthcare professional to confirm that the plastic tablet was dispensed.

After confirmation, the display will indicate that the device is ready for use.

In some cases, a tether can be connected to the device via the dock. The dock will allow the healthcare professional to lock and unlock the tether as required.

If a patient will self administer a drug dosage form using the device, the patient will be trained prior to use.

Exemplary use of the claimed devices and systems is provided in Examples 6-8.

VIII. In Vivo Human Studies

Provided herein is pharmacokinetic data obtained in animals and humans based on studies where sufentanil and alfentanil were administered via the sublingual route using the claimed small volume dosage forms.

A human clinical study was performed using healthy volunteers. The study which is detailed in Example 1 below was performed with 12 subjects (6 men and 6 women) using sublingual sufentanil dosage forms containing either 2.5 mcg, 5 mcg or 10 mcg of sufentanil base corresponding to 3.7 mcg, 7.5 mcg or 15 mcg of sufentanil citrate, respectively (see Table 1). All excipients were "pharmaceutically acceptable" (inactive and have GRAS or "generally recognized as safe" status.

Sufentanil dosage forms designed for sublingual use were compared to IV sufentanil, administered through an IV catheter as a continuous infusion over 10 minutes. Plasma samples were drawn from a different IV catheter at a remote location. The assay demonstrated good inter-day precision and accuracy at the high, medium and low quality control sample concentrations.

The dosage forms for this study eroded over a period of 10-30 minutes in all subjects. After placement of each sufentanil dosage form in the sublingual cavity of the 12 healthy volunteers, a remarkably consistent pharmacokinetic profile was obtained (see FIG. 9 and Table 2). The bioavailability compared to IV administration for single administration of all three dosages averaged 91%, which is far superior to that measured for commercially available fentanyl transmucosal preparations, Actiq and Fentora (47% and 65%, respectively—Fentora package insert). Although this high bioavailability could be due to a number of factors including but not limited to erosion time, it is likely that the lack of saliva produced by the small size of the dosage forms limits the swallowing of the drug and avoids the low bioavailability typical of drug absorption via the GI route. Both Fentora and Actiq package inserts claim at least 50% and 75% of the drug dose, respectively, is swallowed via the saliva, and both exhibit lower bioavailability than the claimed dosage forms.

The dosage forms used in this clinical trial had a volume of approximately 5 microliters (mass of 5.5-5.85 mg), a small fraction of the size of Actiq or Fentora lozenges. The dog studies described in Example 4 demonstrate that sufentanil has very poor GI bioavailability (12%), therefore, given the high bioavailability of the sufentanil dosage forms, wherein drug is administered by the oral transmucosal route, the data supports the conclusion that greater than 75% of the drug is absorbed transmucosally. Therefore, less than 25% of the drug is swallowed, which is a much lower percentage than is swallowed with Fentora or Actiq.

Importantly, this bioavailability is also linked to the consistency of total drug delivered to the patient. For example, the total plasma drug area under the curve (AUC 0-infinity) for sufentanil dosage forms 10 mcg was 0.0705±0.0194 hr* ng/ml (mean±standard deviation (SD)). This SD is only 27.5% of the total AUC. Coefficient of variation (CV) is a term to describe the percent SD of the mean. The coefficient of variation for the fentanyl products, Fentora (AUC is 45%) and Actiq (AUC is 41%; Fentora package insert), while the coefficient of variation for the claimed sublingual sufentanil dosage forms is less than 40%. Therefore, the total dose delivered to the subject is not only more bioavailable for the sufentanil dosage forms but it is more consistent.

The sufentanil sublingual dosage forms are also superior in terms of consistent drug plasma levels early after administration. The $C_{max}$ obtained with the mcg sufentanil dosage form was 27.5±7.7 pg/ml. The coefficient of variation of the $C_{max}$ is therefore only 28%. The $C_{max}$ for Fentora and Actiq suffer from variability of GI uptake of drug. Fentora reports a $C_{max}$ of 1.02±0.42 ng/ml, therefore the coefficient of variation of the $C_{max}$ is 41%. The range of coefficients of variation for the various doses of Fentora is from 41% to 56% (package insert). Actiq coefficient of variation of $C_{max}$ is reported as 33% (Fentora package insert).

In addition to superior bioavailability and consistency in plasma concentrations, the time to $C_{max}$, also referred to as $T_{max}$, is important since quick and consistent onset of pain relief is important in the treatment of acute pain. The $T_{max}$ for 10 mcg sufentanil dosage forms was 40.8±13.2 minutes (range 19.8±60 minutes). The reported average $T_{max}$ for Fentora is 46.8 with a range of 20-240 minutes. The $T_{max}$ for Actiq is 90.8 minutes, range 35-240 minutes (Fentora package insert). Therefore, the consistency in onset of analgesia for sufentanil dosage forms is markedly improved over Fentora and Actiq, with a 400% decrease in the slowest onset of $T_{max}$.

Important in the treatment of acute pain, especially acute breakthrough pain, is a consistent and relatively short half-life of the drug. The plasma elimination half-life of the 10 mcg sufentanil dosage form was 1.71±0.4 hours, which allows the drug to be titratable for various levels of pain. If the breakthrough pain event lasts longer than 1.5 hours then the patient can dose with another dosage form. The plasma elimination half-life of Actiq and Fentora are 3.2 hours and 2.63 hours, respectively, for the lowest doses. The half-lives for the higher doses increase substantially for these drugs, thereby limiting the titratability of these drugs.

Although still in development, published data allows comparison of the sufentanil pharmacokinetic data provided herein to that of Rapinyl, a fentanyl sublingual fast-dissolve lozenge. As previously mentioned, the observed bioavailability for the claimed sufentanil dosage averaged 91% as compared to the published bioavailability for Rapinyl which is approximately 70% (Bredenberg, New Concepts in Administration of Drugs in Tablet Form, Acta Universitatis Upsaliensis, Uppsala, 2003). The coefficient of variation of the AUC (0-infinity) for Rapinyl ranges from 25-42% depending on dose, whereas the coefficient of variation for the claimed 10 mcg sufentanil dosage forms is 27.5%. This high bioavailability would suggest that regardless of dose, the sufentanil dosage forms have a consistently low coefficient of variation of AUC, whereas this is not true for Rapinyl. In fact, the coefficient of variation around the AUC for all three doses of sufentanil exemplified herein (2, 5, and 10 mcg) averaged 28.6%, demonstrating that the observed low coefficient of variation is not dependent on dose.

The coefficient of variation of the $C_{max}$ for Rapinyl varies from 34-58% depending on dose. As shown by the data presented herein, administration of the 10 mcg sufentanil dosage form resulted in a $C_{max}$ with a coefficient of variation of only 28%, and the average coefficient of variation of $C_{max}$ for the 2, 5, and 10 mcg doses was 29.4%, indicating minimal variability depending on dose. Similarly, the coefficient of variation for $T_{max}$ with Rapinyl ranges from 43-54% depending on dose, whereas for our sufentanil dosage forms, this coefficient of variation for $T_{max}$ averages only 29% over all three dosage strengths. This consistent onset of action achieved with sublingual sufentanil dosage forms allows a safer redosing window when compared to any of the three comparator drugs, since rising plasma levels are contained to a shorter period.

Additionally, as with Fentora and Actiq, Rapinyl demonstrates a longer plasma elimination half-life (5.4-6.3 hours, depending on dose) than the claimed sufentanil dosage forms. The plasma elimination half-life of sufentanil dosage forms ranged from 1.5-2 hours following a single oral transmucosal administration in humans (Table 2), which allows for more titratability and avoids overdosing. As will be understood by those of skill in the art, the half-life described herein for the exemplified dosage forms may be adjusted by modification of the component and relative amounts of the excipients in the formulation used to make a given dosage form. The ability to titrate to higher plasma levels by administering repetitive doses of the sublingual sufentanil dosage forms was also tested in this human study.

Repeat dosing of 5 mcg dosage forms every 10 minutes for four dosings resulted in a bioavailability of 96%, indicating that repetitive dosing to achieve higher plasma levels while still maintaining high bioavailability is possible. Whether treating post-operative pain or cancer break-through pain, being able to efficiently titrate to an individual's own level of pain relief is important.

Another aspect of the PK curves generated by sublingual sufentanil dosage forms is the plateau phase, which allows for a period of consistent plasma levels, which is important for both safety and efficacy. Compared to either IV bolus administration (see Animal Studies Examples 2-5) or the 10 minute IV infusion in our human study (Example 1 and FIG. 9), the PK profile for the sufentanil dosage forms is clearly safer. Rapid, high $C_{max}$ plasma levels are avoided. Given the ability of opioids to produce respiratory depression, avoiding these high peaks in the PK profile is advantageous.

An important mathematical ratio that demonstrates the prolonged plateau phase of the measured blood plasma levels of sufentanil following administration of a dosage form is the time spent above 50% of $C_{max}$ divided by the known IV terminal elimination half-life of the drug:

$$\text{Therapeutic Time Ratio} = \frac{\text{Time of offset of } C_{max}/2 - \text{Time of onset of } C_{max}/2}{IV \text{ Elimination Half-Life of the Drug}}$$

The elimination half-life is an intrinsic property of the molecule and is measured most reliably using the IV route to avoid contamination from continued uptake of drug from the sublingual route. The IV elimination half-life for 5 mcg of sufentanil in our human study was 71.4 minutes due to the detection limits of the assay at these low doses. The published IV elimination half-life for sufentanil at much higher doses is 148 minutes, due to detection of both the rapid alpha-elimination mechanism of redistribution and the longer beta phase of elimination via metabolism and excretion. This published elimination half-life is more accurate and more appropriate to use in the above equation. The time spent above 50% of $C_{max}$ on average for the 12 volunteers for the 2.5, 5 and 10 mcg dosage strengths was 110 minutes, 111 minutes and 106 minutes, respectively. Therefore, the Therapeutic Time Ratio for these specific sufentanil dosage forms ranged from 0.72-0.75. As the formulation of the dosage forms is varied, erosion time of the dosage form will be either decreased or increased, and one might see a range of Therapeutic Time Ratios from approximately 0.2-2.0 for sufentanil.

The Therapeutic Time Ratio is a measure of how successfully short-acting drugs are formulated to produce an increase in therapeutic time and increase safety by avoiding high peak plasma $C_{max}$ concentrations. For example, as a comparison, the sufentanil IV arm of the human study demonstrated a Therapeutic Time Ratio of 10 min/148 min=0.067. This low ratio value for the IV arm, therefore, is a measure of the high peak produced by IV infusion of sufentanil and demonstrates that this formulation does not produce a significant plateau phase. There is a 10-fold higher Therapeutic Time Ratio for the sufentanil formulations listed in Table 1 (the dosages used in the human study) versus IV sufentanil, indicating a prolonged therapeutic plateau profile for these formulations.

The uptake of transmucosal medications via small volume drug dosage forms results in a more consistent drug delivery between individual dosages and individual patients as compared to that of currently available oral transmucosal dosage forms for which a large fraction of drug uptake occurs via the GI route.

The methods and systems described herein are designed to work effectively in the unique environment of the oral cavity, providing for higher levels of drug absorption and pain relief than currently available systems. The claimed methods and systems are designed to avoid the high peak plasma levels of intravenous administration by entry into the circulation via the sublingual mucosa.

The claimed methods and systems further provide for independent control of bioadhesion, dosage form disintegration (erosion) and drug dissolution and release over time, together with administration using a device to provide a safe delivery profile. The device-administered oral transmucosal dosage forms provide individual, repetitive doses that include a defined amount of the active agent (e.g., sufentanil), thereby allowing the patient or care giver to accurately titrate the amount of drug delivered and to adjust the amount as appropriate in a safe and effective manner. The lock-out feature of the dispensing device adds to the safety of the drug delivery profile.

An advantage of the oral transmucosal dosage forms herein is that they exhibit high consistent bioavailability and can maintain the plasma drug concentration within a targeted therapeutic window with significantly lower variability for a longer duration than currently available medications or systems for treatment of pain. The high peak plasma levels typically observed for IV dosage forms are blunted following administration of sufentanil-counting dosage forms. In addition, a rapid decline in plasma levels is avoided since the drug is continually crossing from the oral cavity into the bloodstream during the length of time of erosion of the dosage form or longer, thus providing plasma pharmacokinetics with an extended plateau phase as compared to the IV route of administration. Further, treatment with the claimed methods and systems provides for improved safety by minimizing the potentially deleterious side effects of the peaks and troughs in the plasma drug pharmacokinetics, which are typical of currently available medications or systems for treatment of pain.

Advantages of the claimed sublingual dosage forms over various liquid forms for either sublingual or intranasal administration include local release of drug from the dosage form over time with minimal swallowing of liquid drug via either the nasal or oral/GI route. Published pharmacokinetic data following administration of intranasal sufentanil liquid (15 mcg) in humans demonstrates a bioavailability of 78% (Helmers et al., Canadian Journal of Anaesthesia 36:494-497, 1989). Sublingual liquid sufentanil administration (5 mcg) in Beagle dogs (see Example 4 below) resulted in a bioavailability of 40%. The aforementioned bioavailability data are less than the 91% average bioavailability that was obtained in human volunteers using sufentanil administered sublingually in the form of a small volume dosage form (see Example 1 below).

Due to the small size of the oral transmucosal dosage forms, repeated placement in the sublingual cavity over time is possible. Minimal saliva production and minimal physical discomfort occurs due to the small size, which allows for repetitive dosing over days to weeks to months. Given the lipid profile of the sublingual cavity, the sublingual route, also allows for slower release into the plasma for certain drugs, such as sufentanil, which may be due to utilization of a "depot" effect that further stabilizes plasma levels compared to buccal delivery.

The oral transmucosal dosage forms are designed to fit comfortably under the tongue such that the drug form erodes sufficiently slowly to avoid the immediate peak plasma levels followed by significant drop off seen in prior art formulations such as described in U.S. Pat. No. 6,759,059 (Rapinyl), wherein fentanyl was administered via tablets containing 400 mcg of fentanyl which resulted in a peak plasma level of 2.5 ng/ml followed by an immediate drop in plasma level. Fentora (fentanyl buccal tablet) also suffers from a lack of a plateau phase but rather has a steep incline up to the $C_{max}$ followed by a significant drop-off in plasma levels (Fentora package insert).

Animal Studies

A series of studies in awake, alert Beagle dogs was performed to more fully elucidate the properties of small volume oral transmucosal dosage forms using various drugs and formulations. A comparison of the claimed system for oral transmucosal administration of sufentanil relative to administration of liquid sublingual sufentanil or swallowed sufentanil dosage forms was made to evaluate various attributes of the drug dosage forms. The results support the claim that the small, volume drug dosage forms of the invention are well tolerated sublingually (as demonstrated by use in awake dogs) and result in higher bioavailability and more consistent pharmacokinetic data than other oral transmucosal dosage forms, including instilled liquids.

The first Beagle dog study was carried out to compare a sublingual 5 mcg sufentanil dosage form to IV sufentanil as described more fully in Example 2 below. A total of three Beagle dogs were studied and the results are graphed in FIG. 10 and tabulated in Table 3. The bioavailability of the sublingual sufentanil dosage forms was 75% compared to IV. Therefore, similar to the human data, this bioavailability data in dogs confirms the superior attributes of the dosage forms over larger dosage forms. Furthermore, similar to the human data, the coefficient of variation for the AUC was low, 14%, compared to the variation of other commercial transmucosal dosage forms. The Therapeutic Time Ratio of the sublingual sufentanil dosage forms is 0.28 whereas the Ratio for IV sufentanil is 0.05 (using the published IV elimination half-life of sufentanil in dogs of 139 minutes). Therefore, similar to humans, the 5 mcg dosage form in Table 1 resulted in a much higher Therapeutic Time Ratio (5.6-fold) compared to IV sufentanil in dogs.

Additional studies determined the effect of varying the formulation on the pharmacokinetic profile. This study is explained more fully in Example 3 below. By prolonging the erosion time of the dosage form, the plasma half-life was extended from 33 minutes for the medium disintegrating formulation (in Example 2) to 205 minutes. The Therapeutic Time Ratio was increased from 0.28 to 1.13 for the slow disintegrating dosage forms. This study illustrates the flexibility of the small volume dosage forms, and the ability based on excipient selection, to alter the PK of the drug. This flexibility is possible due to the small size of the dosage forms, which allows either short or prolonged contact time with the sublingual mucosa without dislodging or creating excess saliva which would prematurely wash the drug into the GI tract.

Another study in Beagle dogs was performed to evaluate the advantages of the sublingual dosage form over liquid administration sublingually. This study is described more fully in Example 4 below. The results indicate that although delivery of sufentanil (5 mcg) in an instilled liquid form to the sublingual cavity results in rapid $T_{max}$, this method of drug administration results in very low bioavailability (40%) compared to sublingual sufentanil dosage forms (75%). This is probably due to swallowing of the liquid drug. Moreover, the AUC is extremely variable, as shown by the high coefficient of variation (82%). The $C_{max}$ is also highly variable with this method of drug administration, demonstrating a coefficient of variation of 72%. The Therapeutic Time Ratio for instilled liquid sufentanil sublingually was calculated as 0.06, very similar to the IV sufentanil arm for this study which demonstrated a Ratio of 0.03. Therefore, this instilled sublingual liquid profile does not provide the advantageous therapeutic plateau observed with the sublingual dosage forms. These findings support that the high sublingual bioavailability observed from different formulations is not intrinsic to the molecule but rather it is a direct result of the unique design of the dosage form and its formulation. The strong adherence of the small dosage forms s to the oral mucosa in the sublingual cavity minimizes the variability in the surface area available for absorption, as is the case of a liquid solution, thus improving delivery of the molecule to the systemic circulation. In addition, owing to its unique design and small dimensions, the dosage forms does not elicit significant saliva production, thus reducing the potential for ingestion of the released drug. Both factors contribute to the higher and more uniform drug absorption from the sublingual cavity.

An additional part of this study in Example 4 was the determination of the bioavailability of swallowed sufentanil dosage forms. Since there is little to no data on sufentanil GI bioavailability in the literature, it was important to further evaluate the low bioavailability of this route of administration to further support the observation that drug from the sublingual dosage forms could not be swallowed and maintain a high bioavailability. As indicated by the PK analysis data in Table 7, oral bioavailability of sufentanil from the swallowed dosage forms is very low, approximately 12%. In addition, as predicted from the known erratic GI uptake of fentanyl, the swallowed dosage forms demonstrated extremely high variability both in the amount of drug absorbed (AUC) and the pharmacokinetics of absorption ($C_{max}$, $T_{max}$) as shown in Table 7. These data support the conclusion that bioadhesive sublingual dosage forms strongly adhere in the sublingual cavity in such a manner that they don't dislodge, thus avoiding oral ingestion and avoiding the high variability of plasma levels which is typical when drug is absorbed via the GI route.

Additional studies evaluating alfentanil, formulated into small volume dosage forms were performed in Beagle dogs and are more fully described in Example 5 below.

Alfentanil dosage forms resulted in a bioavailability of 94% compared to IV alfentanil and a coefficient of variation of 5% for the AUC, 7% for $C_{max}$ and 28% for $T_{max}$. The Therapeutic Time Ratio was calculated as 0.33, compared to 0.04 for the IV alfentanil arm of this study (calculated using a published IV elimination half-life of 104 min for alfentanil in dogs). Therefore, the alfentanil formulation (as described in Example 5) produces an 8-fold improved Therapeutic Time Ratio over the IV alfentanil arm. The high bioavailability of this formulation again supports the claim that minimal swallowing of drug occurs with use of the dosage forms.

VIII. Utility of Small-Volume Oral Transmucosal Dosage Forms

The claimed dosage forms find utility in delivery of any drug that can be administered by the oral transmucosal route. The small volume oral transmucosal dosage forms provide for high bioavailability, low variability in $T_{max}$, low variability in $C_{max}$ and low variability in AUC. The dosage forms also provide for prolonged plasma levels within the therapeutic window.

In one exemplary embodiment described in detail herein, the dosage forms find utility in treating a subject suffering from pain that may be associated with any of a variety of identifiable or unidentifiable etiologies. In this embodiment, the dosage forms find utility in suppression or mitigation of pain. The term "treatment" or "management" of pain is used here to generally describe regression, suppression, or mitigation of pain so as to make the subject more comfortable, as determined for example by pain score.

The invention finds utility in the treatment of both opioid naïve patients and opioid tolerant patients.

The term "opioid naïve patient" is used herein with reference to a patient who has not received repeated administration of an opioid substance over a period of weeks to months.

The term "opioid tolerant patient" as used herein means a physiological state characterized by a decrease in the effects of an opioid substance (e.g., analgesia, nausea or sedation)

with chronic administration. An opioid substance is a drug, hormone, or other chemical substance that has analgesic, sedative and/or narcotic effects similar to those containing opium or its derivatives. If analgesic tolerance develops, the dose of opioid substance is increased to result in the same level of analgesia. This tolerance may not extend to side effects and side effects may not be well tolerated as the dose is increased.

The dosage forms find particular utility in the treatment of acute pain or other conditions "in the field", i.e., under highly sub-optimal conditions. Paramedics or military medics often are required to treat severe acute pain or other injuries or conditions in non-sterile situations, where needles used for IV or IM administration can result in unintended needle sticks, risk of infection, etc. Oral opioid tablets often take 60 minutes to provide relief which is too long for someone in severe pain. The claimed dosage forms find utility in addressing this need.

When the dosage forms are used for the treatment of pain, the claimed methods and systems find utility in administration of drugs to pediatric and adult populations and in treatment of human and non-human mammals, as well as in opioid tolerant and opioid naïve patient populations.

Application of the claimed methods and systems is not limited to any particular therapeutic indication. As such, the claimed dosage forms find utility in administration of drugs to pediatric and adult populations and in the treatment of human and non-human mammals.

The dosage forms find utility in pediatric applications, since the comfortable and secure nature of the dosage form allows children to readily accept this mode of therapy and will reliably deliver drug transmucosally. Specific examples include, but are not limited to, treatment of pediatric acute pain when IV access is not available or inconvenient, treatment of pediatric asthma when the child is not able to use an inhaled route of administration effectively, treatment of nausea when a child can not or will not swallow a pill, pre-procedural sedation when a child is NPO (no oral intake allowed) or a more rapid onset is required.

The dosage forms find further utility in veterinary applications. Specific examples include, but are not limited to, any treatment of an acute condition for which IV administration is not readily available or inconvenient, such as pain relief, anxiety/stress relief, pre-procedural sedation, etc.

The following examples are provided to illustrate the invention and are not intended to limit any aspect of the invention as set forth above or in the claims below.

The dosage forms for the dosage forms described above can be tested for in vivo drug pharmacokinetics in both humans and a suitable animal model following sublingual administration.

The following examples demonstrate the ability of the dosage forms to allow a consistent absorption profile of sufentanil citrate following sublingual administration in human volunteers and awake, alert Beagle dog model.

Example 1

Sublingual Sufentanil dosage forms Administered Sublingually in Adult Human Volunteers

TABLE 1

| | Sufentanil Formulations Used in the Human Clinical Study | | | | | | | | |
|---|---|---|---|---|---|---|---|---|---|
| | #46 2.5 ug Sufentanil Base | | | #47 5.0 ug Sufentanil Base | | | #48 10.0 ug Sufentanil Base | | |
| Ingredient | Mass in Batch (g) | Mass in tablet, mg | % Mass in tablet, w/w | Mass in Batch (g) | Mass in tablet, mg | % Mass in tablet, w/w | Mass in Batch (g) | Mass in tablet mg | % Mass in tablet, w/w |
| Sufentanil Citrate | 0.3750 | 0.00375 | 0.068 | 0.75 | 0.0075 | 0.136 | 1.50 | 0.0150 | 0.273 |
| Mannitol 200SD | 406.60 | 4.066 | 73.931 | 406.3 | 4.063 | 73.866 | 405.50 | 4.055 | 73.727 |
| Poloxamer (Lutrol F68) | 11 | 0.110 | 2.000 | 11 | 0.110 | 2.000 | 11 | 0.110 | 2.00 |
| Polyox WSR 303 | 16.5 | 0.165 | 3.000 | 16.5 | 0.165 | 3.000 | 16.5 | 0.165 | 3.00 |
| PEG-8000 | 82.5 | 0.825 | 15.001 | 82.5 | 0.825 | 14.999 | 82.5 | 0.825 | 15.00 |
| Stearic Acid | 27.5 | 0.275 | 5.000 | 27.5 | 0.275 | 5.000 | 27.5 | 0.275 | 5.00 |
| Mg Stearate | 5.5 | 0.055 | 1.000 | 5.5 | 0.055 | 1.000 | 5.5 | 0.055 | 1.00 |
| Total | 549.975 | 5.49975 | 100 | 550.050 | 5.5005 | 100 | 550.00 | 5.5 | 100 |
| Calculated Strength (Sufentanil base) | | | 0.002506159 | | | 0.005012 | | | 0.010025 |

A human clinical study was performed using healthy volunteers. The study was performed with 12 subjects (6 men and 6 women) using sufentanil-containing dosage forms (formulations #46-#48 shown in Table 1) manufactured to have a volume of 5 µL, a mass of approximately 5.5 mg, and determined to have a uniform size for all dosage strengths with dimensions of approximately 3 mm in diameter and 0.8 mm in thickness. Sufentanil dosage forms contained either 2.5 mcg, 5 mcg or 10 mcg of sufentanil base corresponding to 3.7 mcg, 7.5 mcg or 15 mcg of sufentanil citrate, respectively. All excipients were inactive and have GRAS ("generally recognized as safe") status. The sufentanil dosage forms were tested for sublingual use. Study staff administered individual dosage forms to a subject by placing them directly at the base of the frenulum using blunt-tipped forceps.

For bioavailability calculations, intravenous sufentanil, 5 mcg was diluted in 0.9% saline to a total volume of 20 mL, and was administered through an IV catheter as a continuous infusion over 10 minutes. Plasma samples were drawn from a different IV catheter at a remote location. This human trial was a cross-over design with wash-out periods between transitions from higher to lower doses. Subjects were blocked with the opioid antagonist naltrexone daily to avoid opioid-induced side-effects.

Day 0: IV sufentanil Infusion:
a Seventeen samples were collected:
−5.0 (before the start of infusion), 2.5, 5, 7.5, 10, 12.5, 15, 20, 30, 45, 60, 90, 120, 160, 320, 480 and 640 minutes
Day 2: sublingual 2.5 mcg sufentanil dosage forms;
a Seventeen samples:
−5.0 (before dosage form administration), 2.5, 5, 7.5, 10, 12.5, 15, 20, 30, 45, 60, 90, 120, 160, 320, 480 and 640 minutes
Day 3: sublingual 5.0 mcg sufentanil dosage forms;
a Seventeen samples:
−5.0 (before dosage form administration), 2.5, 5, 7.5, 10, 12.5, 15, 20, 30, 45, 60, 90, 120, 160, 320, 480 and 640 minutes
Day 4: sublingual 10.0 mcg sufentanil dosage forms;
a Seventeen samples:
−5.0 (before dosage form administration), 2.5, 5, 7.5, 10, 12.5, 15, 20, 30, 45, 60, 90, 120, 160, 320, 480 and 640 minutes
Day 7: sublingual 5.0 mcg sufentanil dosage forms repeated 4 times at 10 minute intervals;
a Twenty three samples:
−5.0 (before the first dosage form administration), 5, 7.5 minutes
10 (immediately prior to the second dosage form administration), 15, 17.5 minutes
20 (immediately prior to the third dosage form administration), 25, 27.5 minutes
30 (immediately prior to the fourth dosage form administration), 35, 40, 45, 50, 55, 60, 90, 120, 150, 190, 350, 510 and 670 minutes The total volume of blood required for pharmacokinetic sampling was approximately 455 mL.

Sufentanil concentrations in plasma samples were determined using a validated LC-MS/MS sufentanil human plasma assay. The assay demonstrated good inter-day precision and accuracy at the high, medium and low quality control sample concentrations.

Figure 9:
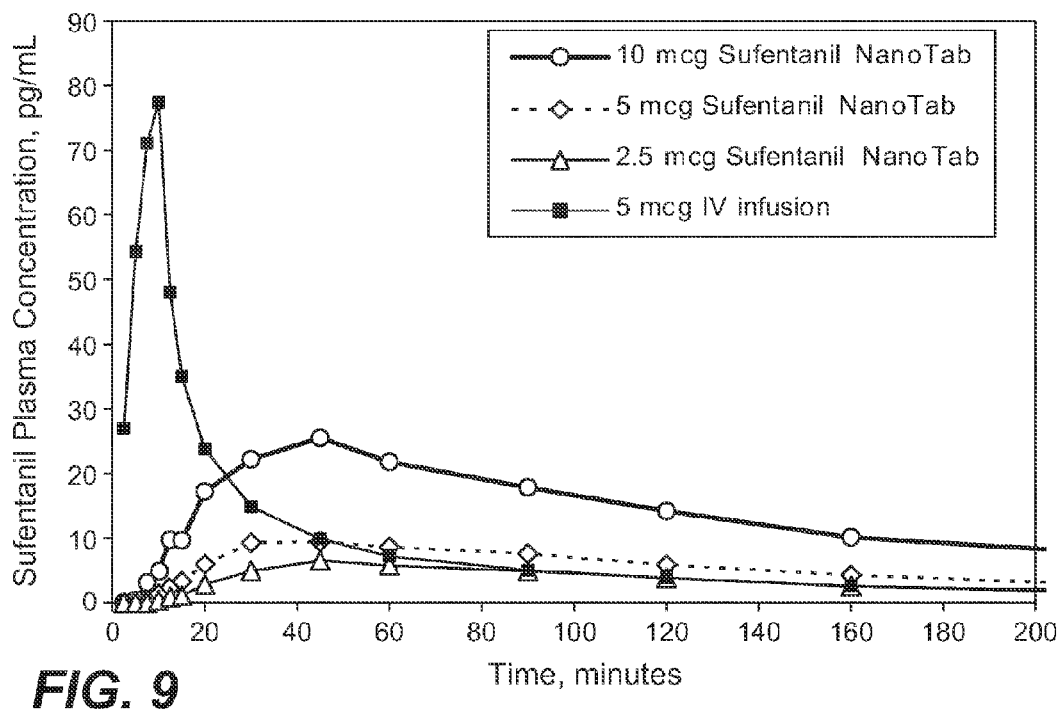
FIG. 9 is a graphic depiction of sufentanil plasma concentrations following intravenous dosing or sublingual single dose administration of three different strengths of sufentanil dosage forms in healthy human volunteers (n=12).

The dosage forms for this study eroded over a period of 10-30 minutes in all subjects. After placement of each sufentanil sublingual dosage forms in the sublingual cavity of the 12 healthy volunteers, a remarkably consistent pharmacokinetic profile was obtained for the three dosages (FIG. 9).

Example 2

In Vivo Evaluation of Sublingual Sufentanil Dosage Forms in a Dog Model

The following Examples 2-5 are using the Beagle dog model and the formulations for the dosage forms all are using a dosage form with a total mass of 5.5 mg. The in vivo pharmacokinetics (PK) of sufentanil following sublingual administration of the 5 mcg dosage forms (formulation #44 for dogs, which is the same as the human formulation #47) described above were evaluated in a healthy Beagle dog model. Briefly, single 5 mcg dosage forms described above were administered sublingually in fully awake healthy dogs by direct placement in the sublingual cavity. A total of three dogs were evaluated. Following administration, the position of the dosage form in the sublingual cavity was observed visually at 5-15 minute intervals following administration. The sublingual sufentanil PK was compared with that of IV administered sufentanil at the same dose level.

Figure 10:
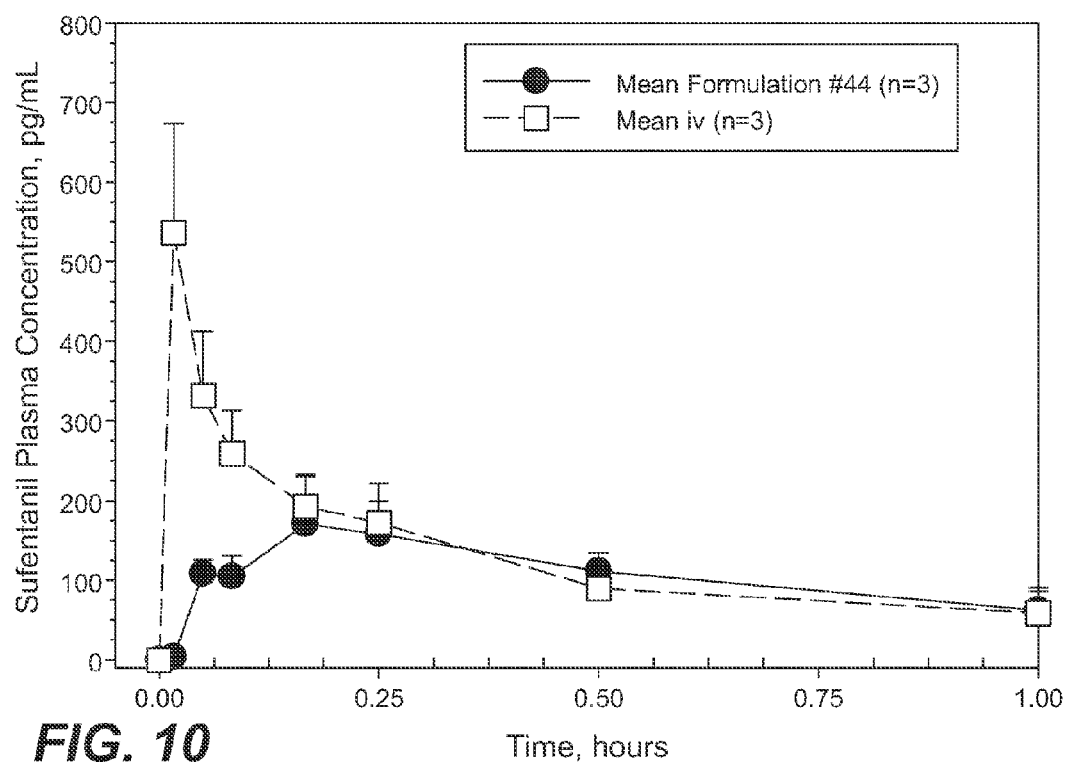
FIG. 10 is a graphic depiction of sufentanil plasma concentrations following sublingual administration of a sufentanil formulation #44 (equivalent to human #47 formulation; n=3) compared to intravenous sufentanil administration (n=3) in a healthy, conscious Beagle dog model. Error bars represents standard errors around the mean (SEM).

All dogs were catheterized via the cephalic vein for blood collections up to 2 hours post-dosing. Through the 2-hour post-dose blood collection, all dogs were fitted with an Elizabethan collar to prevent removal of the catheter. The catheter was removed following the 2-hour blood collection. The 4-, 8-, and 24-hour post-dose blood collection were collected from the cephalic or other suitable vein. Approximately 2 ml of blood were collected into pre-chilled tubes containing potassium EDTA at the following time points: prior to dosing and approximately 1, 3, 5, 10, 15, 30 min, 1, 2, 4, 8 and 24 hours post-dose. The samples were analyzed with the appropriately validated LC/MS/MS method for the determination of sufentanil citrate in dog plasma. The sufentanil plasma concentrations and the pharmacokinetic results are shown in FIG. 10 and Table 3.

TABLE 2

PK Analyses of the IV (5 mcg) and Sublingual Sufentanil Dosing Arms in the Human Clinical Study using Three Dosage Strengths (2.5 mcg = #46, 5 mcg = #47, 10 mcg = #48)

| Group | AUC (hr*ng/ml) (mean ± SD) | F (%) | Absorption Variability (% CV) | $C_{max}$ (pg/mL) | $T_{max}$ (min) | Plasma Elimination Half-life (hr) | Therapeutic Time Ratio[1] |
|---|---|---|---|---|---|---|---|
| Intravenous Sufentanil | 0.0368 ± 0.0076 | — | 20.7 | 0.0813 ± 0.0281 | 9.6 ± 1.8 | 1.19 ± 0.18 | 0.067 |
| Sublingual Sufentanil dosage form (Formulation #46) | 0.0178 ± 0.0044 | 97.8 | 24.7 | 0.0068 ± 0.0021 | 43.8 ± 7.8 | 1.65 ± 0.43 | 0.74 |
| Sublingual Sufentanil dosage form (Formulation #47) | 0.0273 ± 0.0093 | 76.7 | 34.1 | 0.0109 ± 0.0035 | 46.2 ± 17.4 | 1.54 ± 0.57 | 0.75 |
| Sublingual Sufentanil dosage form (Formulation #48) | 0.0705 ± 0.0194 | 98.2 | 27.5 | 0.0275 ± 0.0077 | 40.8 ± 13.2 | 1.71 ± 0.40 | 0.72 |
| Repeat Dosing of #47 Sufentanil dosage form every 10 min. × 4 | 0.1403 ± 0.0361 | 96.4 | 25.7 | 0.0464 ± 0.0124 | 62.4 ± 13.8 | 1.97 ± 0.30 | NA |

[1]Represents the relative time that the drug achieves therapeutic levels (above 50% of $C_{max}$) and it is calculated by the formula: TTR = (Time spent above 50% of $C_{max}$)/(IV Terminal elimination half-life). The denominator is obtained from literature and is 148 min in humans for sufentanil.

TABLE 3

PK Analysis of Sufentanil Sublingual Dosage Forms Compared to Intravenous Sufentanil in Beagle Dogs.

| Group | AUC (Mean ± SD) | F (%) | Absorption Variability (% CV) | $C_{max}$ (pg/mL) | $T_{max}$ (min) | Plasma Half-life (min) | Therapeutic Time Ratio[1] |
|---|---|---|---|---|---|---|---|
| Intravenous Sufentanil | 211.5 ± 48.2 | — | 22.8 | 536.7 ± 186.1 | 1.6 ± 0.6 | 10.3 ± 4.5 | 0.05 ± 0.02 |
| Sublingual Sufentanil dosage form (Formulation #44) | 161.2 ± 23.1 | 74.8 ± 10.7 | 14.3 | 222.7 ± 25.9 | 11.7 ± 2.5 | 33.3 ± 5.8 | 0.28 ± 0.16 |

[1]Represents the relative time that the drug achieves therapeutic levels (above 50% of $C_{max}$) and it is calculated by the formula: TTR = (Time spent above 50% of $C_{max}$)/(IV Terminal elimination half-life). The denominator is obtained from literature and is 139 min in beagle dogs for sufentanil.

Example 3

Exemplary Sufentanil Dosage Forms to Control Drug Release and In Vivo Pharmacokinetics For purposes of illustration, a longer duration dosage form (formulation #58) was prepared with sufentanil citrate in order to evaluate a slower rate of drug release and in vivo pharmacokinetics of a longer-acting dosage form. This slower disintegrating sufentanil dosage form, as described in Table 4 was prepared by direct compression and tested as described above. The range of erosion times in dogs was 35-120 minutes and the bioadhesion of the placebo formulation was measured as described above and determined to be 0.18-0.08 N/cm².

Sample analysis was performed using a validated LC/MS/MS method for analysis of sufentanil in dog plasma. Pharmacokinetic analysis was performed using a non-compartmental model of absorption. The results of a limited PK analysis are shown in Table 5.

TABLE 4

Slow Disintegrating Sufentanil Formulation.

| Composition | Formulation # 58 |
|---|---|
| Sufentanil citrate | 0.5456 |
| Mannitol | 40.3 |
| Carbopol 971 | 20.00 |
| PEG 8000 | 25.60 |
| HPMC | 10.00 |
| Polyox 303 | 2.60 |
| Mg Stearate | 1.00 |
| Total | 100.00 |

TABLE 5

PK Analyses for the Slow-Disintegrating Sublingual Sufentanil Dosage Form in Beagle Dogs.

| Group | Plasma Half-life (min) | Therapeutic Time Ratio[1] |
|---|---|---|
| Sublingual formulation #58 | 205 ± 93.1 | 1.13 ± 0.69 |

[1]Represents the relative time that the drug achieves therapeutic levels (above 50% of $C_{max}$) and it is calculated by the formula: TTR = (Time spent above 50% of $C_{max}$)/(IV Terminal elimination half-life). The denominator is obtained from the literature and is 139 min in beagle dogs for sufentanil.

Example 4

In Vivo Study of Sublingual Sufentanil Solution and Swallowing of Sufentanil dosage forms in a Dog Model A. Evaluation of Bioavailability of Sufentanil Following Sublingual Administration of a Solution Dosage Form The bioavailability of sufentanil following sublingual administration from a solution as compared to that intravenously was evaluated in a healthy, conscious Beagle dog animal model, as indicated in Table 6. In both arms of the study the commercially available formulation of sufentanil citrate (Sufenta® 50 µg/mL) was used and was dosed at the same total dose of 5 mcg of sufentanil base. Intravenous administrations (Group 1) were performed by single administration (n=3) of Sufenta® 50 µg/mL by bolus injection to the cephalic vein via a sterile needle and syringe of appropriate size. For the sublingual administrations (Group 2) the test article was prepared by appropriately diluting Sufenta® 50 µg/mL with 0.9% w/w to the same final dose of 5 mcg of sufentanil base and was administered twice sublingually (n=6 total), with each dose separated by a minimum of a 2-day washout. Doses were slowly applied under the tongue, adjacent to the frenulum via a sterile syringe. Blood samples were collected from a jugular or other suitable vein prior to dosing and approximately 1, 3, 5, 10, 15, 30 min, 1, 2, 4, 8 and 24 hours post-dose. Approximately 2 mL of blood were collected per time-point into pre-chilled tubes containing $K_2$ EDTA. The samples were centrifuged at 3,000×g for approximately 10 minutes in a refrigerated centrifuge. Plasma was collected and frozen within 20 minutes of centrifugation at approximately −70° C. and was maintained at the same temperature until analysis. Sample analysis was performed using a validated LC/MS/MS method for analysis of sufentanil in dog plasma.

Figure 11:
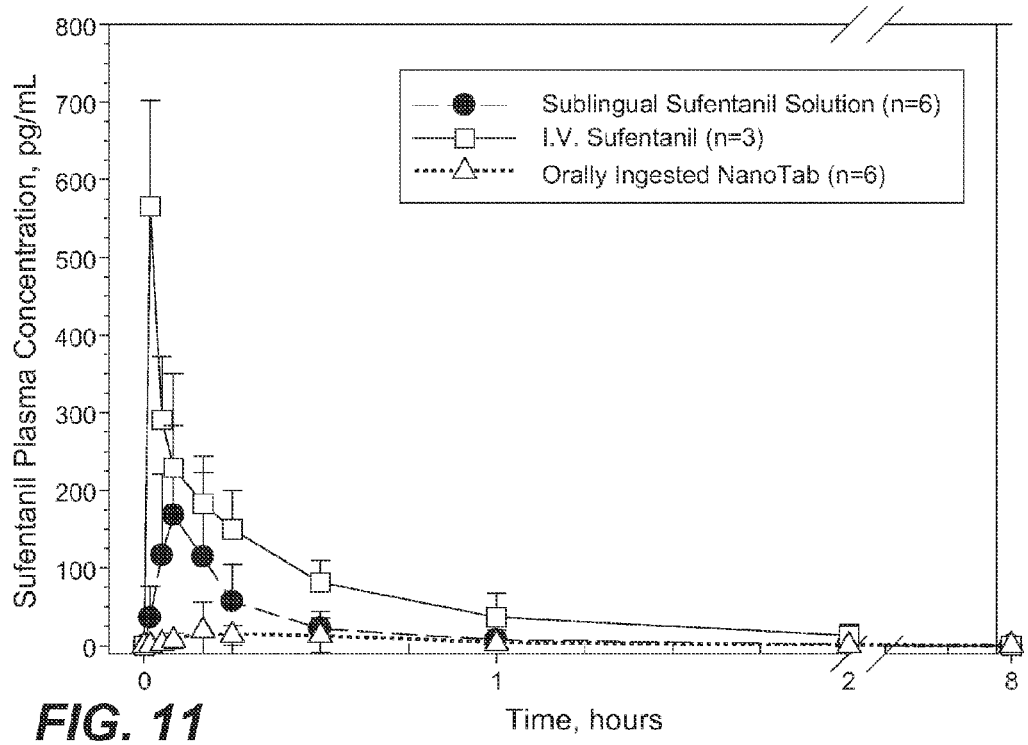
FIG. 11 is a graphic depiction of sufentanil plasma concentrations following sublingual administration of a sufentanil solution (n=6) or following oral ingestion of a sufentanil (n=6) compared to intravenous administration of sufentanil (n=3) in a healthy, conscious Beagle dog model. Error bars represents ±standard error around the mean (SEM).

Pharmacokinetic analysis was performed using a non-compartmental model of absorption. The sufentanil plasma concentrations are graphed in FIG. 11. The results of the PK analysis are shown in Table 7.

B. Evaluation of Bioavailability of Sufentanil Following Oral Ingestion of a Dosage Form The bioavailability of sufentanil following ingestion of a 5 mcg sufentanil dosage form (formulation #44, which is the same formulation as #47 used in the human study above) as compared to intravenous sufentanil administration was evaluated in a healthy, conscious Beagle dog animal model, as described in the previous example. A single 5 mcg dosage form was administered twice orally, with each dose separated by a minimum of a 2-day washout for a total of n=6 (Table 6). The dosage forms were placed manually as far back as possible in the throat and flushed with water to promote the swallow response in the animal. Pharmacokinetic analysis was performed using a non-compartmental model of absorption. The sufentanil plasma concentrations are shown graphed in FIG. 11. The results of the PK analysis are shown in Table 7.

Figure 12:
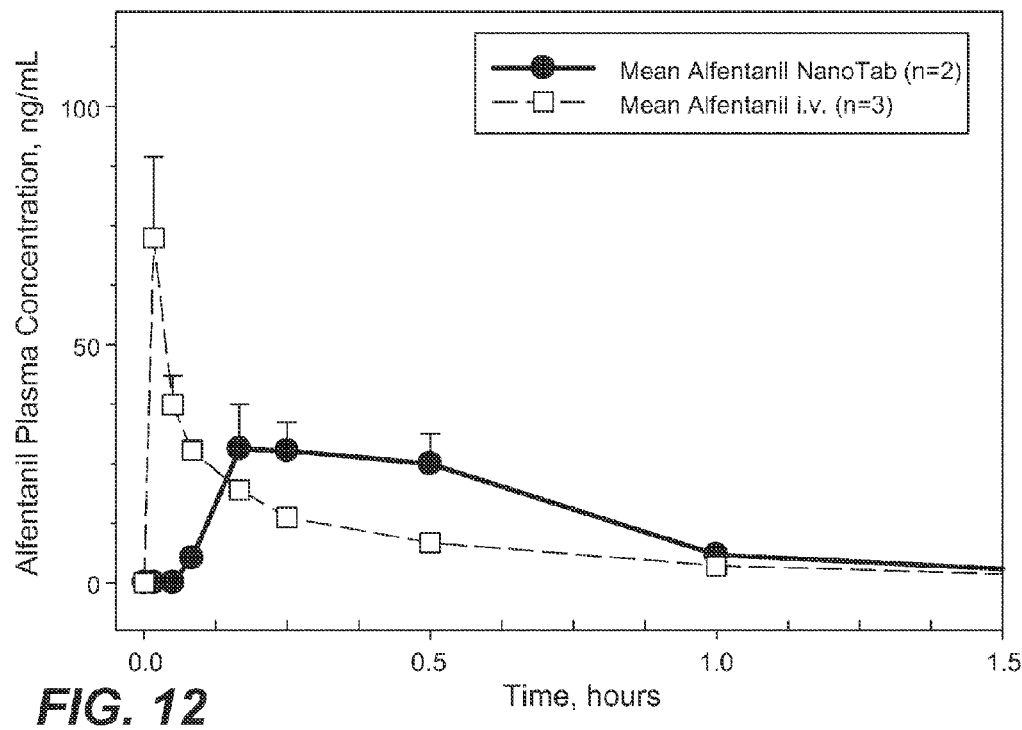
FIG. 12 is a graphic depiction of alfentanil plasma concentrations following sublingual administration of an alfentanil NanoTab™ (n=2) compared to intravenous alfentanil administration (n=3) in a healthy, conscious Beagle dog model. Error bars represents ±standard error around the mean (SEM).
Figure 13:
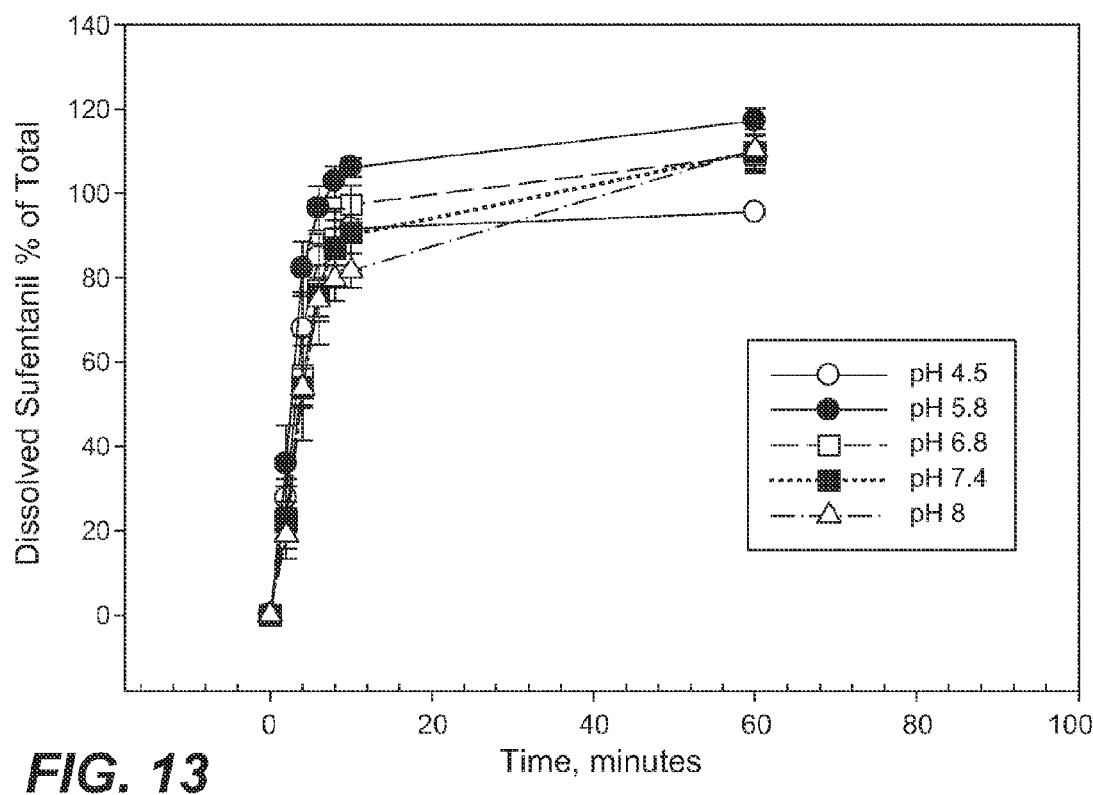
FIG. 13 is a graphic depiction of the effect of pH on dissolution kinetics of sufentanil from exemplary oral transmucosal formulation.

The dosing parameters for this study are shown in Table 12. The alfentanil plasma concentrations are graphed in FIG. 12. PK analysis was performed using a non-compartmental absorption model. The results of the PK analysis are shown in Table 13. Blood sampling and storage mirrored the conditions described earlier; sample analysis was performed using a validated LC/MS/MS method for analysis of alfentanil in dog plasma.

TABLE 6

Organization of Test Groups

| Group | Treatment | Dose Level (μg)[a] | Route of Administration | Number of Animals[b] (Males) | Total Number of Animals, n |
|---|---|---|---|---|---|
| 1 | Sufentanil solution | 5.0 | IV | 3 | 3 |
| 2 | Sufentanil solution | 5.0 | Sublingual | 3[c] | 6 |
| 3 | Ingested Sufentanil dosage form | 5.0 | Oral | 3[c] | 6 |

[a] = Expressed as a free base.
[b] = Same animals will be used for Groups 1 through 3 with a minimum 2-day washout period between dosing.
[c] = Group 2 & 3 animals were dosed twice with a minimum 2-day washout period for a total of n = 6
[d] = Normal (0.9% w/w) saline was used to dilute the test article (Sufenta ® 50 μg/mL) to the desired concentration.

TABLE 11

Exemplary Alfentanil Dosage Form

| Formulation #63 | % composition |
|---|---|
| Alfentanil HCl | 5.00 |
| Mannitol | 52.00 |
| Carbopol 974 | 7.00 |
| PEG 8000 | 35.00 |
| Mg Stearate | 1.00 |
| Total | 100.00 |

TABLE 7

PK Analyses of Intravenously Administered Sufentanil Compared to a Sublingually Instilled Sufentanil Solution and an Ingested Sufentanil Dosage Form in Beagle Dogs.

| Group | AUC (Mean ± SD) | F1 (%) | Absorption Variability (% CV) | $T_{max}$ (min) | $C_{max}$ (pg/mL) | Plasma Half-life (min) | Therapeutic Plateau Ratio[1] |
|---|---|---|---|---|---|---|---|
| Intravenous Sufentanil | 123.3 ± 49.3 | — | 21.8 | 1.0 ± 0.0 | 536.7 ± 186.1 | 2.8 ± 0.4 | 0.02 ± 0.0 |
| Sublingual Sufentanil solution | 58.3 ± 36.4 | 40.0 ± 32.7 | 81.8 | 4.3 ± 1.0 | 236.4 ± 170.0 | 8.3 ± 4.5 | 0.04 ± 0.02 |
| Ingested dosage form | 15.9 ± 22.4 | 12.2 ± 15.3 | 134.2 | 14.6 ± 9.9 | 33.8 ± 33.2 | 22.5 ± 16.8 | 0.13 ± 0.09 |

[1] Represents the relative time that the drug achieves therapeutic levels (above 50% of $C_{max}$) and it is calculated by the formula: TTR = (Time spent above 50% of $C_{max}$)/(IV Terminal elimination half-life). The denominator is obtained from the literature and is 139 min. in beagle dogs for sufentanil.

Example 5

In Vivo Evaluation of Sublingual Alfentanil HCl Dosage Forms in a Dog Model

For purposes of illustration of another drug use for the dosage form, an additional dosage form was prepared with alfentanil HCl in order to demonstrate the ability of the dosage forms described in this application to effectively improve the PK of alfentanil compared to that of the IV route of administration. The formulation composition, a medium disintegrating dosage form, is described in Table 11. The erosion time in dogs of formulation #63 was 20 minutes and the bioadhesion was measured at 0.056±0.01 N/cm² for the placebo formulation.

TABLE 12

Dosing Parameters for Administration of Sublingual Alfentanil Dosage Forms and an Intravenous Alfentanil Solution in Beagle Dogs.

| Group | Treatment | Dose Level (μg)[a] | Route of Administration | Number of Animals (Males) |
|---|---|---|---|---|
| 1 | Alfentanil solution | 253 | IV | 3 |
| 2 | Alfentanil dosage form | 239.0 ± 16.2 | Sublingual | 2 |

[a] = Expressed as a free base.
[b] = Same animals were used for Groups 1 and 2 with a minimum 2-day washout period between dosing.

TABLE 13

PK Analyses of Alfentanil Sublingual Dosage Forms compared to Intravenous Alfentanil in Beagle Dogs.

| Group | AUC (Mean ± SD) | F (%) | Absorption Variability (% CV) | $T_{max}$ (min) | $C_{max}$ (ng/mL) | Plasma Half-life (min) | Therapeutic Time Ratio[1] |
|---|---|---|---|---|---|---|---|
| Intravenous Alfentanil | 15.3 ± 1.6 | — | 10.5 | 1 ± 0 | 139.1 ± 76.4 | 4.4 ± 2.4 | 0.04 ± 0.02 |
| Sublingual Alfentanil dosage form | 14.4 ± 0.7 | 94.1 ± 4.6 | 4.9 | 15.0 ± 4.2 | 35.5 ± 2.6 | 40.8 ± 8.5 | 0.33 ± 0.07 |

Represents the relative time that the drug achieves therapeutic levels (above 50% of $C_{max}$) and it is calculated by the formula: TTR=(Time spent above 50% of $C_{max}$)/(IV Terminal elimination half-life). The denominator is obtained from literature and is 104 min. in beagle dogs.

Example 6

Acute Pain Management in the Outpatient Setting by Administering a Sufentanil-Containing Dosage Form Using a Device A pharmacist loads a drug dispensing device with a drug cartridge which includes 40 sufentanil dosage forms. Each cartridge has two colored initialization tablets (called "shipping tablets") arranged to be the first two tablets dispensed. The device has a means for loading the cartridge, which is either a port, hatch, or door that is secure and inaccessible to unauthorized users. Once the pharmacist has loaded the cartridge into the device, he locks the device access port, hatch or door. The pharmacist then docks the dispensing device for the first time to a dock that is connected to a personal or other computer, using the docking connector, and then programs the device. Programming involves uploading the dosage strength of the dosage forms, the number of dosage forms loaded in the device, the prescribed frequency of dosage form usage, the number of dosage forms to be used per day, the current date and time, the preferred language, a valid thumbprint or other identification for identifying the patient, and the physician's identification information, in case the device is lost and found.

Once the dispensing device is programmed, the pharmacist demonstrates proper usage and tests the device by dispensing a single shipping tablet. The pharmacist then gives the dispensing device to the patient and observes the patient dispense a shipping tablet to ensure proper usage and functionality. Along with the dispensing device, the pharmacist provides the patient with a radio frequency identification (RFID) tag that must be within approximately 5 inches of the device to allow the dispensing device to operate.

When the patient wants to administer a dose of the drug, he or she will hold the dispensing device, and push any button to wake the device up from its sleep mode. The device will query the user for either a thumbprint reading or a personal identification number (PIN). The device will then search for a validated RFID key within range. Once these conditions are met, the dispensing device will query its internal memory and clock to make sure that the dosage regimen programmed by the pharmacist is not being violated by the current usage request. At this point the device displays status information, such as the date and time, the number of doses left, the last time a dosage was used, the patient's name, etc., and the pharmacist informs the patient that the device is ready to dispense the dosage forms by a visual and/or audible signal.

The patient will hold the dispensing end of the device under his or her tongue and press the dispensing lever. When the dosage form is dispensed a tone will sound to inform the patient that the dosage form was properly delivered. At this point the device will lock down to prevent further dispensing until the preprogrammed lock-out time has passed, at which time the device will be ready to use again.

Example 7

Acute Pain Management in the Inpatient Setting by administering a Sufentanil-Containing Dosage Form Using A Device A post operative patient requires acute pain treatment following surgery. The surgeon prescribes oral transmucosal sufentanil to be administered using the drug dispensing device. The attending nurse takes the prescription order to the pharmacist or automated pharmaceutical inventory management system (e.g. Pyxis) and obtains a sufentanil-containing drug cartridge for sublingual delivery. The cartridge is labeled and equipped with an RFID electronic tag containing drug label information. The cartridge is labeled and equipped with an RFID electronic tag containing drug label information.

The nurse then takes a disposable dispensing portion of the drug dispensing device from inventory, and proceeds to a base station to obtain a reusable controller portion of the drug dispensing device that has completed its recharge cycle and is ready for use. The nurse inserts the drug cartridge into the disposable dispensing portion, and then affixes this to the reusable controller portion of the drug dispensing device and locks the disposable portion into the reusable portion of the drug dispensing device. At this point the device reads the RFID tag on the drug cartridge and uploads the appropriate drug information, including the type of drug, the dosage strength, the programmed lockout period between doses, etc. The nurse confirms the proper drug cartridge information has been read by the drug dispensing device and gives the drug dispensing device to the patient for patient controlled dispensing of the pain medication.

When the patient requires pain medication, she takes the drug dispensing device in her hand, and places the dispensing tip in her mouth, under her tongue and presses the dispense button. The drug dispensing device then does an internal check to ensure that the proper lockout period has elapsed since the last dosage dispense. At this point the drug dispensing device dispenses a dosage form under the patient's tongue and provides feedback that dosing was successful. The patient removes the drug dispensing device from her mouth and allows the sublingual dosage form to dissolve under her tongue. The patient may attempt to dispense as frequently as she desires, but the drug dispensing device will only allow successful dosing after the appropriate lockout period has elapsed. The drug dispensing device electronically logs the dispensing attempts and successful dispenses in its dosing history.

Periodically the nurse checks on the patient and drug dispensing device. During such checks, the nurse inspects the drug dispensing device to see that there are no errors and to check the number of remaining dosage forms in the drug dispensing device, and returns it to the patient.

When the patient is discharged, the nurse takes the drug dispensing device and unlocks the reusable portion from the disposable portion, disposes of the cartridge and disposable portion of the drug dispensing device. The nurse then connects the reusable portion of the device to a computer and uploads the patient use information from the drug dispensing device to the computer for input into the patient's medical records. The nurse cleans the reusable controller portion and returns it to the base station for recharging.

Example 8

Acute Pain Management in the Inpatient Setting by Administering a Sufentanil-Containing Dosage Form Using A Device and a Portable Dock A post operative patient requires acute pain treatment following surgery. The surgeon prescribes oral transmucosal sufentanil to be administered using the drug dispensing device. The attending nurse takes the prescription order to the pharmacist or automated pharmaceutical inventory management system (e.g. Pyxis) and obtains a sufentanil-containing drug cartridge for sublingual delivery. The cartridge is labeled and equipped with an RFID electronic tag containing drug label information. The cartridge is labeled and equipped with an RFID electronic tag containing drug label information. The cartridge includes a shipping tablet or initialization tablet in the first to be dispensed location of the dosage form stack.

The nurse then takes a disposable dispensing portion of the drug dispensing device from inventory, and proceeds to a base station to obtain a reusable controller portion of the drug dispensing device that has completed its recharge cycle and is ready for use. The nurse inserts the drug cartridge into the disposable dispensing portion, and then affixes this to the reusable controller portion of the drug dispensing device. Next, the nurse takes a portable dock (or docking fob) from the base station where it has been recharging, and docks the assembled drug dispensing device to the portable dock. The portable dock and the assembled drug dispensing device communicate electronically and a setup menu comes up on the portable dock for setting up the drug dispensing device.

At this point the device locks the reusable and disposable portions together, reads the RFID tag on the drug cartridge and uploads the appropriate drug information, including the type of drug, the dosage strength, the lockout period between doses, etc. The dispensing device writes a code to the RFID tag on the cartridge identifying it as a used cartridge. The nurse enters her fingerprint in the fingerprint reader on the portable dock to gain secured access and proceeds to set up the drug dispensing device for use. The set up procedure includes entering user identification, the nurse's identification, confirming the proper time on the device, and confirming the proper drug cartridge information. The nurse then takes a disposable RFID bracelet and places this adjacent to the drug dispensing device at which point the drug dispensing device reads the tag and the nurse confirms that the proper bracelet tag has been read.

The nurse then confirms proper setup of the drug dispensing device by pressing the dispensing button once. The drug dispensing device actuates, dispensing the shipping tablet facsimile into the nurses hand, confirming proper operation. The drug dispensing device detects the dispensing of the shipping tablet, allowing for an internal system check of proper operation and internal calibration of the newly assembled system. If the internal dispensing check is successful, the portable dock queries the nurse to confirm that the shipping table was properly dispensed, and the nurse confirms the proper setup. The nurse then disengages the drug dispensing device from the portable dock, and proceeds to the patient's bedside for the final steps of setup.

The nurse places the RFID bracelet on the patient's wrist and affixes a theft resistant tether to the patient's bed and the other end to the drug dispensing device. The nurse then instructs the patient on proper use of the sublingual drug dispensing device, and gives the drug dispensing device to the patient for patient controlled dispensing of sufentanil.

When the patient requires pain medication, she takes the drug dispensing device in her hand, and places the dispensing tip in her mouth, under her tongue and presses the dispensing button. The drug dispensing device then does an internal check to ensure that the proper lockout period has elapsed since the last dosage dispense, and that the patient's RFID bracelet is present and readable. At this point the drug dispensing device dispenses a dosage form under the patient's tongue and provides a feedback that dosing was successful. The patient removes the drug dispensing device from her mouth and allows the sublingual dosage form to dissolve under her tongue. The patient may attempt to dispense as frequently as she desires, but the drug dispensing device will only allow successful dosing after the appropriate lockout period has elapsed. The drug dispensing device electronically logs the dispensing attempts and successful dispenses in its dosing history.

Periodically the nurse checks on the patient and device. During such a patient check in the nurse brings a portable docking FOB and docks the device to the FOB. The electronic connection enables the nurse to download the information from the drug dispensing device to the fob. This information includes the use history, drug information, number of remaining dosage forms and duration of use since initial set up. The nurse then enters her fingerprint in the finger print scanner to gain access to the information and to drug dispensing device. Because the patient is requiring an additional dose of drug prior to the lockout period expiring, the nurse overrides the lockout period and then returns the drug dispensing device to the patient at which point the patient is able to take another dose.

The nurse leaves the patient's room with the portable docking FOB and returns to the nurse's station to record the dosing history in the patient's records. When finished the nurse returns the FOB to the base station for recharging.

When the patient has used all of the dosage forms in the drug dispensing device, the nurse brings the portable docking fob into the patient's room and docks the drug dispensing device to the FOB. The nurse then enters her fingerprint in the fingerprint scanner on the fob to gain secured access to the drug dispensing device. Next, the nurse unlocks the security tether and disconnects the drug dispensing device from the bed. She then unlocks the drug dispensing device and removes it from the fob for disassembly. The nurse disconnects the disposable portion from the reusable portion, and removes the cartridge from the disposable portion. The nurse disposes of the disposable portion and the cartridge, and wipes the reusable controller portion with an antiseptic wipe to clean it before returning it to the base station. The reusable controller portion requires that the nurse return it to the base station where it recharges and runs an internal diagnostic test before being ready for use again.

The nurse then proceeds to set up a new drug dispensing device as described above and provides this to the patient.

Although the foregoing invention has been described in some detail by way of illustration and example for purposes of clarity and understanding, it will be apparent to those skilled in the art that certain changes and modifications may be practiced. Various aspects of the invention have been achieved by a series of experiments, some of which are described by way of the following non-limiting examples. Therefore, the description and examples should not be construed as limiting the scope of the invention, which is delineated by the appended description of exemplary embodiments.

What is claimed is:

1. A method, comprising:
    inserting a distal end portion of a housing of a device into a mouth, the device configured to deliver a bioadhesive, small-volume, solid drug tablet containing a dosage of sufentanil;
    moving an end portion of a delivery member to a first stopped position within a delivery passage defined by the housing, a distal end portion of the housing defining an exit opening and a tablet cartridge channel, a surface of the delivery member positioned to prevent movement of the drug tablet from the tablet cartridge channel to the delivery passage when the end portion of the delivery member is in the first stopped position;
    moving the end portion of the delivery member in a proximal direction to a second position within the delivery passage such that the tablet cartridge channel is in communication with the delivery passage;
    conveying the drug tablet into the delivery passage via the tablet cartridge channel; and
    moving the end portion of the delivery member in a distal direction to a third position within the delivery passage to convey the drug tablet through the exit opening.

2. The method of claim 1, wherein the moving the end portion of the delivery member to the first stopped position includes moving the end portion of the delivery member in the proximal direction.

3. The method of claim 1, further comprising:
    moving the end portion of the delivery member in the distal direction, before the moving the end portion of the delivery member to the first stopped position, to convey a shipping tablet through the exit opening, the shipping tablet different than the drug tablet.

4. The method of claim 1, wherein at least one of the moving the end portion of the delivery member to the first stopped position, the moving the end portion of the delivery member in the proximal direction or the moving the end portion of the delivery member in the distal direction includes bending the delivery member.

5. The method of claim 1, wherein:
    the end portion of the delivery member is a first end portion; and
    at least one of the moving the first end portion of the delivery member to the first stopped position, the moving the first end portion of the delivery member in the proximal direction or the moving the first end portion of the delivery member in the distal direction includes rotating a second end portion of the delivery member about a hub.

6. The method of claim 1, wherein the moving the end portion of the delivery member in the distal direction includes moving the end portion of the delivery member within a nonlinear portion of the delivery passage.

7. The method of claim 1, wherein the moving the end portion of the delivery member in the distal direction includes conveying the drug tablet through a seal disposed about the exit opening.

8. The method of claim 1, wherein the conveying the drug tablet includes conveying the drug tablet from a tablet cartridge at least partially disposed within the tablet cartridge channel.

9. The method of claim 1, wherein the conveying the drug tablet includes conveying the drug tablet from a tablet cartridge in response to a force produced by a spring disposed within the tablet cartridge.

10. The method of claim 1, further comprising:
    sensing the presence of the drug tablet during the moving the end portion of the delivery member in the distal direction.

11. The method of claim 1, further comprising:
    sensing, before the moving the end portion of the delivery member to the first stopped position, the presence of the end portion of the delivery member at a predetermined location within the delivery passage.

12. The method of claim 1, wherein the drug tablet contains an amount of sufentanil selected from the group consisting of 5 mcg, 10 mcg, 15 mcg, 20 mcg, 30 mcg, 40 mcg, 50 mcg, 60 mcg, 70 mcg, 80 mcg and 100 mcg.

13. A method, comprising:
    inserting a distal end portion of a housing of a device into a mouth, the device configured to deliver a bioadhesive, small-volume, solid drug tablet containing a dosage of sufentanil from a tablet cartridge;
    moving a first end portion of a delivery member to a first stopped position within a delivery passage defined by the housing of the device, the housing further defining an exit opening;
    moving the first end portion of the delivery member in a proximal direction to a second position within the delivery passage to receive the drug tablet from the tablet cartridge; and
    rotating a second end portion of the delivery member to move the first end portion of the delivery member in a distal direction to a third position within the delivery passage to convey the drug tablet through the exit opening.

14. The method of claim 13, wherein a surface of the delivery member is positioned to prevent movement of the drug tablet from the tablet cartridge into the delivery passage when the first end portion of the delivery member is in the first stopped position.

15. The method of claim 13, wherein the moving the first end portion of the delivery member in the proximal direction includes placing a tablet cartridge channel in communication with the delivery passage.

16. The method of claim 13, wherein at least one of the moving the first end portion of the delivery member to the first stopped position, the moving the first end portion of the delivery member in the proximal direction or the rotating the second end portion of the delivery member includes bending the delivery member.

17. The method of claim 13, wherein the moving the first end portion of the delivery member in the distal direction includes moving the first end portion of the delivery member within a curved portion of the delivery passage.

18. The method of claim 13, further comprising:

moving the first end portion of the delivery member in the distal direction, before the moving the first end portion of the delivery member to the first stopped position, to convey a shipping tablet through the exit opening, the shipping tablet different than the drug tablet.

19. The method of claim 13, further comprising:

conveying the drug tablet from the tablet cartridge into the delivery passage in response to a force produced by a spring disposed within the tablet cartridge.

20. The method of claim 13, further comprising:

sensing the presence of the drug tablet when the first end portion of the delivery member is being moved to the third position.

21. A method, comprising:

inserting a distal end portion of a housing of a device into a mouth, the device configured to deliver a bioadhesive, small-volume, solid drug dosage tablet containing a dosage of sufentanil from a tablet cartridge;

moving, at a first time, an end portion of a delivery member in a distal direction to a stopped position within a delivery passage defined by the housing to convey a shipping tablet through an exit opening defined by the housing;

producing a signal uniquely associated with the shipping tablet during the moving;

moving, at a second time, the end portion of the delivery member in a proximal direction within the delivery passage to receive the drug dosage tablet from the tablet cartridge; and moving, at a third time, the end portion of the delivery member in the distal direction within the delivery passage to convey the drug dosage tablet through the exit opening.

22. The method of claim 21, further comprising:

moving, after the first time and before the second time, the end portion of the delivery member in the proximal direction such that a surface of the delivery member is positioned to prevent movement of the drug dosage tablet from the tablet cartridge.

23. The method of claim 21, wherein at least one of the moving at the first time, the moving at the second time or the moving at the third time includes bending the delivery member.

24. The method of claim 21, wherein:

the end portion of the delivery member is a first end portion; and at least one of the moving the first end portion of the delivery member at the first time, the moving the first end portion of the delivery member at the second time or the moving the first end portion of the delivery member at the third time includes rotating a second end portion of the delivery member.

25. The method of claim 21, wherein at least one of the moving the end portion of the delivery member at the first time or the moving the end portion of the delivery member at the third time includes moving the end portion of the delivery member within a nonlinear portion of the delivery passage.

26. The method of claim 21, wherein the producing the signal includes sensing the presence of the shipping tablet at a predetermined location within the delivery passage.

27. The method of claim 21, wherein the producing the signal includes sensing the presence of the shipping tablet at a predetermined location within the delivery passage via an optical sensor coupled to the device.

28. The method of claim 21, wherein the drug dosage tablet contains an amount of sufentanil selected from the group consisting of 5 mcg, 10 mcg, 15 mcg, 20 mcg, 30 mcg, 40 mcg, 50 mcg, 60 mcg, 70 mcg, 80 mcg and 100 mcg.

* * * * *